(12) United States Patent
Metzger et al.

(10) Patent No.: US 8,157,869 B2
(45) Date of Patent: Apr. 17, 2012

(54) KNEE JOINT PROSTHESIS SYSTEM AND METHOD FOR IMPLANTATION

(75) Inventors: Robert Metzger, Wakarusa, IN (US); Audra Watson, Ft. Wayne, IN (US); Brian M. May, Warsaw, IN (US); Duke A. Fox, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 802 days.

(21) Appl. No.: 11/972,359

(22) Filed: Jan. 10, 2008

(65) Prior Publication Data

US 2008/0167722 A1    Jul. 10, 2008

Related U.S. Application Data

(60) Provisional application No. 60/879,733, filed on Jan. 10, 2007, provisional application No. 60/978,949, filed on Oct. 10, 2007.

(51) Int. Cl.
*A61F 2/38* (2006.01)

(52) U.S. Cl. .............. 623/20.36; 623/20.15; 623/20.28; 623/20.31; 623/20.34; 623/20.35

(58) Field of Classification Search .............. 623/20.14, 623/20.15, 20.21, 20.32, 20.34, 20.35, 20.36
See application file for complete search history.

(56) References Cited

U.S. PATENT DOCUMENTS

| 538,987 | A | 5/1895 | Turley |
|---|---|---|---|
| 3,806,961 | A | 4/1974 | Muller et al. |
| 3,848,272 | A | 11/1974 | Noiles |
| 3,859,992 | A | 1/1975 | Amstutz |
| 3,878,566 | A | 4/1975 | Bechtol |
| 3,964,106 | A | 6/1976 | Hutter, Jr. et al. |
| 4,001,897 | A | 1/1977 | Rambert et al. |
| 4,007,495 | A | 2/1977 | Frazier |
| 4,012,796 | A | 3/1977 | Weisman et al. |
| 4,041,550 | A | 8/1977 | Frazier |

(Continued)

FOREIGN PATENT DOCUMENTS

DE    3336004    6/1985

(Continued)

OTHER PUBLICATIONS

European Search Report for EP 02 25 1274 completed on Sep. 12, 2003 (mailed on Sep. 22, 2003).

(Continued)

*Primary Examiner* — David Isabella
*Assistant Examiner* — Yashita Sharma
(74) *Attorney, Agent, or Firm* — Harness, Dickey

(57) ABSTRACT

A modular knee prosthesis can include a femoral component having a superiorly extending portion, a first femoral bearing surface and a second femoral bearing surface. The superiorly extending portion can define a first tapered augment receiving surface. A tibial component can have an inferiorly extending portion and a tibial bearing surface. The inferiorly extending portion can define a second tapered augment receiving surface. A first augment can define a first receiving bore and a first stepped surface. A second augment can define a second receiving bore and a second stepped surface. The first and second augments are adapted to mate at the first and second stepped surfaces in a first position at the first tapered augment receiving surface of the femoral component and in a second position at the second tapered augment receiving surface of the tibial component.

46 Claims, 38 Drawing Sheets

U.S. PATENT DOCUMENTS

| | | |
|---|---|---|
| 4,064,567 A | 12/1977 | Burstein et al. |
| 4,136,405 A * | 1/1979 | Pastrick et al. ............ 623/20.25 |
| 4,151,615 A | 5/1979 | Hall |
| 4,202,055 A | 5/1980 | Reiner et al. |
| 4,219,893 A | 9/1980 | Noiles |
| 4,224,698 A | 9/1980 | Hopson |
| 4,284,080 A | 8/1981 | Rehder et al. |
| 4,305,394 A | 12/1981 | Bertuch, Jr. |
| 4,344,192 A | 8/1982 | Imbert |
| 4,404,691 A | 9/1983 | Buning et al. |
| 4,475,549 A | 10/1984 | Oh |
| RE31,865 E | 4/1985 | Roux et al. |
| 4,523,587 A | 6/1985 | Frey |
| 4,549,319 A | 10/1985 | Meyer |
| 4,579,558 A | 4/1986 | Ramer |
| 4,619,658 A | 10/1986 | Pappas et al. |
| 4,624,674 A | 11/1986 | Pappas et al. |
| 4,632,111 A | 12/1986 | Roche |
| 4,655,777 A | 4/1987 | Dunn et al. |
| 4,659,331 A | 4/1987 | Matthews et al. |
| 4,661,112 A | 4/1987 | Muller et al. |
| 4,676,797 A | 6/1987 | Anapliotis et al. |
| 4,676,798 A | 6/1987 | Noiles |
| 4,676,799 A | 6/1987 | Legrand et al. |
| 4,678,470 A | 7/1987 | Nashef et al. |
| 4,698,063 A | 10/1987 | Link et al. |
| 4,711,233 A | 12/1987 | Brown |
| 4,711,639 A | 12/1987 | Grundei |
| 4,714,477 A | 12/1987 | Fichera et al. |
| 4,716,894 A | 1/1988 | Lazzeri et al. |
| 4,718,909 A | 1/1988 | Brown |
| 4,718,911 A | 1/1988 | Kenna |
| 4,718,915 A | 1/1988 | Epinette et al. |
| 4,718,916 A | 1/1988 | Morscher et al. |
| 4,728,333 A | 3/1988 | Masse et al. |
| 4,735,625 A | 4/1988 | Davidson |
| 4,737,411 A | 4/1988 | Graves, Jr. et al. |
| 4,764,171 A | 8/1988 | Harder et al. |
| 4,770,658 A | 9/1988 | Geremakis |
| 4,770,659 A | 9/1988 | Kendall |
| 4,770,660 A | 9/1988 | Averill |
| 4,770,661 A | 9/1988 | Oh |
| 4,778,473 A | 10/1988 | Matthews et al. |
| 4,778,474 A | 10/1988 | Homsy |
| 4,784,662 A | 11/1988 | Muller et al. |
| 4,784,663 A | 11/1988 | Kenna |
| 4,789,663 A | 12/1988 | Wallace et al. |
| 4,790,852 A | 12/1988 | Noiles |
| 4,790,854 A | 12/1988 | Harder et al. |
| 4,795,470 A | 1/1989 | Goymann et al. |
| 4,795,471 A | 1/1989 | Oh |
| 4,798,610 A | 1/1989 | Averill et al. |
| 4,801,301 A | 1/1989 | Noiles |
| 4,813,961 A | 3/1989 | Sostegni et al. |
| 4,822,366 A | 4/1989 | Bolesky |
| 4,827,919 A | 5/1989 | Barbarito et al. |
| 4,828,566 A | 5/1989 | Griss et al. |
| 4,842,606 A | 6/1989 | Kranz et al. |
| 4,846,839 A | 7/1989 | Noiles |
| 4,846,840 A | 7/1989 | Leclercq et al. |
| 4,851,007 A | 7/1989 | Gray |
| 4,871,368 A | 10/1989 | Wagner et al. |
| 4,878,916 A | 11/1989 | Rhenter et al. |
| 4,883,488 A | 11/1989 | Bloebaum et al. |
| 4,883,492 A | 11/1989 | Frey et al. |
| 4,888,021 A | 12/1989 | Forte et al. |
| 4,892,547 A | 1/1990 | Brown |
| 4,904,265 A | 2/1990 | MacCollum et al. |
| 4,908,033 A | 3/1990 | Frey et al. |
| 4,908,034 A | 3/1990 | Weightman et al. |
| 4,908,036 A | 3/1990 | Link et al. |
| 4,911,723 A | 3/1990 | Menschik et al. |
| 4,919,674 A | 4/1990 | Schelhas et al. |
| 4,923,472 A | 5/1990 | Ugolini et al. |
| 4,936,847 A | 6/1990 | Manginelli |
| 4,936,853 A | 6/1990 | Fabian et al. |
| 4,936,855 A | 6/1990 | Sherman |
| 4,936,861 A | 6/1990 | Muller et al. |
| 4,938,769 A | 7/1990 | Shaw |
| 4,938,772 A | 7/1990 | Frey et al. |
| 4,944,756 A | 7/1990 | Kenna |
| 4,944,757 A | 7/1990 | Martinez et al. |
| 4,950,297 A | 8/1990 | Elloy et al. |
| 4,950,298 A | 8/1990 | Gustilo et al. |
| 4,950,299 A | 8/1990 | Noiles |
| 4,959,071 A | 9/1990 | Brown et al. |
| 4,960,427 A | 10/1990 | Noiles |
| 4,961,748 A | 10/1990 | Frey et al. |
| 4,963,154 A | 10/1990 | Anapliotis et al. |
| 4,963,155 A | 10/1990 | Lazzeri et al. |
| 4,964,869 A | 10/1990 | Auclair et al. |
| 4,978,356 A | 12/1990 | Noiles |
| 4,985,037 A | 1/1991 | Petersen |
| 4,990,161 A | 2/1991 | Kampner |
| 4,994,064 A | 2/1991 | Aboczky |
| 4,995,158 A | 2/1991 | Howell et al. |
| 4,995,883 A | 2/1991 | Demane et al. |
| 5,002,578 A | 3/1991 | Luman |
| 5,002,581 A | 3/1991 | Paxson et al. |
| 5,009,666 A | 4/1991 | Van Syckle et al. |
| 5,019,103 A | 5/1991 | Van Zile et al. |
| 5,019,105 A | 5/1991 | Wiley |
| 5,019,108 A | 5/1991 | Bertin et al. |
| 5,021,062 A | 6/1991 | Adrey et al. |
| 5,030,221 A | 7/1991 | Buechel et al. |
| 5,032,134 A | 7/1991 | Lindwer |
| 5,037,424 A | 8/1991 | Aboczsky |
| 5,037,438 A | 8/1991 | Davidson |
| 5,037,441 A | 8/1991 | Bouvet et al. |
| 5,041,140 A | 8/1991 | Teinturier et al. |
| 5,061,269 A | 10/1991 | Muller |
| 5,061,270 A | 10/1991 | Aboczky |
| 5,062,852 A | 11/1991 | Dorr et al. |
| 5,062,853 A | 11/1991 | Forte |
| 5,074,879 A | 12/1991 | Pappas et al. |
| 5,080,677 A | 1/1992 | Shelley |
| 5,084,051 A | 1/1992 | Tormala et al. |
| 5,092,900 A | 3/1992 | Marchetti et al. |
| 5,098,437 A | 3/1992 | Kashuba et al. |
| 5,108,437 A | 4/1992 | Kenna |
| 5,108,439 A | 4/1992 | Morscher et al. |
| 5,108,445 A | 4/1992 | Ashby et al. |
| 5,108,446 A | 4/1992 | Wagner et al. |
| 5,108,450 A | 4/1992 | Horber et al. |
| 5,112,338 A | 5/1992 | Anspach, III |
| 5,116,339 A | 5/1992 | Glock |
| 5,116,378 A | 5/1992 | Carbone |
| 5,116,379 A | 5/1992 | McLardy-Smith et al. |
| 5,116,380 A | 5/1992 | Hewka et al. |
| 5,133,760 A | 7/1992 | Petersen et al. |
| 5,133,763 A | 7/1992 | Mullers et al. |
| 5,137,535 A | 8/1992 | Keller |
| 5,137,536 A | 8/1992 | Koshino et al. |
| 5,141,512 A | 8/1992 | Farmer et al. |
| 5,147,406 A | 9/1992 | Houston et al. |
| 5,152,796 A | 10/1992 | Slamin |
| 5,152,797 A | 10/1992 | Luckman et al. |
| 5,163,963 A | 11/1992 | Hewka et al. |
| 5,163,966 A | 11/1992 | Norton et al. |
| 5,169,399 A | 12/1992 | Ryland et al. |
| 5,171,243 A | 12/1992 | Kashuba et al. |
| 5,171,276 A | 12/1992 | Caspari et al. |
| 5,171,286 A | 12/1992 | Lawes et al. |
| 5,171,313 A | 12/1992 | Salyer |
| 5,171,323 A | 12/1992 | Willert et al. |
| 5,176,709 A | 1/1993 | Branemark |
| 5,180,394 A | 1/1993 | Davidson |
| 5,181,925 A | 1/1993 | Houston et al. |
| 5,181,929 A | 1/1993 | Prats et al. |
| 5,192,331 A | 3/1993 | Spotorno et al. |
| 5,194,066 A | 3/1993 | Van Zile |
| 5,197,488 A | 3/1993 | Kovacevic |
| 5,197,987 A | 3/1993 | Koch et al. |
| 5,197,988 A | 3/1993 | Spotorno et al. |
| 5,201,769 A | 4/1993 | Schutzer |
| 5,211,664 A | 5/1993 | Tepic et al. |
| 5,211,666 A | 5/1993 | Fetto |

| | | | | | |
|---|---|---|---|---|---|
| 5,217,496 A | 6/1993 | Bruce et al. | 5,480,451 A | 1/1996 | Grundei et al. |
| 5,217,498 A | 6/1993 | Henssge et al. | 5,480,452 A | 1/1996 | Hofmann et al. |
| 5,219,362 A | 6/1993 | Tuke et al. | 5,486,181 A | 1/1996 | Cohen et al. |
| 5,222,983 A | 6/1993 | Schmitz et al. | 5,489,311 A | 2/1996 | Cipolletti |
| 5,222,984 A | 6/1993 | Forte | 5,507,745 A | 4/1996 | Logroscino et al. |
| 5,226,915 A | 7/1993 | Bertin | 5,507,817 A | 4/1996 | Craig et al. |
| 5,242,445 A | 9/1993 | Ashman | 5,507,818 A | 4/1996 | McLaughlin |
| 5,246,459 A | 9/1993 | Elias | 5,507,820 A | 4/1996 | Pappas |
| 5,250,051 A | 10/1993 | Maryan | 5,507,826 A | 4/1996 | Besselink et al. |
| 5,258,034 A | 11/1993 | Furlong et al. | 5,507,829 A | 4/1996 | Thongpreda et al. |
| 5,258,035 A | 11/1993 | Hofmann et al. | 5,507,832 A | 4/1996 | Michielli et al. |
| 5,263,988 A | 11/1993 | Huebner | 5,510,396 A | 4/1996 | Prewett et al. |
| 5,275,601 A | 1/1994 | Gogolewski et al. | 5,522,902 A | 6/1996 | Yuan et al. |
| 5,282,867 A | 2/1994 | Mikhail | 5,527,317 A | 6/1996 | Ashby et al. |
| 5,282,870 A | 2/1994 | Moser et al. | 5,531,791 A | 7/1996 | Wolfinbarger, Jr. |
| 5,284,483 A | 2/1994 | Johnson et al. | 5,531,793 A | 7/1996 | Kelman et al. |
| 5,290,311 A | 3/1994 | Baumann et al. | 5,534,032 A | 7/1996 | Hodorek |
| 5,290,313 A | 3/1994 | Heldreth | 5,540,697 A | 7/1996 | Rehmann et al. |
| 5,290,315 A | 3/1994 | DeCarlo, Jr. | 5,549,684 A | 8/1996 | Amino et al. |
| 5,290,318 A | 3/1994 | Ling et al. | 5,549,685 A | 8/1996 | Hayes |
| 5,292,322 A | 3/1994 | Faccioli et al. | 5,549,689 A | 8/1996 | Epstein et al. |
| 5,314,478 A | 5/1994 | Oka et al. | 5,549,696 A | 8/1996 | Willi et al. |
| 5,314,479 A | 5/1994 | Rockwood, Jr. et al. | 5,549,699 A | 8/1996 | MacMahon et al. |
| 5,314,491 A | 5/1994 | Thongpreda et al. | 5,549,701 A | 8/1996 | Mikhail |
| 5,318,571 A | 6/1994 | Benson | 5,549,703 A | 8/1996 | Daigle et al. |
| 5,320,625 A | 6/1994 | Bertin | 5,549,704 A | 8/1996 | Sutter et al. |
| 5,326,358 A | 7/1994 | Aubriot et al. | 5,549,706 A | 8/1996 | McCarthy |
| 5,326,359 A | 7/1994 | Oudard et al. | 5,552,454 A | 9/1996 | Kretschmann et al. |
| 5,330,534 A | 7/1994 | Herrington et al. | 5,556,432 A | 9/1996 | Kubein-Meesenburg et al. |
| 5,336,267 A | 8/1994 | Kubein-Meesenburg et al. | 5,556,433 A | 9/1996 | Gabriel et al. |
| 5,342,360 A | 8/1994 | Faccioli et al. | 5,571,111 A | 11/1996 | Aboczky |
| 5,343,877 A | 9/1994 | Park | 5,571,193 A | 11/1996 | Kampner |
| 5,344,460 A | 9/1994 | Turanyi et al. | 5,571,194 A | 11/1996 | Gabriel |
| 5,344,461 A | 9/1994 | Phlipot | 5,571,196 A | 11/1996 | Stein |
| 5,356,629 A | 10/1994 | Sander et al. | 5,571,201 A | 11/1996 | Averill et al. |
| 5,358,529 A | 10/1994 | Davidson | 5,571,202 A | 11/1996 | Mathys, Sr. et al. |
| 5,358,530 A | 10/1994 | Hodorek | 5,580,352 A | 12/1996 | Sekel et al. |
| 5,360,449 A | 11/1994 | Branemark et al. | 5,584,837 A | 12/1996 | Petersen |
| 5,360,451 A | 11/1994 | Keller et al. | 5,593,447 A | 1/1997 | Angeli et al. |
| 5,364,403 A | 11/1994 | Petersen et al. | 5,593,449 A | 1/1997 | Roberson, Jr. |
| 5,370,692 A | 12/1994 | Fink et al. | 5,593,450 A | 1/1997 | Scott et al. |
| 5,370,693 A | 12/1994 | Kelman et al. | 5,593,451 A | 1/1997 | Averill et al. |
| 5,370,698 A | 12/1994 | Heimke et al. | 5,609,641 A | 3/1997 | Johnson et al. |
| 5,370,701 A | 12/1994 | Finn | 5,609,642 A | 3/1997 | Johnson et al. |
| 5,370,702 A | 12/1994 | Jones | 5,609,645 A | 3/1997 | Vinciguerra |
| 5,376,122 A | 12/1994 | Pappas et al. | 5,609,647 A | 3/1997 | Kalberer et al. |
| 5,376,123 A | 12/1994 | Klaue et al. | 5,609,648 A | 3/1997 | Oehy et al. |
| 5,376,124 A | 12/1994 | Gustke et al. | 5,639,280 A | 6/1997 | Warner et al. |
| 5,383,938 A | 1/1995 | Rohr et al. | 5,641,323 A | 6/1997 | Caldarise |
| 5,387,239 A | 2/1995 | Bianco et al. | 5,645,593 A | 7/1997 | Woods et al. |
| 5,387,240 A | 2/1995 | Pottenger et al. | 5,645,594 A | 7/1997 | Devanathan et al. |
| 5,387,241 A | 2/1995 | Hayes | 5,645,604 A | 7/1997 | Schneider et al. |
| 5,397,360 A | 3/1995 | Cohen et al. | 5,653,765 A | 8/1997 | McTighe et al. |
| 5,405,392 A | 4/1995 | Deckner et al. | 5,658,294 A | 8/1997 | Sederholm |
| 5,405,395 A | 4/1995 | Coates | 5,658,344 A | 8/1997 | Hurlburt |
| 5,405,400 A | 4/1995 | Linscheid et al. | 5,658,346 A | 8/1997 | Willi et al. |
| 5,405,401 A | 4/1995 | Lippincott, III et al. | 5,658,348 A | 8/1997 | Rohr, Jr. |
| 5,405,403 A | 4/1995 | Mikhail | 5,658,349 A | 8/1997 | Brooks et al. |
| 5,405,404 A | 4/1995 | Gardner et al. | 5,662,656 A | 9/1997 | White |
| 5,411,555 A | 5/1995 | Nieder | 5,676,700 A | 10/1997 | Black et al. |
| 5,413,605 A | 5/1995 | Ashby et al. | 5,676,704 A | 10/1997 | Ries et al. |
| 5,413,607 A | 5/1995 | Engelbrecht et al. | 5,681,354 A | 10/1997 | Eckhoff |
| 5,413,610 A | 5/1995 | Amino et al. | 5,683,399 A | 11/1997 | Jones |
| 5,417,696 A | 5/1995 | Kashuba et al. | 5,683,472 A | 11/1997 | O'Neil et al. |
| 5,425,778 A | 6/1995 | Zichner et al. | 5,702,463 A | 12/1997 | Pothier et al. |
| 5,425,779 A | 6/1995 | Schlosser et al. | 5,702,475 A | 12/1997 | Zahedi et al. |
| 5,431,657 A | 7/1995 | Rohr | 5,702,476 A | 12/1997 | Limacher et al. |
| 5,443,512 A | 8/1995 | Parr et al. | 5,702,477 A | 12/1997 | Capello et al. |
| 5,443,516 A | 8/1995 | Albrektsson et al. | 5,702,478 A | 12/1997 | Tornier et al. |
| 5,447,492 A | 9/1995 | Cartmell et al. | 5,702,482 A | 12/1997 | Thongpreda et al. |
| 5,458,637 A | 10/1995 | Hayes | 5,702,487 A | 12/1997 | Averill et al. |
| 5,462,563 A | 10/1995 | Shearer et al. | 5,720,752 A | 2/1998 | Elliott et al. |
| 5,474,560 A | 12/1995 | Rohr, Jr. | 5,725,589 A | 3/1998 | Pfaff et al. |
| 5,480,443 A | 1/1996 | Elias | 5,725,591 A | 3/1998 | DeCarlo, Jr. et al. |
| 5,480,444 A | 1/1996 | Incavo et al. | 5,725,597 A | 3/1998 | Hwang |
| 5,480,445 A | 1/1996 | Burkinshaw | 5,735,901 A | 4/1998 | Maumy et al. |
| 5,480,446 A | 1/1996 | Goodfellow et al. | 5,746,771 A | 5/1998 | Clement, Jr. et al. |
| 5,480,447 A | 1/1996 | Skiba | 5,749,877 A | 5/1998 | Young et al. |
| 5,480,448 A | 1/1996 | Mikhail | 5,755,794 A | 5/1998 | Benson |

| Patent No. | Date | Inventor |
|---|---|---|
| 5,755,800 A | 5/1998 | O'Neil et al. |
| 5,755,805 A | 5/1998 | Whiteside |
| 5,755,806 A | 5/1998 | Stalcup et al. |
| 5,755,807 A | 5/1998 | Anstaett et al. |
| 5,755,808 A | 5/1998 | DeCarlo et al. |
| 5,766,255 A * | 6/1998 | Slamin et al. ............ 623/20.15 |
| 5,766,256 A | 6/1998 | Oudard et al. |
| 5,766,260 A | 6/1998 | Whiteside |
| 5,766,262 A | 6/1998 | Mikhail |
| 5,776,200 A | 7/1998 | Johnson et al. |
| 5,776,201 A | 7/1998 | Colleran et al. |
| 5,776,202 A | 7/1998 | Copf et al. |
| 5,782,920 A | 7/1998 | Colleran |
| 5,782,921 A | 7/1998 | Colleran et al. |
| 5,782,924 A | 7/1998 | Johnson |
| 5,782,925 A | 7/1998 | Collazo et al. |
| 5,782,928 A | 7/1998 | Ries et al. |
| 5,782,930 A | 7/1998 | Lin et al. |
| 5,788,976 A | 8/1998 | Bradford |
| 5,798,924 A | 8/1998 | Eufinger et al. |
| 5,800,554 A | 9/1998 | Scholz et al. |
| 5,800,555 A | 9/1998 | Gray, III |
| 5,800,556 A | 9/1998 | Sanders et al. |
| 5,800,558 A | 9/1998 | LaHaise, Sr. |
| 5,800,560 A | 9/1998 | Draenert et al. |
| 5,817,096 A | 10/1998 | Salyer |
| 5,824,097 A | 10/1998 | Gabriel et al. |
| 5,824,107 A | 10/1998 | Tschirren et al. |
| 5,824,108 A | 10/1998 | Huebner |
| 5,830,215 A | 11/1998 | Incavo et al. |
| 5,858,020 A | 1/1999 | Johnson et al. |
| 5,865,850 A | 2/1999 | Matthews |
| 5,871,547 A | 2/1999 | Abouaf et al. |
| 5,871,548 A | 2/1999 | Sanders et al. |
| 5,876,459 A | 3/1999 | Powell |
| 5,879,387 A | 3/1999 | Jones et al. |
| 5,879,390 A | 3/1999 | Kubein-Meesenburg et al. |
| 5,879,391 A * | 3/1999 | Slamin ................ 623/20.15 |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,406 A | 3/1999 | Lilley |
| 5,888,205 A | 3/1999 | Pratt et al. |
| 5,888,206 A | 3/1999 | Lob et al. |
| 5,888,211 A | 3/1999 | Sanders |
| 5,899,942 A | 5/1999 | Berman |
| 5,902,340 A | 5/1999 | White et al. |
| 5,904,688 A | 5/1999 | Gilbert et al. |
| 5,904,720 A | 5/1999 | Farrar et al. |
| 5,906,644 A | 5/1999 | Powell |
| 5,910,172 A | 6/1999 | Penenberg |
| 5,916,269 A | 6/1999 | Serbousek et al. |
| 5,916,270 A | 6/1999 | Lipman |
| 5,919,236 A | 7/1999 | Pfaff et al. |
| 5,928,286 A | 7/1999 | Ashby et al. |
| 5,928,287 A | 7/1999 | Keller |
| 5,931,870 A | 8/1999 | Cuckler et al. |
| 5,935,171 A | 8/1999 | Schneider et al. |
| 5,935,175 A | 8/1999 | Ostiguy, Jr. et al. |
| 5,938,702 A | 8/1999 | Lopez et al. |
| 5,944,756 A | 8/1999 | Fischetti et al. |
| 5,944,759 A | 8/1999 | Link |
| 5,951,603 A | 9/1999 | O'Neil et al. |
| 5,954,727 A | 9/1999 | Collazo |
| 5,957,979 A | 9/1999 | Beckman et al. |
| 5,961,516 A | 10/1999 | Graf et al. |
| 5,972,368 A | 10/1999 | McKay |
| 5,973,222 A | 10/1999 | Devanathan et al. |
| 5,976,148 A | 11/1999 | Charpenet et al. |
| 5,976,188 A | 11/1999 | Dextradeur et al. |
| 5,976,189 A | 11/1999 | Keller et al. |
| 5,977,204 A | 11/1999 | Boyan et al. |
| 5,980,574 A | 11/1999 | Takei et al. |
| 5,984,968 A | 11/1999 | Park |
| 5,984,969 A | 11/1999 | Matthews et al. |
| 5,989,293 A | 11/1999 | Cook et al. |
| 5,989,294 A | 11/1999 | Marlow et al. |
| 5,997,576 A | 12/1999 | Copf et al. |
| 5,997,577 A | 12/1999 | Herrington et al. |
| 5,997,579 A | 12/1999 | Albrektsson et al. |
| 6,004,353 A | 12/1999 | Masini |
| 6,005,018 A | 12/1999 | Cicierega et al. |
| 6,007,580 A | 12/1999 | Lehto et al. |
| 6,008,432 A | 12/1999 | Taylor |
| 6,010,533 A | 1/2000 | Pope et al. |
| 6,010,534 A | 1/2000 | O'Neil et al. |
| 6,013,080 A | 1/2000 | Khalili |
| 6,013,081 A | 1/2000 | Burkinshaw et al. |
| 6,013,103 A | 1/2000 | Kaufman et al. |
| 6,013,104 A | 1/2000 | Kampner |
| 6,015,937 A | 1/2000 | Branemark et al. |
| 6,027,505 A | 2/2000 | Peter et al. |
| 6,039,764 A | 3/2000 | Pottenger et al. |
| 6,042,611 A | 3/2000 | Noiles |
| 6,045,583 A | 4/2000 | Gross et al. |
| 6,053,945 A | 4/2000 | O'Neil et al. |
| 6,056,779 A | 5/2000 | Noyer et al. |
| 6,059,833 A | 5/2000 | Doets et al. |
| 6,063,091 A | 5/2000 | Lombardo et al. |
| 6,063,124 A | 5/2000 | Amstutz |
| 6,066,176 A | 5/2000 | Oshida |
| 6,071,311 A | 6/2000 | O'Neil et al. |
| 6,074,424 A | 6/2000 | Perrone, Jr. et al. |
| 6,074,425 A | 6/2000 | Pappas |
| 6,080,195 A | 6/2000 | Colleran et al. |
| 6,086,614 A | 7/2000 | Mumme |
| 6,087,553 A | 7/2000 | Cohen et al. |
| 6,090,146 A | 7/2000 | Rozow, III et al. |
| 6,093,208 A | 7/2000 | Tian et al. |
| 6,096,082 A | 8/2000 | Stegmuller et al. |
| 6,099,569 A | 8/2000 | Keller et al. |
| 6,099,571 A | 8/2000 | Knapp |
| 6,113,640 A | 9/2000 | Tormala et al. |
| 6,117,175 A | 9/2000 | Bosredon et al. |
| 6,120,543 A | 9/2000 | Kubein-Meesenburg et al. |
| 6,120,545 A | 9/2000 | Hamelijnck et al. |
| 6,126,690 A | 10/2000 | Ateshian et al. |
| 6,126,691 A | 10/2000 | Kasra et al. |
| 6,126,692 A | 10/2000 | Robie et al. |
| 6,126,693 A | 10/2000 | O'Neil et al. |
| 6,126,694 A | 10/2000 | Gray, Jr. |
| 6,126,695 A | 10/2000 | Semlitsch et al. |
| 6,129,765 A | 10/2000 | Lopez et al. |
| 6,132,468 A | 10/2000 | Mansmann |
| 6,132,469 A | 10/2000 | Schroeder |
| 6,136,029 A | 10/2000 | Johnson et al. |
| 6,136,033 A | 10/2000 | Suemer et al. |
| 6,136,035 A | 10/2000 | Lob et al. |
| 6,139,584 A | 10/2000 | Ochoa et al. |
| 6,142,998 A | 11/2000 | Smith et al. |
| 6,146,424 A | 11/2000 | Gray, Jr. et al. |
| 6,149,687 A | 11/2000 | Gray, Jr. et al. |
| 6,152,930 A | 11/2000 | Mastrorio |
| 6,152,961 A | 11/2000 | Ostiguy, Jr. et al. |
| 6,156,070 A | 12/2000 | Incavo et al. |
| 6,162,255 A | 12/2000 | Oyola |
| 6,162,256 A | 12/2000 | Ostiguy, Jr. et al. |
| 6,165,220 A | 12/2000 | McKellop et al. |
| 6,165,222 A | 12/2000 | Hoeppner et al. |
| 6,165,223 A | 12/2000 | Metzger et al. |
| 6,168,600 B1 | 1/2001 | Grace et al. |
| 6,171,342 B1 | 1/2001 | O'Neil et al. |
| 6,179,876 B1 | 1/2001 | Stamper et al. |
| 6,179,877 B1 | 1/2001 | Burke |
| 6,193,759 B1 | 2/2001 | Ro et al. |
| 6,197,032 B1 | 3/2001 | Lawes et al. |
| 6,200,324 B1 | 3/2001 | Regni, Jr. |
| 6,206,929 B1 | 3/2001 | Ochoa et al. |
| 6,214,014 B1 | 4/2001 | McGann |
| 6,214,052 B1 | 4/2001 | Burkinshaw |
| 6,214,053 B1 | 4/2001 | Ling et al. |
| 6,217,615 B1 | 4/2001 | Sioshansi et al. |
| 6,217,619 B1 | 4/2001 | Keller et al. |
| 6,221,110 B1 | 4/2001 | Copf et al. |
| 6,224,633 B1 | 5/2001 | Kalberer et al. |
| 6,228,091 B1 | 5/2001 | Lombardo et al. |

| | | |
|---|---|---|
| 6,228,121 B1 | 5/2001 | Khalili |
| 6,231,611 B1 | 5/2001 | Mosseri |
| 6,235,060 B1 | 5/2001 | Kubein-Meesenburg et al. |
| 6,245,111 B1 | 6/2001 | Shaffner |
| 6,248,132 B1 | 6/2001 | Harris |
| 6,264,698 B1 | 7/2001 | Lawes et al. |
| 6,264,699 B1 | 7/2001 | Noiles et al. |
| 6,267,785 B1 | 7/2001 | Masini |
| 6,281,264 B1 | 8/2001 | Salovey et al. |
| 6,284,001 B1 | 9/2001 | Knapp |
| 6,290,725 B1 | 9/2001 | Weiss et al. |
| 6,290,726 B1 | 9/2001 | Pope et al. |
| 6,290,727 B1 | 9/2001 | Otto et al. |
| 6,293,971 B1 | 9/2001 | Nelson et al. |
| 6,296,667 B1 | 10/2001 | Johnson et al. |
| 6,302,890 B1 | 10/2001 | Leone, Jr. |
| 6,306,172 B1 | 10/2001 | O'Neil et al. |
| 6,319,285 B1 | 11/2001 | Chamier et al. |
| 6,325,829 B1 | 12/2001 | Schmotzer et al. |
| 6,334,875 B1 | 1/2002 | Keller et al. |
| 6,340,370 B1 | 1/2002 | Willert et al. |
| 6,342,075 B1 | 1/2002 | MacArthur |
| 6,344,060 B1 | 2/2002 | Schmotzer et al. |
| 6,344,496 B1 | 2/2002 | Niederauer et al. |
| 6,352,559 B1 | 3/2002 | Church et al. |
| 6,358,282 B1 | 3/2002 | Wymann et al. |
| 6,361,566 B1 | 3/2002 | Al-Hafez et al. |
| 6,368,354 B2 | 4/2002 | Burstein et al. |
| 6,376,573 B1 | 4/2002 | White et al. |
| 6,379,389 B1 | 4/2002 | Koch et al. |
| 6,383,227 B1 | 5/2002 | Baroud et al. |
| 6,387,131 B1 | 5/2002 | Miehlke et al. |
| 6,391,251 B1 | 5/2002 | Keicher et al. |
| 6,413,279 B1 | 7/2002 | Metzger et al. |
| 6,413,280 B1 | 7/2002 | Feiler |
| 6,416,552 B1 | 7/2002 | Hoeppner et al. |
| 6,423,096 B1 | 7/2002 | Musset et al. |
| 6,425,921 B1 | 7/2002 | Grundei et al. |
| 6,428,578 B2 | 8/2002 | White |
| 6,432,141 B1 | 8/2002 | Stocks et al. |
| 6,436,145 B1 | 8/2002 | Miller |
| 6,436,146 B1 | 8/2002 | Hassler et al. |
| 6,447,549 B1 | 9/2002 | Taft |
| 6,447,550 B1 | 9/2002 | Hunter et al. |
| 6,451,058 B2 | 9/2002 | Tuke et al. |
| 6,468,281 B1 | 10/2002 | Badorf et al. |
| 6,475,243 B1 | 11/2002 | Sheldon et al. |
| 6,482,237 B2 | 11/2002 | Mosseri et al. |
| 6,485,519 B2 * | 11/2002 | Meyers et al. ............. 623/20.24 |
| 6,488,713 B1 | 12/2002 | Hershberger |
| 6,488,715 B1 | 12/2002 | Pope et al. |
| 6,491,726 B2 | 12/2002 | Pappas |
| 6,494,914 B2 | 12/2002 | Brown et al. |
| 6,497,728 B2 | 12/2002 | Yong et al. |
| 6,500,207 B1 | 12/2002 | Keller |
| 6,500,208 B1 | 12/2002 | Metzger et al. |
| 6,503,281 B1 | 1/2003 | Mallory |
| 6,506,215 B1 | 1/2003 | Letot et al. |
| 6,517,583 B1 | 2/2003 | Pope et al. |
| 6,518,328 B2 | 2/2003 | Kumar |
| 6,520,995 B2 | 2/2003 | Church et al. |
| 6,524,344 B2 | 2/2003 | Yoon et al. |
| 6,524,345 B1 | 2/2003 | Valimaa et al. |
| 6,527,807 B1 | 3/2003 | O'Neil et al. |
| 6,527,808 B1 | 3/2003 | Albertorio et al. |
| 6,527,809 B1 | 3/2003 | Doursounian et al. |
| 6,527,810 B2 | 3/2003 | Johnson et al. |
| 6,537,321 B1 | 3/2003 | Horber et al. |
| 6,540,786 B2 | 4/2003 | Chibrac et al. |
| 6,558,427 B2 | 5/2003 | Leclercq et al. |
| 6,565,575 B2 | 5/2003 | Lewis |
| 6,565,606 B1 | 5/2003 | Bruce et al. |
| 6,589,248 B1 | 7/2003 | Hughes |
| 6,589,283 B1 | 7/2003 | Metzger et al. |
| 6,589,284 B1 | 7/2003 | Silberer et al. |
| 6,602,259 B1 | 8/2003 | Masini |
| 6,605,293 B1 | 8/2003 | Giordano et al. |
| 6,610,097 B2 | 8/2003 | Serbousek et al. |
| 6,613,092 B1 | 9/2003 | Kana et al. |
| 6,616,696 B1 | 9/2003 | Merchant |
| 6,620,198 B2 | 9/2003 | Burstein et al. |
| 6,623,488 B1 | 9/2003 | Leone, Jr. |
| 6,626,950 B2 | 9/2003 | Brown et al. |
| 6,629,999 B1 | 10/2003 | Serafin, Jr. |
| 6,641,617 B1 | 11/2003 | Merrill et al. |
| 6,652,533 B2 | 11/2003 | O'Neil |
| 6,652,586 B2 | 11/2003 | Hunter et al. |
| 6,652,589 B2 | 11/2003 | Schmotzer et al. |
| 6,652,590 B1 | 11/2003 | Zitnansky et al. |
| 6,660,040 B2 | 12/2003 | Chan et al. |
| 6,669,728 B2 | 12/2003 | Despres, III et al. |
| 6,679,890 B2 | 1/2004 | Margulies et al. |
| 6,682,566 B2 | 1/2004 | Draenert et al. |
| 6,682,567 B1 | 1/2004 | Schroeder |
| 6,682,568 B2 | 1/2004 | Despres, III et al. |
| 6,692,531 B1 | 2/2004 | Yoon et al. |
| 6,699,293 B2 | 3/2004 | White |
| 6,706,071 B1 | 3/2004 | Wolter et al. |
| 6,706,072 B2 | 3/2004 | Dwyer et al. |
| 6,712,857 B1 | 3/2004 | Roger et al. |
| 6,712,858 B1 | 3/2004 | Grundei et al. |
| 6,716,248 B2 | 4/2004 | Huene |
| 6,719,800 B2 | 4/2004 | Meyers et al. |
| 6,723,129 B2 | 4/2004 | Dwyer et al. |
| 6,726,725 B2 | 4/2004 | Hunter et al. |
| 6,740,092 B2 | 5/2004 | Lombardo et al. |
| 6,743,258 B1 | 6/2004 | Keller et al. |
| 6,755,864 B1 | 6/2004 | Brack et al. |
| 6,758,864 B2 | 7/2004 | Storer et al. |
| 6,761,741 B2 | 7/2004 | Iesaka |
| 6,764,516 B2 | 7/2004 | Pappas |
| 6,770,097 B2 | 8/2004 | Leclercq et al. |
| 6,773,461 B2 | 8/2004 | Meyers et al. |
| 6,783,550 B2 | 8/2004 | MacArthur |
| 6,786,933 B2 | 9/2004 | Merrill et al. |
| 6,793,681 B1 | 9/2004 | Pope et al. |
| 6,800,670 B2 | 10/2004 | Shen et al. |
| 6,802,866 B2 | 10/2004 | Bunz et al. |
| 6,811,568 B2 | 11/2004 | Minamikawa |
| 6,811,569 B1 | 11/2004 | Afriat et al. |
| 6,818,019 B2 | 11/2004 | Horber et al. |
| 6,818,020 B2 | 11/2004 | Sun et al. |
| 6,827,739 B2 | 12/2004 | Griner et al. |
| 6,827,742 B2 | 12/2004 | Hayes, Jr. et al. |
| 6,840,944 B2 | 1/2005 | Suddaby |
| 6,843,805 B2 | 1/2005 | Webb et al. |
| 6,843,806 B2 | 1/2005 | Hayes, Jr. et al. |
| 6,863,692 B2 | 3/2005 | Meulink |
| 6,866,683 B2 | 3/2005 | Gerbec et al. |
| 6,866,685 B2 | 3/2005 | Chan et al. |
| 6,869,447 B2 | 3/2005 | Lee et al. |
| 6,875,237 B2 | 4/2005 | Dye |
| 6,881,229 B2 | 4/2005 | Khandkar et al. |
| 6,887,276 B2 | 5/2005 | Gerbec et al. |
| 6,896,702 B2 | 5/2005 | Collazo |
| 6,905,515 B1 | 6/2005 | Gilbertson |
| 6,908,486 B2 | 6/2005 | Lewallen |
| 6,916,340 B2 | 7/2005 | Metzger et al. |
| 6,916,341 B2 | 7/2005 | Rolston |
| 6,923,833 B2 | 8/2005 | Wasielewski |
| 6,926,738 B2 | 8/2005 | Wyss |
| 6,926,739 B1 | 8/2005 | O'Connor et al. |
| 6,926,740 B2 | 8/2005 | Lewis et al. |
| 6,944,518 B2 | 9/2005 | Roose |
| 6,953,479 B2 | 10/2005 | Carson et al. |
| 6,962,607 B2 | 11/2005 | Gundlapalli et al. |
| 6,966,932 B1 | 11/2005 | Schroeder |
| 6,969,406 B2 | 11/2005 | Tornier et al. |
| 6,972,021 B2 | 12/2005 | Raugel et al. |
| 6,972,039 B2 | 12/2005 | Metzger et al. |
| 6,981,991 B2 | 1/2006 | Ferree |
| 6,986,791 B1 | 1/2006 | Metzger |
| 7,004,946 B2 | 2/2006 | Parker et al. |
| 7,022,142 B2 | 4/2006 | Johnson |
| 7,025,788 B2 | 4/2006 | Metzger et al. |
| 7,037,310 B2 | 5/2006 | Murphy |
| 7,044,974 B2 | 5/2006 | Garber et al. |
| 7,051,417 B2 | 5/2006 | Michelson |

| | | |
|---|---|---|
| 7,056,577 B1 | 6/2006 | Bruce et al. |
| 7,070,622 B1 | 7/2006 | Brown et al. |
| 7,074,241 B2 | 7/2006 | McKinnon |
| 7,105,026 B2 | 9/2006 | Johnson et al. |
| 7,108,719 B2 | 9/2006 | Horber et al. |
| 7,125,193 B2 | 10/2006 | Despres, III et al. |
| 7,131,995 B2 | 11/2006 | Biedermann et al. |
| 7,153,326 B1 | 12/2006 | Metzger |
| 7,156,880 B2 | 1/2007 | Evans et al. |
| 7,166,133 B2 | 1/2007 | Evans et al. |
| 7,179,295 B2 | 2/2007 | Kovacevic |
| 7,189,263 B2 | 3/2007 | Erbe et al. |
| 7,192,448 B2 | 3/2007 | Ferree |
| 7,198,642 B2 | 4/2007 | Hazebrouck et al. |
| 7,445,639 B2 | 11/2008 | Metzger et al. |
| 7,497,874 B1 | 3/2009 | Metzger et al. |
| 2001/0014828 A1 | 8/2001 | Yoon |
| 2001/0014829 A1 | 8/2001 | Yoon |
| 2001/0016780 A1 | 8/2001 | Yong San |
| 2001/0018616 A1 | 8/2001 | Schwab |
| 2001/0032021 A1 | 10/2001 | McKinnon |
| 2001/0037156 A1 | 11/2001 | Burstein et al. |
| 2001/0039456 A1 | 11/2001 | Boyer et al. |
| 2001/0039457 A1 | 11/2001 | Boyer et al. |
| 2001/0041941 A1 | 11/2001 | Boyer et al. |
| 2001/0051830 A1 | 12/2001 | Tuke et al. |
| 2002/0007294 A1 | 1/2002 | Bradbury et al. |
| 2002/0022889 A1 | 2/2002 | Chibrac et al. |
| 2002/0022890 A1 | 2/2002 | Jacobsson et al. |
| 2002/0040244 A1 | 4/2002 | Despres et al. |
| 2002/0040245 A1 | 4/2002 | Lester et al. |
| 2002/0042656 A1 | 4/2002 | Hunter et al. |
| 2002/0045949 A1 | 4/2002 | Ling et al. |
| 2002/0049500 A1 | 4/2002 | Draenert |
| 2002/0052659 A1 | 5/2002 | Hayes et al. |
| 2002/0059000 A1 | 5/2002 | Dwyer et al. |
| 2002/0068980 A1 | 6/2002 | Serbousek et al. |
| 2002/0072799 A1 | 6/2002 | Despres et al. |
| 2002/0082706 A1 | 6/2002 | Raugel |
| 2002/0107577 A1 | 8/2002 | Storer et al. |
| 2002/0116007 A1 | 8/2002 | Lewis |
| 2002/0116068 A1 | 8/2002 | McLean |
| 2002/0120340 A1 | 8/2002 | Metzger et al. |
| 2002/0120341 A1 | 8/2002 | Stumpo et al. |
| 2002/0128653 A1 | 9/2002 | Haidukewych |
| 2002/0138148 A1 | 9/2002 | Hyde |
| 2002/0138151 A1 | 9/2002 | Hubbard et al. |
| 2002/0139818 A1 | 10/2002 | McGuffey |
| 2002/0143402 A1 | 10/2002 | Steinberg |
| 2002/0143403 A1 | 10/2002 | Vaidyanathan et al. |
| 2002/0151978 A1 | 10/2002 | Zacouto et al. |
| 2002/0156536 A1 | 10/2002 | Harris et al. |
| 2002/0165615 A1 | 11/2002 | Abouaf et al. |
| 2002/0173853 A1 | 11/2002 | Corl et al. |
| 2003/0009232 A1 | 1/2003 | Metzger et al. |
| 2003/0009234 A1 | 1/2003 | Treacy et al. |
| 2003/0014120 A1 | 1/2003 | Carson et al. |
| 2003/0022069 A1 | 1/2003 | Karube et al. |
| 2003/0033018 A1 | 2/2003 | Merchant |
| 2003/0040805 A1 | 2/2003 | Minamikawa |
| 2003/0050645 A1 | 3/2003 | Parker et al. |
| 2003/0050703 A1 | 3/2003 | Harris et al. |
| 2003/0050705 A1 | 3/2003 | Cueille et al. |
| 2003/0055508 A1 | 3/2003 | Metzger et al. |
| 2003/0055509 A1 | 3/2003 | McCue et al. |
| 2003/0060889 A1 | 3/2003 | Tarabishy |
| 2003/0060890 A1 | 3/2003 | Tarabishy |
| 2003/0065397 A1 | 4/2003 | Hanssen et al. |
| 2003/0074078 A1 | 4/2003 | Doubler et al. |
| 2003/0093156 A1 | 5/2003 | Metzger et al. |
| 2003/0105529 A1 | 6/2003 | Synder et al. |
| 2003/0109933 A1 | 6/2003 | Weissman et al. |
| 2003/0114934 A1 | 6/2003 | Steinberg |
| 2003/0114935 A1 | 6/2003 | Chan et al. |
| 2003/0120346 A1 | 6/2003 | Mercinek et al. |
| 2003/0120347 A1 | 6/2003 | Steinberg |
| 2003/0125810 A1 | 7/2003 | Sullivan et al. |
| 2003/0130740 A1 | 7/2003 | Stocks et al. |
| 2003/0139818 A1 | 7/2003 | Rogers et al. |
| 2003/0149485 A1 | 8/2003 | Tornier |
| 2003/0153981 A1 | 8/2003 | Wang et al. |
| 2003/0153982 A1 | 8/2003 | Pria |
| 2003/0158606 A1 | 8/2003 | Coon et al. |
| 2003/0163202 A1 | 8/2003 | Lakin |
| 2003/0171815 A1* | 9/2003 | Kana et al. ............... 623/20.15 |
| 2003/0171817 A1 | 9/2003 | Rambert et al. |
| 2003/0181984 A1 | 9/2003 | Abendschein |
| 2003/0181987 A1 | 9/2003 | Muirhead-Allwood |
| 2003/0204262 A1 | 10/2003 | Ferguson et al. |
| 2003/0204263 A1 | 10/2003 | Justin et al. |
| 2003/0204268 A1 | 10/2003 | Gerbec et al. |
| 2003/0204269 A1 | 10/2003 | Gerbec et al. |
| 2003/0208276 A1 | 11/2003 | Berelsman et al. |
| 2003/0212458 A1 | 11/2003 | Harris et al. |
| 2003/0220697 A1 | 11/2003 | Justin et al. |
| 2003/0220699 A1 | 11/2003 | Hunter et al. |
| 2003/0225457 A1 | 12/2003 | Justin et al. |
| 2003/0225458 A1 | 12/2003 | Donkers et al. |
| 2003/0229356 A1 | 12/2003 | Dye |
| 2003/0229398 A1 | 12/2003 | Iesaka |
| 2004/0002766 A1 | 1/2004 | Hunter et al. |
| 2004/0019380 A1 | 1/2004 | Baege et al. |
| 2004/0019382 A1 | 1/2004 | Amirouche et al. |
| 2004/0019386 A1 | 1/2004 | Ferree |
| 2004/0024460 A1 | 2/2004 | Ferree |
| 2004/0030344 A1 | 2/2004 | Dye et al. |
| 2004/0030394 A1 | 2/2004 | Horber |
| 2004/0030400 A1 | 2/2004 | Horber |
| 2004/0034432 A1 | 2/2004 | Hughes et al. |
| 2004/0039449 A1 | 2/2004 | Tornier |
| 2004/0039451 A1 | 2/2004 | Southworth |
| 2004/0049284 A1 | 3/2004 | German et al. |
| 2004/0049285 A1 | 3/2004 | Haas |
| 2004/0049286 A1 | 3/2004 | German et al. |
| 2004/0054418 A1 | 3/2004 | McLean et al. |
| 2004/0059427 A1 | 3/2004 | Serbousek et al. |
| 2004/0068324 A1 | 4/2004 | Grundei |
| 2004/0073226 A1 | 4/2004 | Cotting et al. |
| 2004/0073315 A1 | 4/2004 | Justin et al. |
| 2004/0078083 A1 | 4/2004 | Gibbs et al. |
| 2004/0083004 A1 | 4/2004 | Wasielewski |
| 2004/0098133 A1 | 5/2004 | Carignan et al. |
| 2004/0098134 A1 | 5/2004 | Meulink |
| 2004/0102851 A1 | 5/2004 | Saladino |
| 2004/0102852 A1 | 5/2004 | Johnson et al. |
| 2004/0107594 A1 | 6/2004 | Afriat |
| 2004/0117023 A1 | 6/2004 | Gerbec et al. |
| 2004/0117024 A1 | 6/2004 | Gerbec et al. |
| 2004/0117029 A1 | 6/2004 | Lewis et al. |
| 2004/0122521 A1 | 6/2004 | Lee et al. |
| 2004/0122524 A1 | 6/2004 | Hunter et al. |
| 2004/0143336 A1 | 7/2004 | Burkinshaw |
| 2004/0143341 A1 | 7/2004 | McLean |
| 2004/0147926 A1 | 7/2004 | Iversen |
| 2004/0153063 A1 | 8/2004 | Harris |
| 2004/0162619 A1 | 8/2004 | Blaylock et al. |
| 2004/0162620 A1 | 8/2004 | Wyss |
| 2004/0162621 A1 | 8/2004 | Crofford |
| 2004/0172137 A1 | 9/2004 | Blaylock et al. |
| 2004/0172139 A1 | 9/2004 | Dwyer et al. |
| 2004/0186580 A1 | 9/2004 | Steinmann |
| 2004/0186586 A1 | 9/2004 | Seyer et al. |
| 2004/0193282 A1 | 9/2004 | Hanes |
| 2004/0199257 A1 | 10/2004 | Dooney |
| 2004/0199259 A1 | 10/2004 | Pichon et al. |
| 2004/0204760 A1 | 10/2004 | Fitz et al. |
| 2004/0204767 A1 | 10/2004 | Park et al. |
| 2004/0210316 A1 | 10/2004 | King et al. |
| 2004/0225368 A1 | 11/2004 | Plumet et al. |
| 2004/0225370 A1 | 11/2004 | Cruchet et al. |
| 2004/0225371 A1 | 11/2004 | Roger |
| 2004/0226343 A1 | 11/2004 | Babler et al. |
| 2004/0236428 A1 | 11/2004 | Burkinshaw et al. |
| 2004/0243249 A1 | 12/2004 | Ishihara et al. |
| 2004/0255749 A1 | 12/2004 | Hayden |
| 2004/0260396 A1 | 12/2004 | Ferree et al. |
| 2004/0267374 A1 | 12/2004 | Friedrichs |
| 2004/0267375 A1 | 12/2004 | Friedrichs |

| | | |
|---|---|---|
| 2005/0004677 A1 | 1/2005 | Johnson |
| 2005/0004678 A1 | 1/2005 | Richards |
| 2005/0010288 A1 | 1/2005 | Merrill et al. |
| 2005/0010303 A1 | 1/2005 | Nogier |
| 2005/0010304 A1 | 1/2005 | Jamali |
| 2005/0021149 A1 | 1/2005 | Borruto et al. |
| 2005/0027302 A1 | 2/2005 | Cueille et al. |
| 2005/0033442 A1 | 2/2005 | Fisher et al. |
| 2005/0033445 A1 | 2/2005 | Siebel |
| 2005/0038443 A1 | 2/2005 | Hedley et al. |
| 2005/0043807 A1 | 2/2005 | Wood |
| 2005/0043812 A1 | 2/2005 | Corl et al. |
| 2005/0049524 A1 | 3/2005 | Lefevre et al. |
| 2005/0049713 A1 | 3/2005 | Garber et al. |
| 2005/0055102 A1 | 3/2005 | Tornier et al. |
| 2005/0059972 A1 | 3/2005 | Biscup |
| 2005/0060040 A1 | 3/2005 | Auxepaules et al. |
| 2005/0071014 A1 | 3/2005 | Barnett et al. |
| 2005/0071015 A1 | 3/2005 | Sekel |
| 2005/0075641 A1 | 4/2005 | Singhatat et al. |
| 2005/0080490 A1 | 4/2005 | Bertram |
| 2005/0085823 A1 | 4/2005 | Murphy |
| 2005/0090903 A1 | 4/2005 | Khandkar et al. |
| 2005/0102032 A1 | 5/2005 | Beynnon et al. |
| 2005/0102033 A1 | 5/2005 | Lambert et al. |
| 2005/0102034 A1 | 5/2005 | Hayes et al. |
| 2005/0102038 A1 | 5/2005 | Grundei |
| 2005/0107884 A1 | 5/2005 | Johnson et al. |
| 2005/0119755 A1 | 6/2005 | Kristensen |
| 2005/0125067 A1 | 6/2005 | Sweeney |
| 2005/0131540 A1 | 6/2005 | Trieu |
| 2005/0137603 A1 | 6/2005 | Belew et al. |
| 2005/0137708 A1 | 6/2005 | Clark |
| 2005/0137711 A1 | 6/2005 | Southworth et al. |
| 2005/0143828 A1 | 6/2005 | Collins et al. |
| 2005/0143835 A1 | 6/2005 | Gilbertson |
| 2005/0143836 A1 | 6/2005 | Steinberg |
| 2005/0149043 A1 | 7/2005 | Parry et al. |
| 2005/0149047 A1 | 7/2005 | Parry et al. |
| 2005/0154470 A1* | 7/2005 | Sekel ............ 623/20.15 |
| 2005/0154471 A1 | 7/2005 | Aram et al. |
| 2005/0165490 A1 | 7/2005 | Tornier |
| 2005/0165491 A1 | 7/2005 | Diaz |
| 2005/0165492 A1 | 7/2005 | Fitz |
| 2005/0171612 A1 | 8/2005 | Rolston |
| 2005/0177172 A1 | 8/2005 | Acker et al. |
| 2005/0177242 A1 | 8/2005 | Lotke |
| 2005/0177244 A1 | 8/2005 | Steinberg |
| 2005/0187635 A1* | 8/2005 | Metzger ............ 623/20.15 |
| 2005/0187637 A1 | 8/2005 | Karrer et al. |
| 2005/0192675 A1 | 9/2005 | Robinson |
| 2005/0202371 A1 | 9/2005 | McGuire |
| 2005/0203535 A1 | 9/2005 | Parry et al. |
| 2005/0203629 A1 | 9/2005 | Cipolletti et al. |
| 2005/0209604 A1 | 9/2005 | Penenberg et al. |
| 2005/0211562 A1 | 9/2005 | Rowe et al. |
| 2005/0216091 A1 | 9/2005 | Wasielewski |
| 2005/0228394 A1 | 10/2005 | Bihary et al. |
| 2005/0228395 A1 | 10/2005 | Auxepaules et al. |
| 2005/0228502 A1 | 10/2005 | Deloge et al. |
| 2005/0228503 A1 | 10/2005 | Gundolf |
| 2005/0240275 A1 | 10/2005 | Chappuis |
| 2005/0240276 A1 | 10/2005 | Shea et al. |
| 2005/0246026 A1 | 11/2005 | Lewis et al. |
| 2005/0246027 A1 | 11/2005 | Metzger et al. |
| 2005/0246028 A1 | 11/2005 | Pappas et al. |
| 2005/0246030 A1 | 11/2005 | Yao |
| 2005/0256576 A1 | 11/2005 | Moskowitz et al. |
| 2005/0256584 A1 | 11/2005 | Farrar |
| 2005/0261776 A1 | 11/2005 | Taylor |
| 2005/0267584 A1 | 12/2005 | Burdulis et al. |
| 2005/0267585 A1 | 12/2005 | Sidebotham |
| 2005/0267590 A1 | 12/2005 | Lee |
| 2005/0278034 A1 | 12/2005 | Johnson et al. |
| 2005/0283252 A1 | 12/2005 | Coon et al. |
| 2005/0283253 A1 | 12/2005 | Coon et al. |
| 2005/0283254 A1 | 12/2005 | Hayes et al. |
| 2005/0288791 A1 | 12/2005 | Tornier et al. |
| 2005/0288793 A1 | 12/2005 | Dong et al. |
| 2006/0004463 A1 | 1/2006 | Lewis et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0009857 A1 | 1/2006 | Gibbs et al. |
| 2006/0015188 A1 | 1/2006 | Grimes |
| 2006/0030945 A1 | 2/2006 | Wright |
| 2006/0052876 A1 | 3/2006 | Wozencroft et al. |
| 2006/0058883 A1 | 3/2006 | Aram et al. |
| 2006/0058884 A1 | 3/2006 | Aram et al. |
| 2006/0058886 A1 | 3/2006 | Wozencroft |
| 2006/0064169 A1 | 3/2006 | Ferree |
| 2006/0074491 A1 | 4/2006 | Smith et al. |
| 2006/0085079 A1 | 4/2006 | Carroll |
| 2006/0100714 A1 | 5/2006 | Ensign |
| 2006/0129247 A1 | 6/2006 | Brown et al. |
| 2006/0142865 A1 | 6/2006 | Hyde |
| 2006/0142867 A1 | 6/2006 | Metzger et al. |
| 2006/0149285 A1 | 7/2006 | Burgi et al. |
| 2006/0167462 A1 | 7/2006 | Raugel et al. |
| 2006/0167554 A1 | 7/2006 | Heck et al. |
| 2006/0167556 A1 | 7/2006 | Lazennec et al. |
| 2006/0167557 A1 | 7/2006 | Terrill |
| 2006/0167559 A1 | 7/2006 | Johnstone et al. |
| 2006/0167560 A1 | 7/2006 | Heck et al. |
| 2006/0173547 A1* | 8/2006 | Ensign ............ 623/20.15 |
| 2006/0173548 A1 | 8/2006 | Auxepaules et al. |
| 2006/0178749 A1 | 8/2006 | Pendleton et al. |
| 2006/0178750 A1 | 8/2006 | Chieng |
| 2006/0184249 A1 | 8/2006 | Tarabishy |
| 2006/0190086 A1 | 8/2006 | Clemow et al. |
| 2006/0195196 A1 | 8/2006 | Pendleton et al. |
| 2006/0206210 A1 | 9/2006 | Abicht et al. |
| 2006/0229734 A1 | 10/2006 | Yoon |
| 2006/0235538 A1 | 10/2006 | Rochetin et al. |
| 2006/0241776 A1 | 10/2006 | Brown et al. |
| 2006/0241781 A1 | 10/2006 | Brown et al. |
| 2006/0265079 A1 | 11/2006 | D'Alessio |
| 2007/0010890 A1 | 1/2007 | Collazo |
| 2007/0021838 A1 | 1/2007 | Dugas et al. |
| 2007/0088443 A1 | 4/2007 | Hanssen et al. |
| 2007/0129809 A1 | 6/2007 | Meridew et al. |
| 2007/0173948 A1 | 7/2007 | Meridew et al. |
| 2007/0196230 A1 | 8/2007 | Hamman et al. |
| 2009/0062806 A1 | 3/2009 | Scott et al. |
| 2009/0125114 A1 | 5/2009 | May et al. |
| 2009/0149964 A1 | 6/2009 | May et al. |
| 2009/0299482 A1 | 12/2009 | Metzger et al. |
| 2010/0174378 A1 | 7/2010 | Metzger et al. |

FOREIGN PATENT DOCUMENTS

| | | |
|---|---|---|
| EP | 0000549 A1 | 2/1979 |
| EP | 0378928 | 7/1990 |
| EP | 0538987 A1 | 4/1993 |
| EP | 0555003 | 8/1993 |
| EP | 0689796 | 1/1996 |
| EP | 0797417 A1 | 10/1997 |
| EP | 853930 | 7/1998 |
| EP | 0947181 | 10/1999 |
| EP | 0985386 A2 | 3/2000 |
| EP | 993813 | 4/2000 |
| EP | 01004283 A2 | 5/2000 |
| EP | 1398007 A2 | 3/2004 |
| EP | 1430856 A1 | 6/2004 |
| FR | 2718953 | 10/1995 |
| FR | 2793677 | 11/2000 |
| GB | 1553836 A | 10/1979 |
| GB | 2223172 A | 4/1990 |
| JP | 58141847 | 8/1983 |
| WO | WO-9613233 A1 | 5/1996 |
| WO | WO-0038598 | 7/2000 |
| WO | WO-0205732 | 1/2002 |
| WO | WO-03065939 | 8/2003 |
| WO | WO-2004078069 A2 | 9/2004 |
| WO | WO-2004080340 | 9/2004 |

OTHER PUBLICATIONS

International Search Report and Written Opinion for PCT/US2008/079545 mailed Jan. 14, 2009 claiming priority to U.S. Appl. No. 60/978,949, filed Oct. 10, 2007.
International Search Report and Written Opinion for PCT/US2008/000374 mailed Jun. 6, 2008.
"Advantim® Total Knee System," brochure,1996 (pp. 1-14) Wright Medical Technology, Inc.
"AGC Total Knee System, Tradition™ Series," brochure, (11 pages) 1995. Biomet Orthopedics, Inc.
"Ascent™ Total Knee System, Revision Surgical Technique," (pp. 1-24) 2001. Biomet Orthopedics, Inc.
"FINN® Knee System Modularity and Surgical Latitude, Product Ordering Information," catalog, (4 pages) 1994. Biomet, Inc.
"FINN® Knee System Modularity and Surgical Latitude," brochure (pp. 1-20) 1995 Biomet, Inc.
"FINN® Knee System Modularity and Surgical Latitude," brochure, (11 pages) 1990. Biomet, Inc.
"Kinemax® Plus Total Stabiliser (TS) Revision Surgical technique, Xcelerate Instrumentation," brochure/catalog. Stryker Howmedica Osteonics (Dated at least as early as Apr. 4, 2005.).
"OSS™ Orthopaedic Salvage System, Femoral/Tibial Augmentation," brochure, pp. 1-9. 2003, 2004 Biomet Orthopedics, Inc.
"Passport™ Revision Instrumentation, Howmedica Osteonics Total Knee Revision System Surgical Protocol," brochure, Jun. 2000 (pp. 1-27) Stryer® Howmedica Osteonics.
"S-Rom Total Hip System Surgical Technique," (19 pages) located at http://www.rpa.spot.pt/Main-Sections/Informacao-ao-Profissional-de-Saude.aspx?lang=en-GB, web site copyrighted 2008; accessed Oct. 13, 2010. DePuy.
"S-Rom Total Hip System Surgical Technique," brochure (17 pages) 2000. DePuy Orthopaedics, Inc.
"The RHK™ System, RHK™ controlled rotation," brochure (2 sheets) 2004. ArCom™. Biomet Europe.
"Vanguard Complete Knee System, Cruciate Retaining," brochure (6 pages) 2007. Biomet Orthopedics, Inc.
"Vanguard Complete Knee System, System Summary," brochure, (4 sheets) 2007. Biomet Orthopedics, Inc.
International Preliminary Report on Patentability and Written Opinion issued Jul. 14, 2009 for PCT/US2008/000374 claiming benefit of U.S. Appl. No. 60/879,733, filed Jan. 10, 2007; and U.S. Appl. No. 60/978,949, filed Oct. 10, 2007.
International Preliminary Report on Patentability for PCT/US2008/079545 issued Apr. 13, 2010, claiming priority to U.S. Appl. No. 60/978,949, filed Oct. 10, 2007.
International Search Report and Written Opinion mailed Jan. 25, 2011 for PCT/US2010/044395 Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.
Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.

* cited by examiner

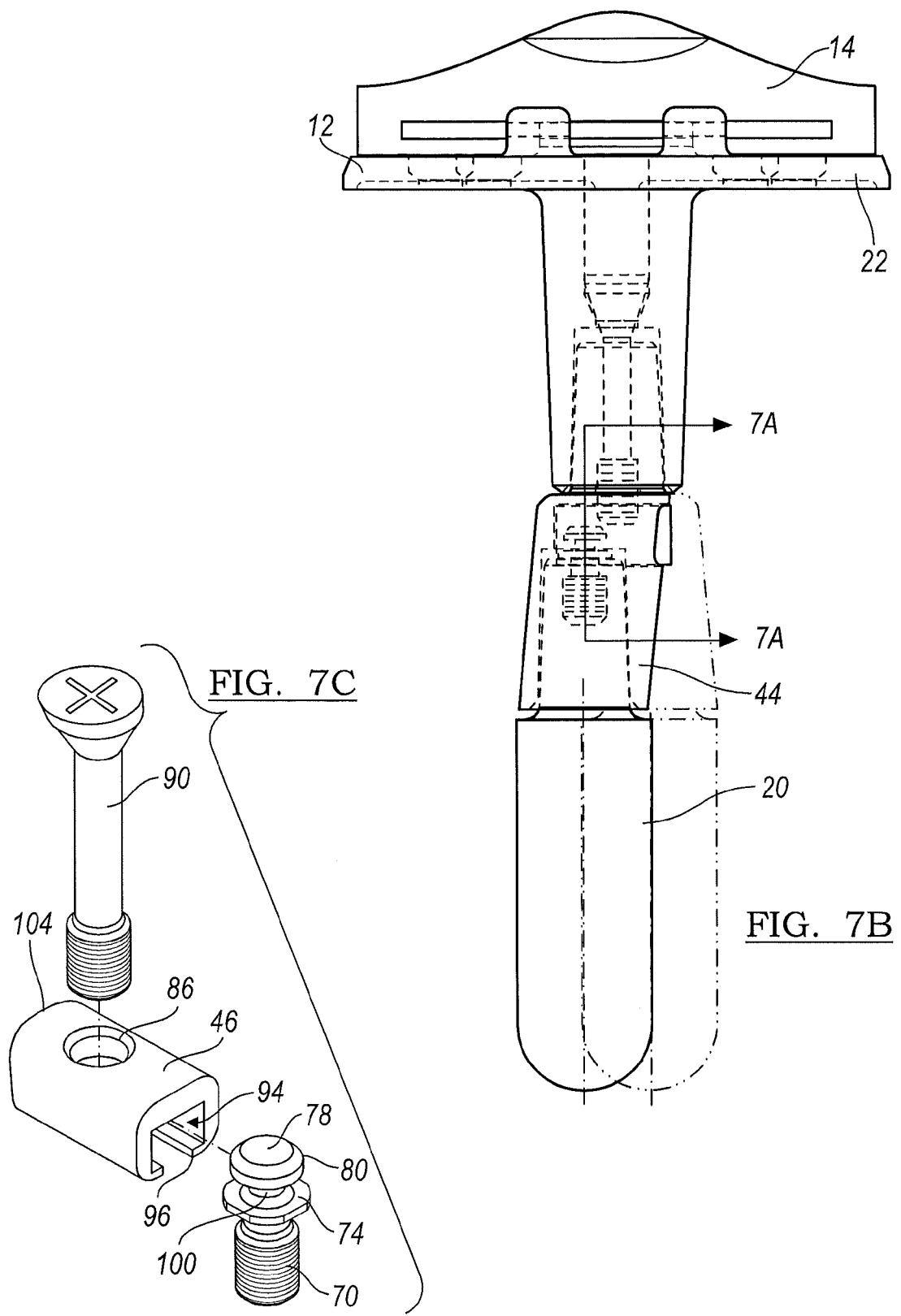

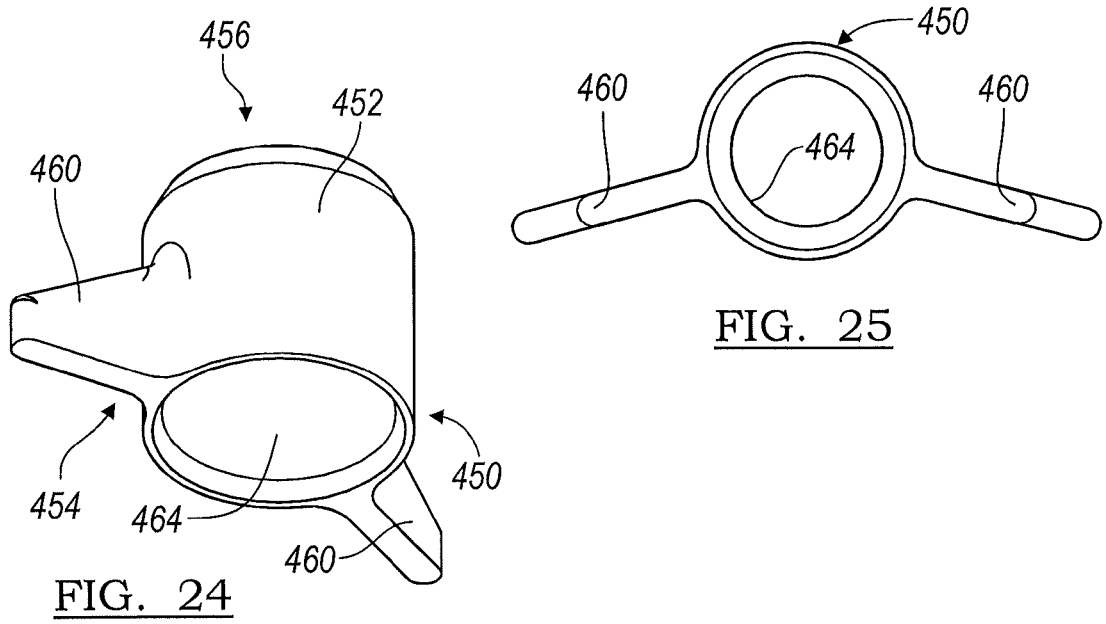
FIG. 24
FIG. 25
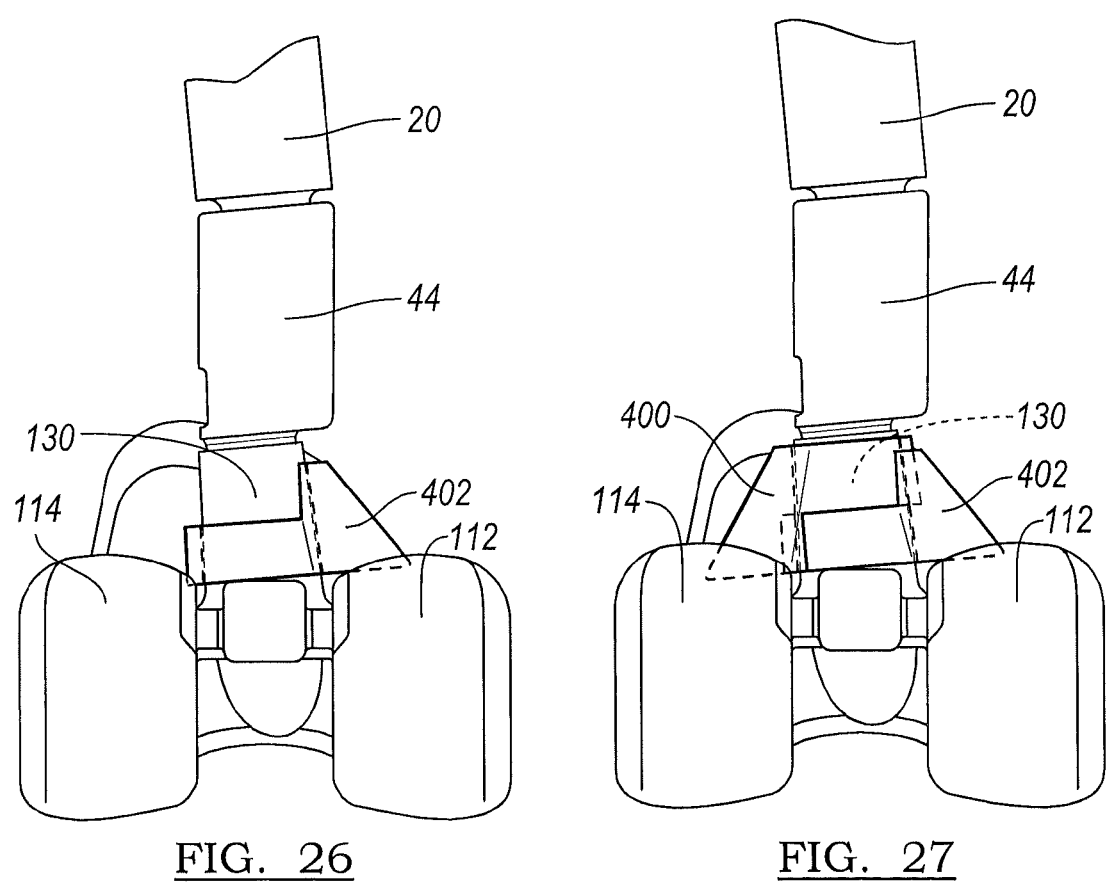
FIG. 26
FIG. 27

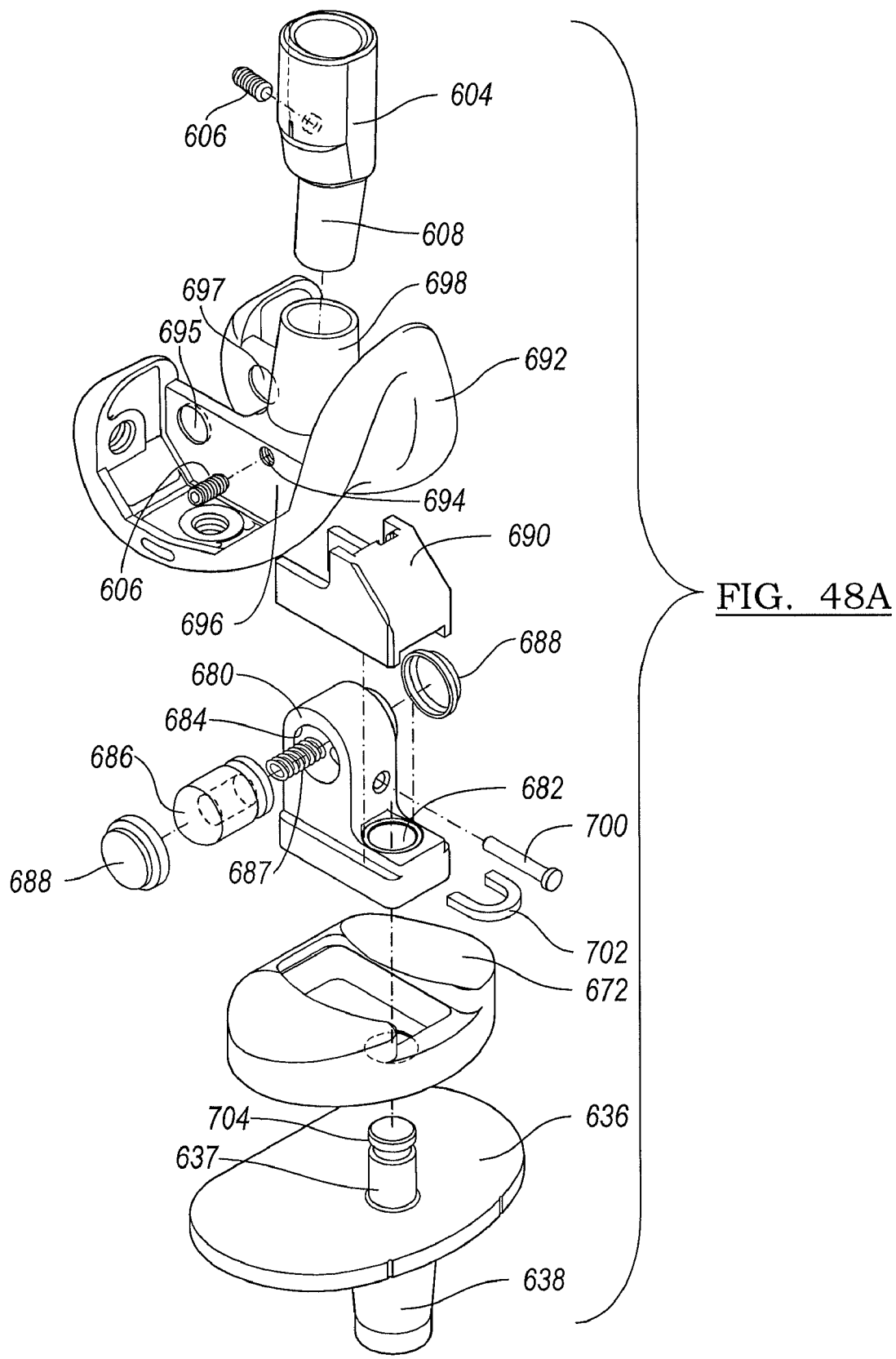

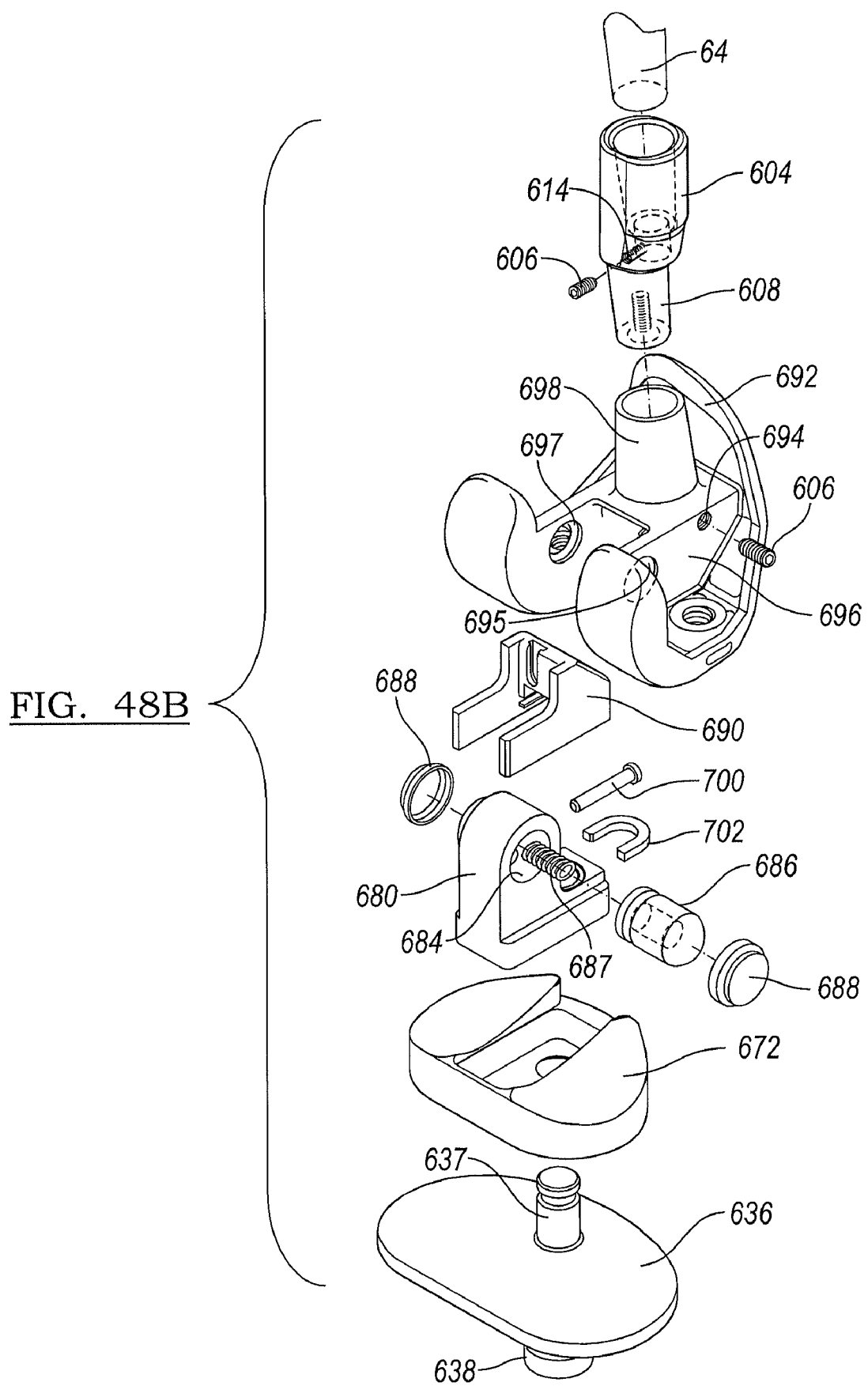

KNEE JOINT PROSTHESIS SYSTEM AND METHOD FOR IMPLANTATION

CROSS-REFERENCE TO RELATED APPLICATIONS

This application claims the benefit of U.S. Provisional Application No. 60/879,733, filed on Jan. 10, 2007 and U.S. Provisional Application No. 60/978,949, filed on Oct. 10, 2007. The disclosures of the above applications are incorporated herein by reference.

FIELD

The present disclosure relates generally to knee joint prostheses and more particularly to various tibial and femoral components and modular augments for cooperating with such tibial and femoral components.

BACKGROUND

A knee joint prosthesis typically comprises a femoral component and a tibial component. The femoral component and tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion as well as absorb and control forces generated during the range of flexion. In some instances however, it may be necessary to replace an existing prosthesis. Such replacement prosthesis are generally referred to as revision knee prostheses. Depending on the degree of damage or deterioration of the primary knee prosthesis, knee tendons and ligaments, however, it may be necessary for a revision knee joint prosthesis to eliminate one or more of these motions in order to provide adequate stability. In this way, it may be desirable to provide a crutiate retaining (CR) revision knee, a fully constrained revision knee, a posterior stabilized (PS) revision knee or a hinged revision knee for example. Furthermore, in some instances it may be necessary to account for bone loss in areas adjacent to such knee joint prostheses.

SUMMARY

A knee joint prosthesis system and method for intraoperatively assembling the same can include a first knee prosthesis component having a first attachment portion and at least a first stem defining a stem engagement portion. A first adapter can have a first adapter engagement portion defining a first axis and a second adapter engagement portion defining a second axis. The first and second axes can be parallel and offset. The first attachment portion can be operable to intraoperatively couple with the stem engagement portion or the first adapter engagement portion.

According to additional features, a second knee prosthesis component, distinct from the first knee prosthesis component, can have a second attachment portion. The second attachment portion can be operable to couple with the stem engagement portion or the first adapter engagement portion. The first knee prosthesis component can be a femoral component and the second knee prosthesis component can be a tibial component. At least one of the femoral components and at least one of the tibial components can cooperate to form each of a crutiate retaining (CR) knee prosthesis, a posterior stabilized (PS) knee prosthesis, a fully constrained knee prosthesis, and a hinged knee prosthesis.

According to still other features, the stem engagement portion can be operable to couple with the second adapter engagement portion. A plurality of stems can be provided, each having a stem engagement portion and defining distinct lengths or diameters. Each of the stem engagement portions can be operable to couple with the first attachment portion of the knee prosthesis component or the second adapter engagement portion of the adapter.

According to other features, the first attachment portion can define a female tapered receiving portion. The stem engagement portion and the first adapter engagement portion can each define a male tapered insertion portion. The female tapered receiving portion can cooperatively engage the male tapered insertion portion by way of a Morse-type taper fit. A first locking member can pass through an adapter bore defined in the first adapter. The first locking member can be operable to lock the first stem to the first adapter. The adapter bore can be threaded. The first locking member can threadably advance along the adapter bore between an unsecured position and a secured position. An insert can be secured to the stem. The first locking member can engage the insert at an interface area in the secured position. The first locking member can be formed of a harder material than the insert such that the insert deforms at an interface area upon advancement of the first locking member to the secured position.

According to yet other features, a plurality of augments defining various shapes and sizes can be provided. Each of the augments can define a passage having a conical engaging surface. Each of the plurality of augments can be operable to couple with a superiorly extending portion of the femoral component or an inferiorly extending portion of the tibial component.

BRIEF DESCRIPTION OF THE DRAWINGS

The present disclosure will become more fully understood from the detailed description and the accompanying drawings, wherein:

FIG. 7B is a view of the knee joint prosthesis of FIG. 1 illustrating various offsets;

FIG. 7C is an exploded view of a locking assembly shown in FIG. 7A;

FIG. 24 is a perspective view of a third augment according to the present teachings;

FIG. 25 is a top view of the third augment of FIG. 24;

FIG. 26 is an anterior view of the femoral component of FIG. 8 shown with the first augment assembled on a superiorly extending portion;

FIG. 27 is an anterior view of the femoral component of FIG. 8 shown with the first and second augments assembled on a superiorly extending portion;

FIGS. 48A and 48B are exploded perspective views of a hinged knee prosthesis according to one example of the present teachings;

DETAILED DESCRIPTION

At the outset, the instant disclosure provides a knee joint prosthesis system having various knee joint prostheses that may be adapted for use in a revision knee procedure. Various tibial and femoral components are described that may be used alone or as part of a crutiate retaining (CR) knee revision, posterior stabilized (PS) knee revision, fully constrained knee revision and hinged knee revision. As will be described, the instant disclosure further provides various modular adapters, stems and augments that may be used in any combination with any of the tibial and femoral components disclosed herein. In other words, all of the components disclosed that are above and below the joint line, such as the stems, adapters, augments, etc., can be inter-changeably used with any of the knee prostheses disclosed herein and on the tibial or femoral side. Moreover, selection of any of the knee prostheses and related components from the knee joint prosthesis system may be selected intra-operatively by the surgeon performing the procedure.

Figure 1:
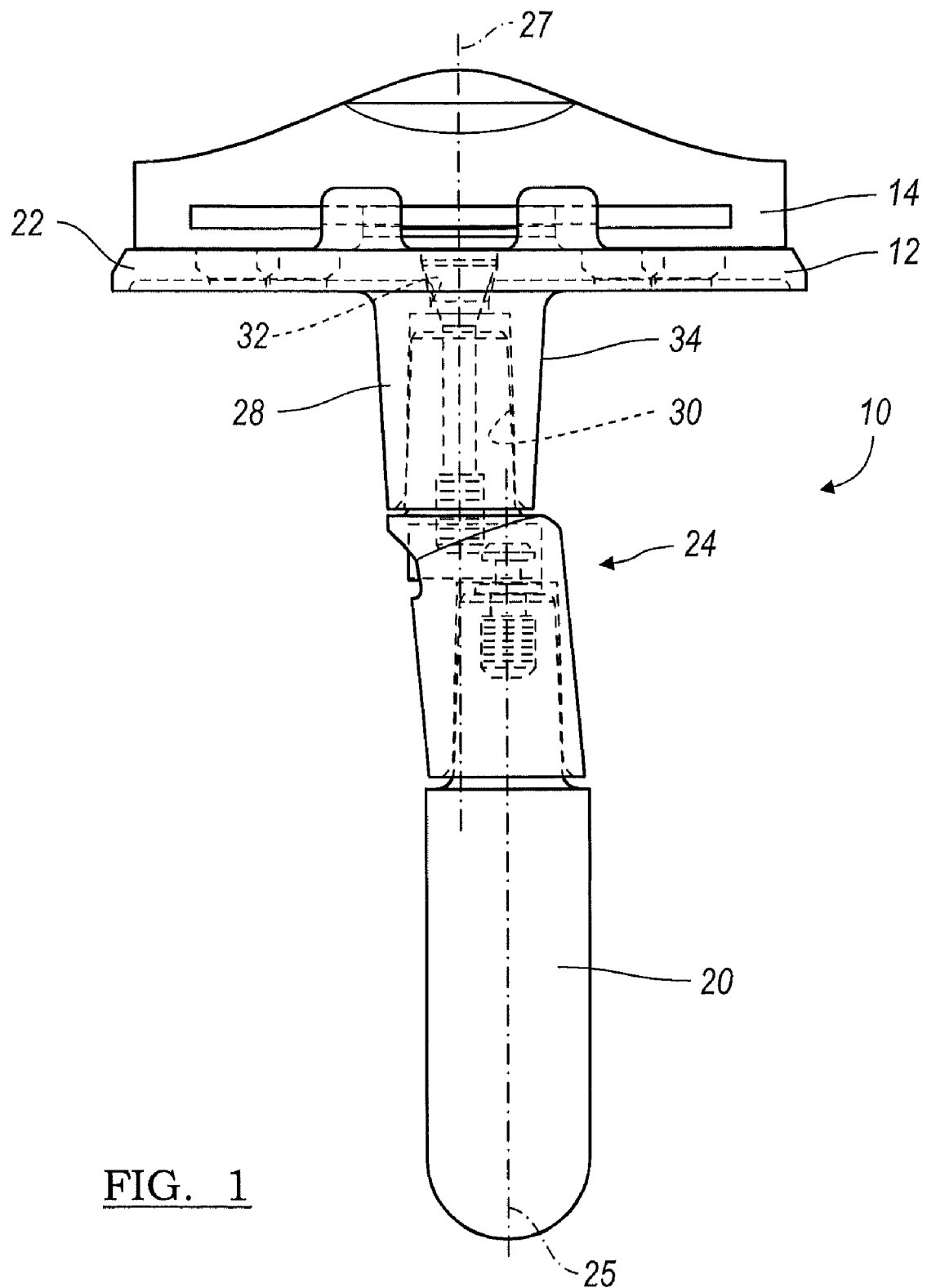
FIG. 1 is an anterior view illustration of a knee joint prosthesis including a modular tibial component having a first adapter assembly for providing a first predetermined offset according to the present teachings.

With initial reference to FIG. 1, a knee joint prosthesis constructed in accordance with the present teachings is illustrated and generally identified at reference number 10. The knee joint prosthesis 10 is generally shown to include a tibial component 12 that supports a bearing 14 which engages an articulation surface of a femoral component (not shown). Insofar as the present teachings are concerned, it will be understood that the tibial tray 12 and bearing 14 can be adapted for use with any suitable femoral component. For example, a first crutiate retaining (CR) bearing 14 is illustrated that is designed to articulate with a CR femoral component. However, a fixed PS bearing may be employed that is designed to articulate with a PS femoral component.

Figure 29:
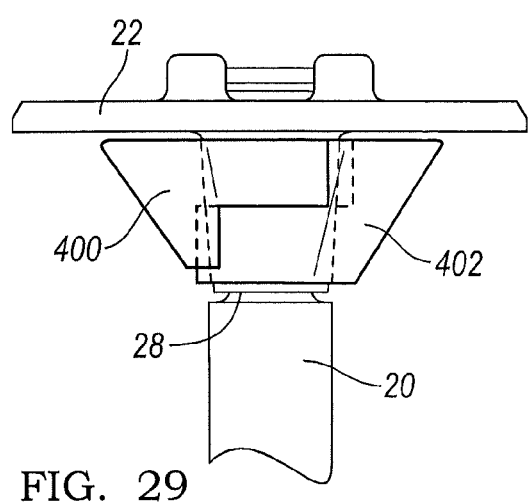
FIG. 29 is an anterior view of the tibial component of FIG. 1 shown with the first and second augments assembled on an inferiorly extending portion and without the adapter assembly.

The tibial component 12 illustrated in FIG. 1 will be understood to be modular in construction and generally include a stem 20, a tray 22, and a first adapter assembly 24. In a manner which will be discussed more fully below, the adapter assembly 24 can connect the tray 22 and the stem 20 so as to provide an offset to the stem 20 in the transverse or coronal plane or in any other plane. Explaining further, when the stem 20 is attached to the tray 22 through the first adapter assembly 24, a central axis 25 of the stem 20 can be offset from a central axis 27 of an inferiorly extending portion 28 of the tray 22. In the embodiment illustrated, the first adapter assembly 24 can provide a first offset of approximately 5 mm. It is appreciated that the offset can range from 0 mm to approximately 5 mm or more and can be in any rotational direction relative to the central axis 27. Alternatively, a stem 20 can be attached directly to the tray 22 (FIG. 29). In other words, the offset axis 25 can be rotated 360 degrees relative to the central axis 27 to provide the surgeon with various intra-operative options to select depending on the patient's needs. Alternatively, the adapter assembly 24 or stem 20 can be rotational keyed to provide only a limited range of adjustment, such as providing only a single offset or two offset positions.

Figure 2:
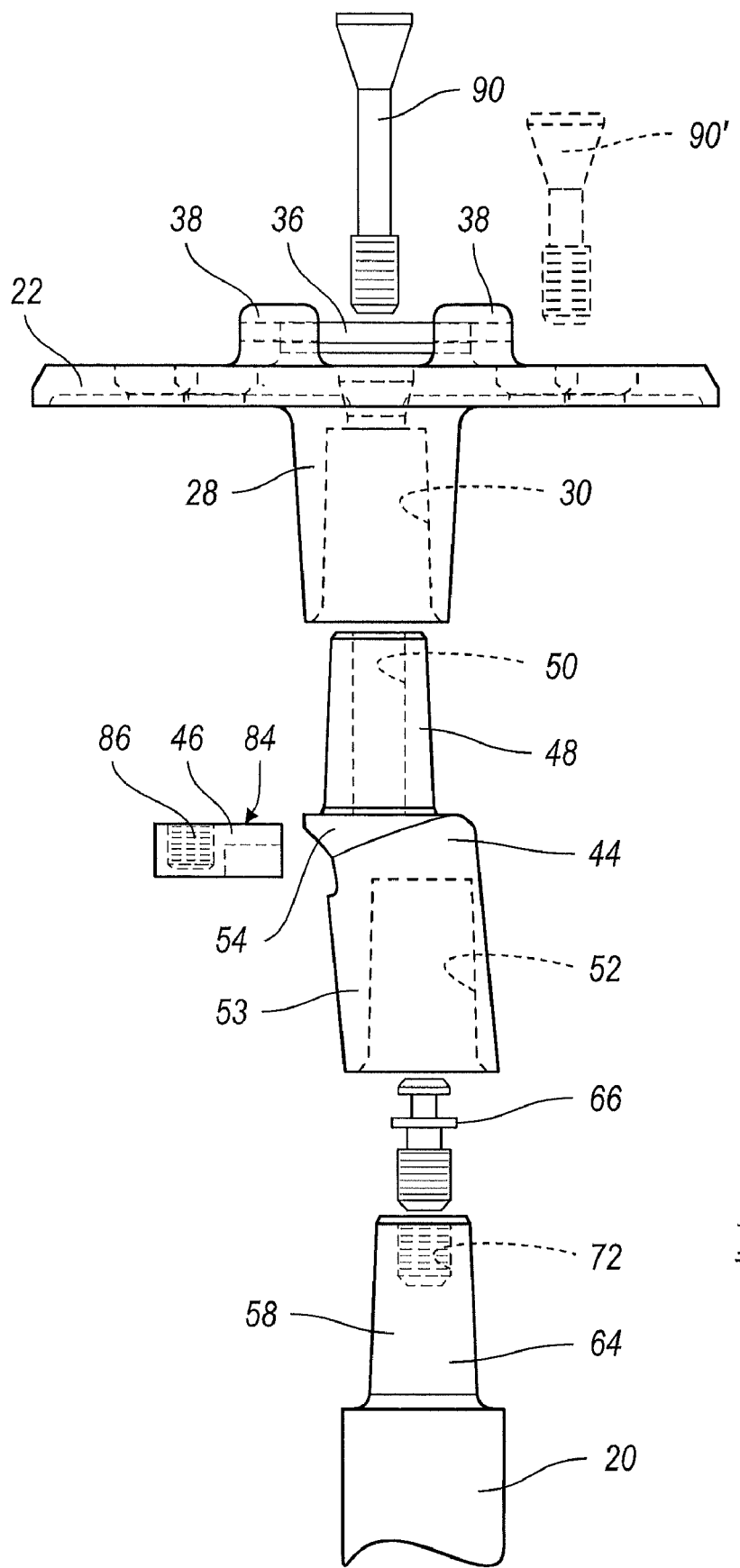
FIG. 2 is an exploded view of the modular tibial component of FIG. 1.
Figure 3A:
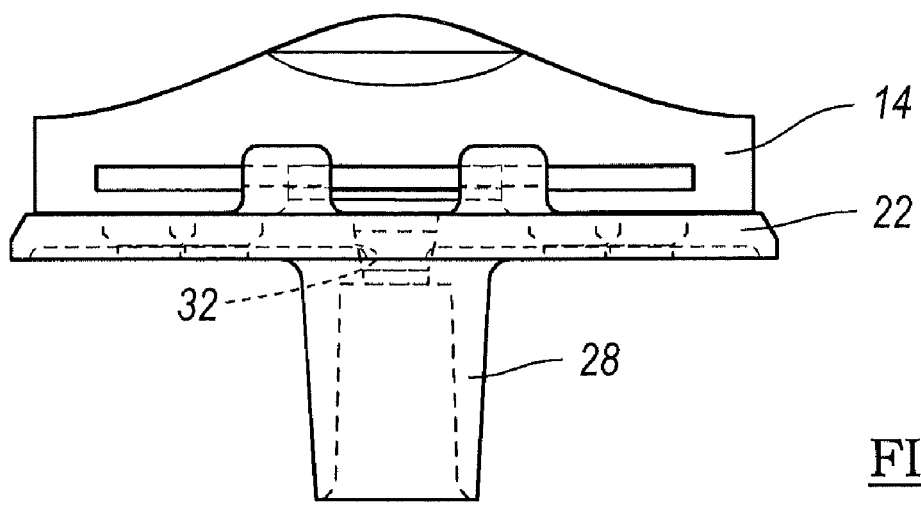
FIG. 3A is an anterior view of the tibial component of FIG. 1.
Figure 3B:
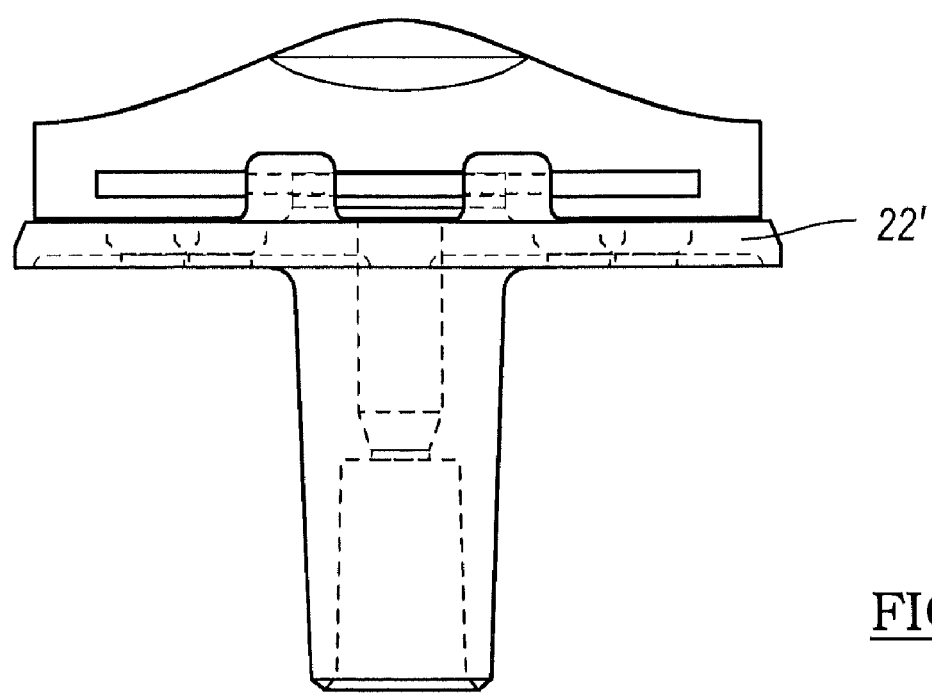
FIG. 3B is an anterior view of a tibial component according to additional features.
Figure 3C:
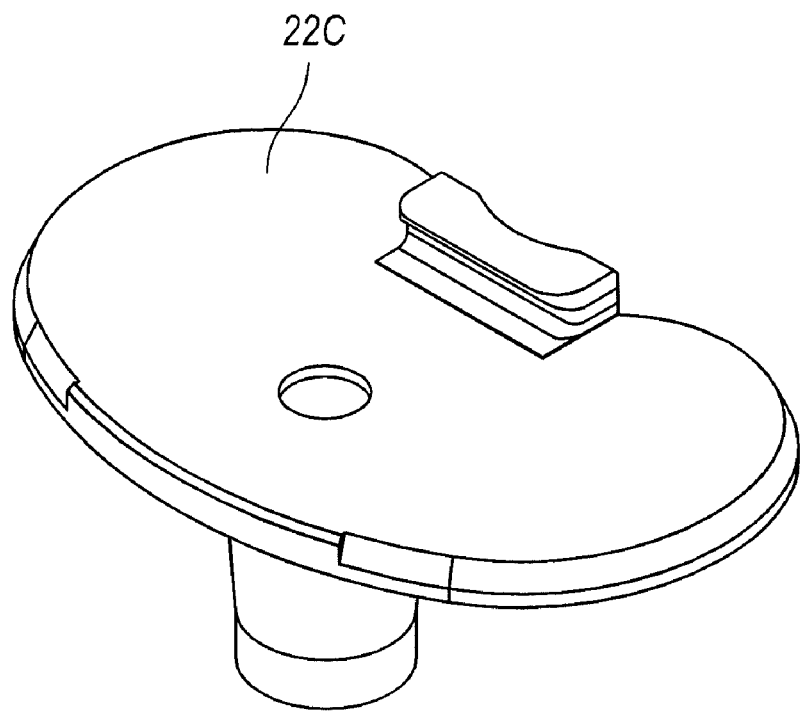
FIG. 3C is a perspective view of a tibial component according to additional features.
Figure 3D:
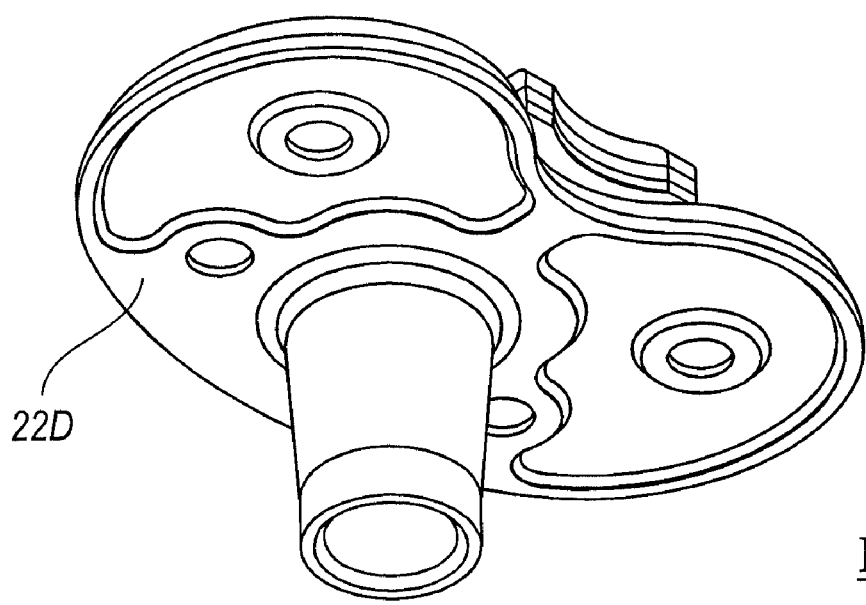
FIG. 3D is a perspective view of a tibial component according to additional features.

With reference to FIGS. 2 and 3A, the inferiorly extending portion 28 of the tibial tray 22 can define a female tapered receiving portion 30. The female tapered receiving portion 30 can taper slightly as it extends into the inferiorly extending portion 28. A central aperture 32 can be formed through the tray 22 and the inferiorly extending portion 28 into the female tapered receiving portion 30. The inferiorly extending portion 28 may also define an exterior tapered augment receiving surface 34. A retaining rail 36 (FIG. 2) can extend superiorly from a posterior edge of the tray 22. The tibial tray 22 can further include a pair of posts 38 integrally formed on a superior surface at an anterior edge thereof. The posts 38 and rail 36 can cooperate to retain the modular bearing 14 in a fixed position on the tray 22. An alternate tibial tray 22' is shown in FIG. 3B.

The modular bearing 14 can be formed of ultra-high molecular weight polyethylene (UHMWPE) with anterior and posterior recesses (not specifically shown) to receive the posts 38 and rail 36, respectively, and with a uniformly flat inferior surface on its intercondylar and medial/lateral portions for direct contact with the superior surface of the tray 22. The modular bearing 14 can be designed to be locked in position with a transverse slide-in locking bar or clip 40 wedged between the posts 38 and the bearing 14 in opposed grooves provided therein for that purpose. A more detailed discussion of how the locking bar cooperates with the posts and bearing may be found in commonly owned U.S. Pat. No. 5,330,534 entitled "Knee Joint Prosthesis With Interchangeable Components", which is hereby incorporated by reference. Modular tibial trays and bearings as generally described above are commercially available from Biomet Inc., the assignee of the present disclosure, as components of the Vanguard® Complete Knee System, which includes various sizes and configurations of trays, bearings and other knee components for different patient requirements. The articulating surfaces of the modular bearing 14 can be substantially the same as provided by the Vanguard® Complete Knee System.

Figure 4:
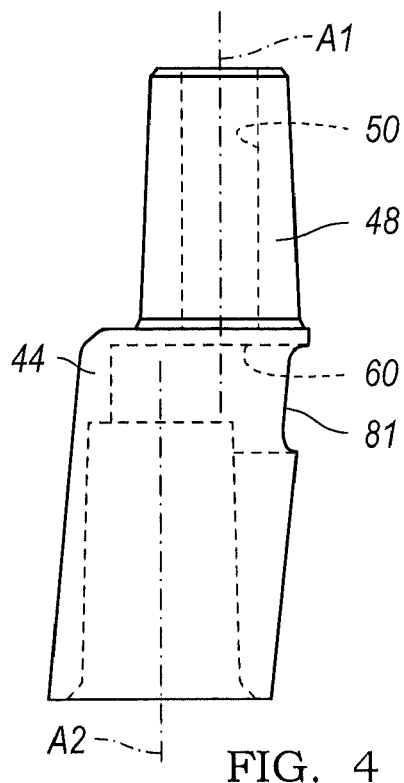
FIG. 4 is a view of a first adapter body according to the present teachings.
Figure 5:
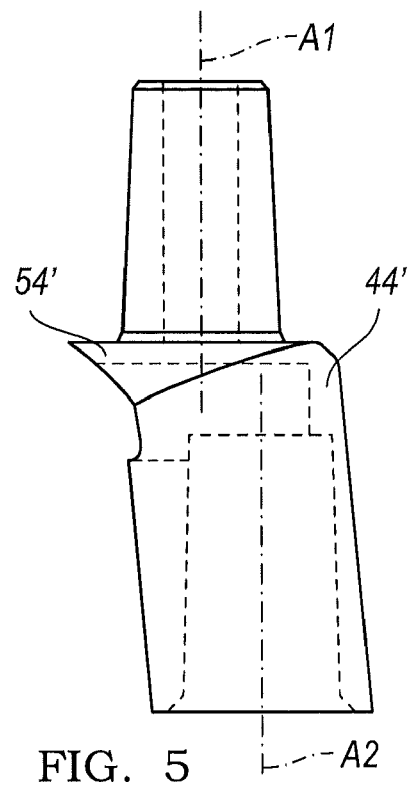
FIG. 5 is a view of another adapter body according to additional features.

Turning now to FIGS. 2, 4 and 5, the adapter assembly 24 can generally include an adapter body 44 and a locking member or element 46 (FIG. 2). The adapter body 44 of the adapter assembly 24 can define a male tapered insertion portion 48 having a passage 50 formed therethrough. A female tapered receiving portion 52 can be formed in an offset body portion 53 of the adapter body 44 for receiving a male tapered insertion portion 58 of the stem 20. In one example, the female tapered receiving portion 52 can be generally cylindrical. A skirt 54 can be defined at a transition between the male tapered insertion portion 48 and the offset body portion 53.

With reference to FIG. 4, the male tapered insertion portion 48 of the adapter body 44 defines a first axis $A_1$ and the female tapered receiving portion 52 defines a second axis $A_2$. Further, in the embodiment illustrated, the first axis $A_1$ and the second axis $A_2$ are parallel to one another and spaced apart to provide the desired offset. In this regard, multiple adaptors each having a different offset can be provided to provide the surgeon with intra-operative selection depending on the patient's needs. Insofar as the adapter body 44 provides a 5 mm offset, the first and second central axes $A_1$ and $A_2$ are spaced apart 5 mm. The adapter body 44' can define a skirt 54' having an alternate configuration. Other geometries are contemplated for the skirt 54, 54'.

The male tapered insertion portion 48 can taper slightly as it extends away from the adapter body 44. The female tapered receiving portion 52 similarly tapers slightly as it extends into the adapter body 44 from an end of the adapter body 44. As will become appreciated from the following discussion, various male tapered insertion portions (such as portion 48) can be inserted in various female tapered receiving portions (such as portion 52) to form a locking taper or Morse taper. The adapter body 44 is illustrated to further define a laterally extending channel 60 which intersects both the aperture 50 and the female tapered receiving portion 52. In a manner to be described further below, the locking element 46 can extend into the laterally extending channel 60 where it ultimately couples the tray 22 to the stem 20.

Figure 6:
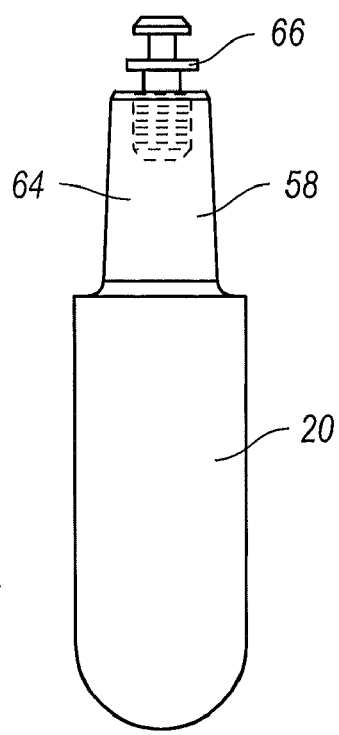
FIG. 6 is a view of an exemplary stem and fastener insert.

As shown in FIGS. 2 and 6, the stem 20 can include an upper portion 64 that cooperatively engages with the locking element 46. In the embodiment illustrated, the upper portion 64 of the stem 20 can include a fastener insert 66. Alternatively, the fastener insert 66 of the stem 20 may be integrally formed to cooperate with the locking element 46.

The fastener insert 66 can include a distal portion 70 which can be externally threaded for engaging an internally threaded aperture 72 of the male tapered insertion portion 58 of the stem 20. The fastener insert 66 can further include a central portion 74 having a hexagonal or other suitable cross-section which can be engaged by a tool (not shown) for rotating the fastener insert 66 into the stem 20. Further, the fastener insert 66 can include a proximal end 78 including an enlarged diameter head 80.

The locking element 46 can be sized and configured to be inserted through an opening 81 in the sidewall of the adapter body 44 and into the channel 60 for coupling of the stem 20 and the tray 22. The locking element 46 can include an upper surface 84 (see FIG. 2) having an internally threaded aperture 86. The internally threaded aperture 86 can threadably receive a fastener 90 which can extend through the central aperture 32 provided in the tray 22. The fastener 90 can align with the central longitudinal axis 27 of the inferior portion 28 of the tray 22.

Figure 7A:
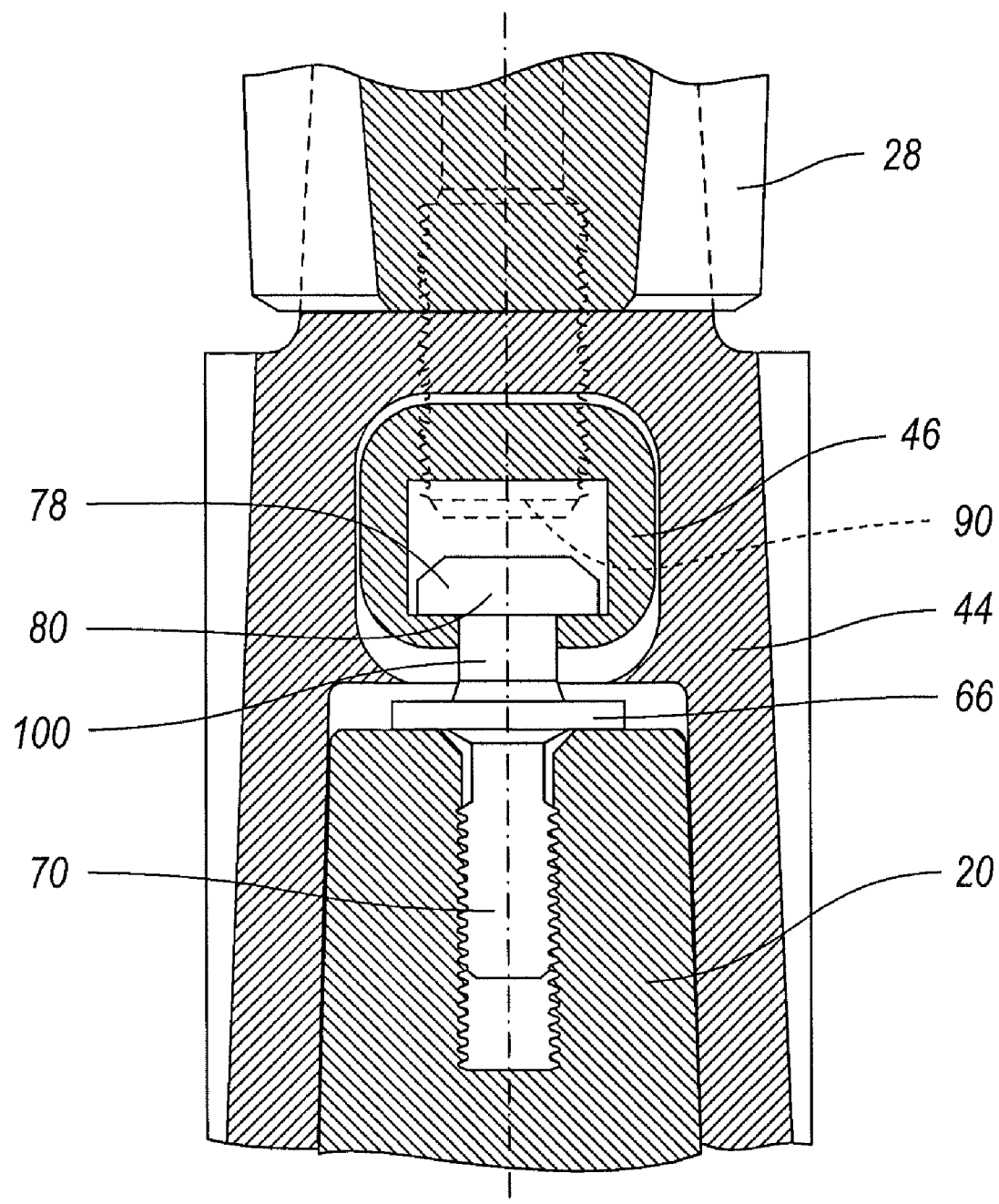
FIG. 7A is a cross-sectional view taken along a superior/inferior line through the adapter of FIG. 1.

With additional reference to FIG. 7C, the locking element 46 can additionally include an open end 94 and a bottom surface having a slot 96. The slot 96 can intersect the open end 94. The open end 94 can receive the head 80 of the stem insert 66 as the locking element 46 is inserted through the opening 60. The slot 96 can accommodate a reduced diameter, central portion 100 of the fastener insert 66. The head 80 of the fastener insert 66 can have a diameter greater than a width of the slot 94 for coupling of the fastener insert 66 with the locking element 46.

The locking element 46 can further include a closed end 104. The closed end 104 can be convexly curved. When the locking element 46 is completely inserted into the channel 60, the closed end 104 can be flush with the sidewall of the adapter body 44.

In use, the fastener insert 66 can be screwed into the stem 20. Next, the adapter body 44 can be placed over the male insertion portion 64 of the stem 20 such that the male insertion portion 64 is received in a press fit within the female tapered receiving portion 52 of the adapter body 44 and the upper end 78 of the fastener insert 66 extends into the laterally extending channel 60.

The male taper extension 48 of the adapter 44 can now be press fit onto the female tapered receiving portion 30 of the tray 12 with the adapter body 44 oriented to provide the offset in the desired direction. As viewed in FIG. 7B, the adapter body 44 may be rotated about the axis $A_1$ prior to fastening to orient the stem 20 at the desired offset for a particular patient. As a result, the stem 20 may extend at a plurality of positions around a radius defined by the axes $A_1$ and $A_2$. Alternatively, the stem 20 may be keyed with the adapted body thus, precluding rotation. In addition, a set of stems may be provided having various lengths suitable for a range of patients. Likewise, a set of adapter bodies may be provided for providing various offsets.

At this point, the locking element 46 can be inserted into the laterally extending channel 60 through the opening 81. Upon complete insertion, the locking element 46 can engage the fastener insert 66. The tray 22 can be secured to the adapter body 44 by the threaded fastener 90 which extends through the central aperture 32 of the tray 22 and threadably engages the internally threaded aperture 86 of the locking element 46. A further discussion of offset stems and their application with respect to various tibial and femoral components may be found in commonly owned U.S. patent application Ser. No. 10/934,282 filed Sep. 3, 2004 and entitled "Knee Joint Prosthesis", which is hereby incorporated by reference. In this commonly owned Application, the tibial tray defines an inferiorly extending male portion whereas in the instant application, the tibial tray 22 defines the inferiorly extending the female receiving portion 30. In addition, while not specifically shown, the adapter body 44 may alternatively define an axis $A_2$ that defines an angle with respect to the axis $A_1$.

In another example, the male insertion portion 58 may be inserted directly into the female receiving portion 30 of the tray 22. In this example, another threaded fastener 90' may be used that has a shorter shaft for spanning an appropriate distance to mate directly with the threaded aperture 72 of the stem 20. As shown in FIGS. 3A-3D, other tibial trays 22A, 22B, 22C and 22D, are shown for accommodating various combinations of fasteners 90, 90', adapters 44, 44' and stems 20.

Figure 8:
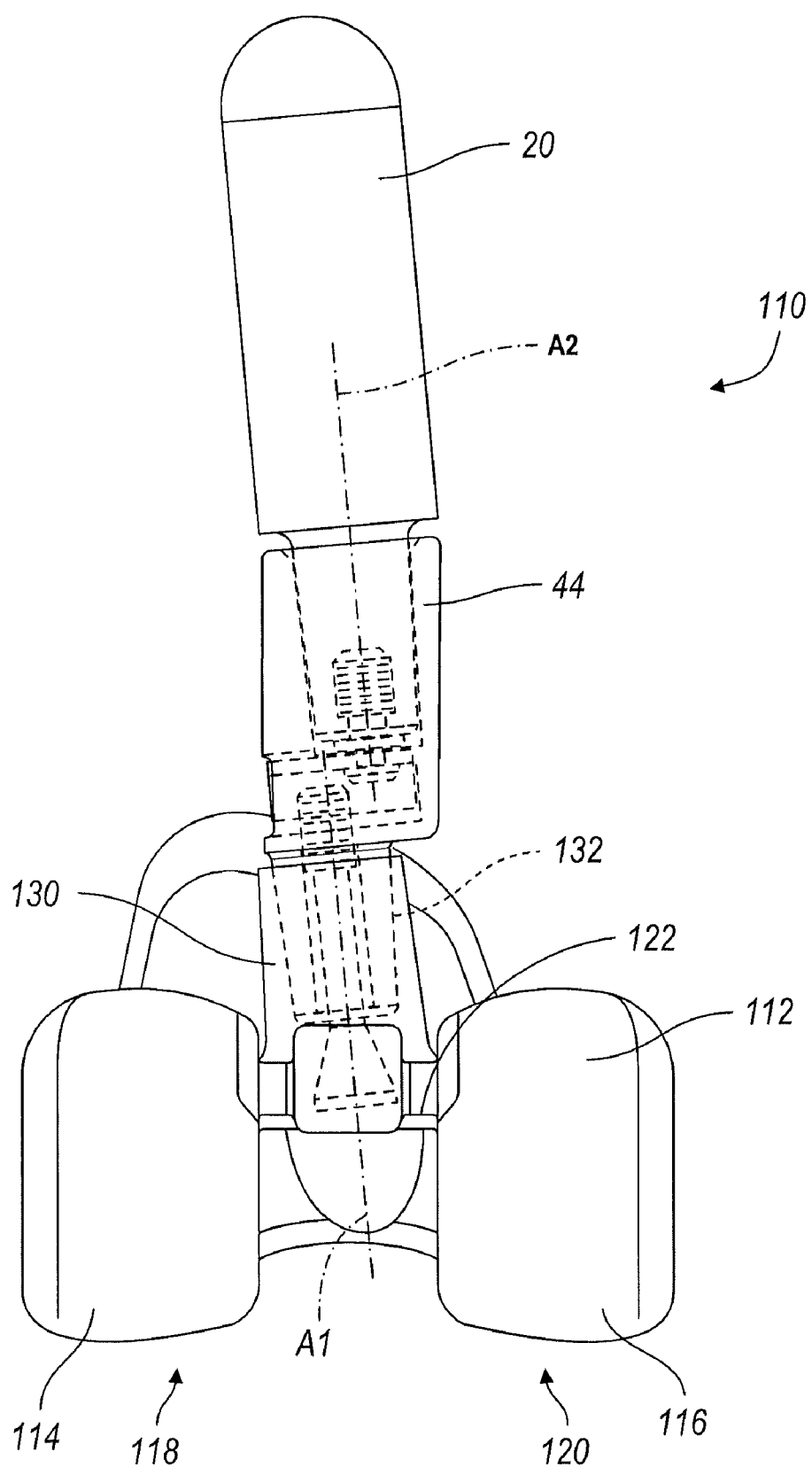
FIG. 8 is an anterior view of an exemplary femoral component according to the present teachings and shown with the adapter assembly of FIG. 1.
Figure 9:
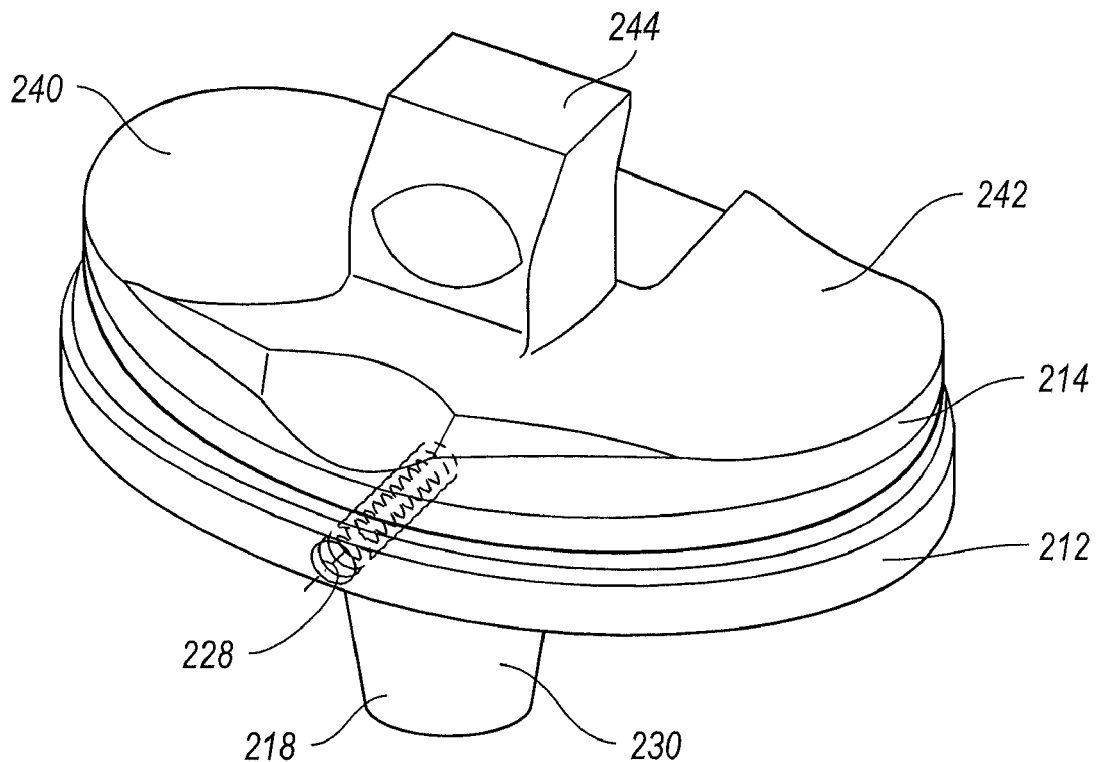
FIG. 9 is a perspective view of a tibial tray and bearing according to additional features.
Figure 10:
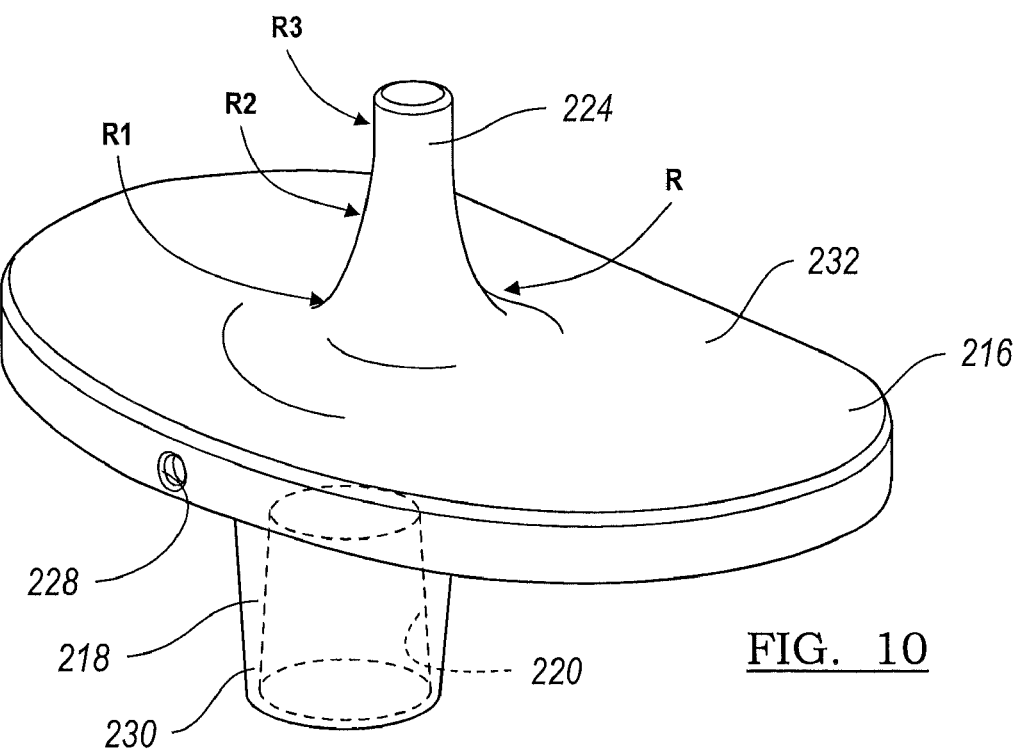
FIG. 10 is a perspective view of the tibial tray of FIG. 9.
Figure 11:
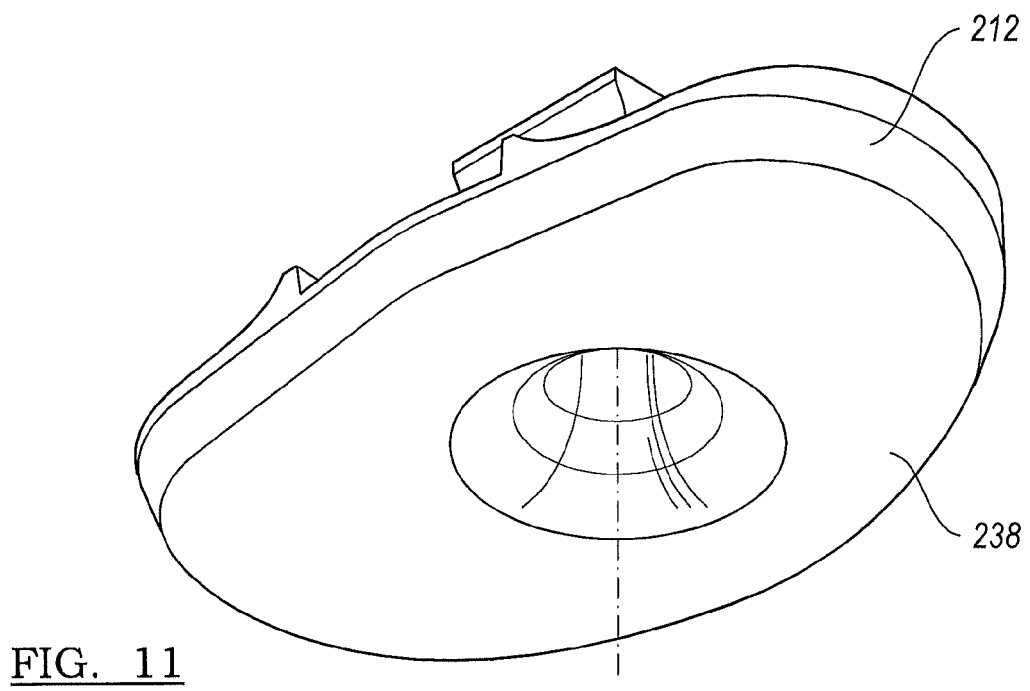
FIG. 11 is a perspective view of an inferior surface of the bearing of FIG. 9.
Figure 12:
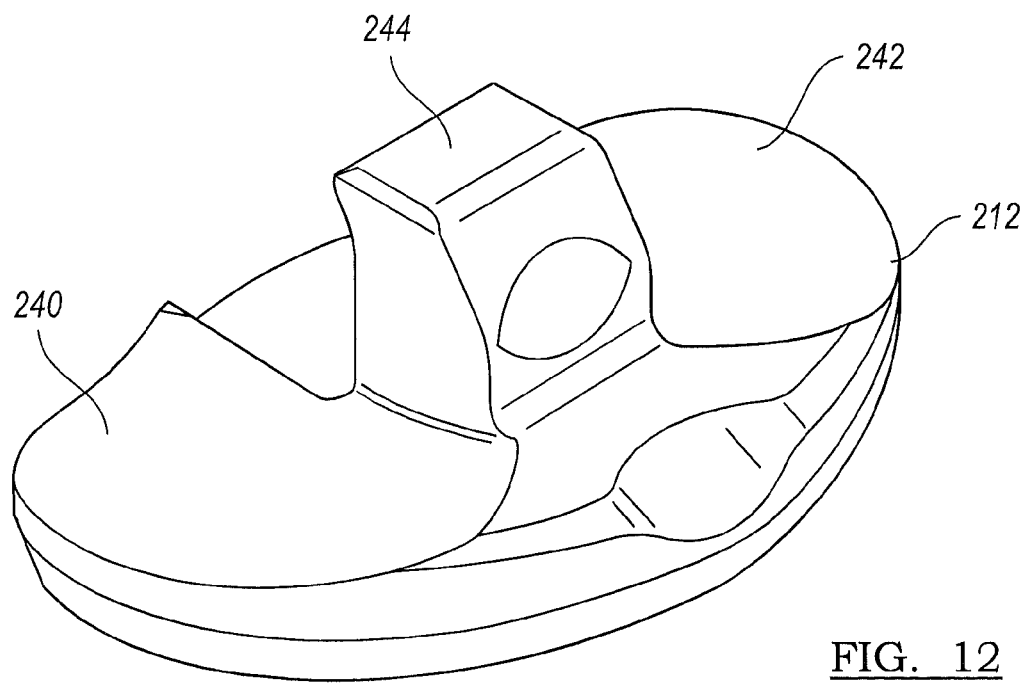
FIG. 12 is a perspective view of a superior surface of the bearing of FIG. 9.

Turning now to FIG. 8, a knee joint prosthesis according to another example is shown and generally identified at reference number 110. The knee joint prosthesis 110 includes a femoral component 112. The femoral component 112 may be used as part of a posterior stabilized (PS) knee joint prosthesis. A PS knee joint prosthesis can provide adequate stability in case of moderate deterioration or instability of a knee. This most typically occurs when the anterior and posterior cruciate ligaments are sacrificed or dysfunctional and the medial and lateral collateral ligaments remain functionally intact. The femoral component 112 can include a first condylar portion 114 and a second condylar portion 116 that provide a first femoral bearing surface 118 and a second femoral bearing surface 120, respectively. The first and second condylar portions 114 and 116 of the femoral component 112 can be interconnected by an inner condylar portion 122 that defines an intercondylar recess 124. A superiorly extending portion 130 may be formed on the femoral component 112. The superiorly extending portion 130 can include a generally tapered outer body to receive the augments described herein and define a female tapered receiving portion 132.

According to the present teachings, the female tapered receiving portion 132 of the femoral component 112 may be configured to accept one of the adapter bodies 44, 44' described above. In this way, the male tapered insertion portion 48 of the adapter body 44 can be adapted to be inserted and press-fit into the female tapered receiving portion 132 of the femoral component 112. As can be appreciated, the first axis $A_1$ and the second axis $A_2$ are parallel to one another and spaced apart. Again, the exemplary adapter assembly 24 has been described as having a 5 mm offset however, other adapter bodies may be provided having various offsets. A locking element 46 and stem 20 may be used according to the description above.

Turning now to FIGS. 9-14, a knee joint prosthesis according to another example is shown and generally identified at reference number 210. The knee joint prosthesis 210 is generally shown to include a tibial component 212 that supports a rotating constrained bearing 214. The tibial component 212 can generally include a substantially planar platform-like tibial tray 216 (FIG. 10) and an inferiorly extending portion 218. The inferiorly extending portion 218 can define a tapered female receiving portion 220 and an outer tapered body for receiving augments disclosed herein.

The tibial tray 216 can further include a superiorly extending post 224. A transition between the tibial tray 216 and the superiorly extending post 224 can be defined by a varying radius R, or more specifically transition between a radius $R_1$ having a radius of approximately 0.50 inches, and a radius $R_3$ having a radius of approximately 1.50 inches. An intermediate radius $R_2$ can have a radius of approximately 0.38 inches. It is appreciated that the radius R may define other dimensions. The transition of the varying radius R can minimize stresses experienced on the superiorly extending post 224. An axis $A_3$ (FIG. 14) defined through the post 224 can be laterally offset in the posterior direction relative to an axis $A_4$ defined through the inferiorly extending portion 218. A threaded aperture 228 can be formed through the anterior portion of the tibial tray 216. The threaded aperture 228 can extend generally perpendicular to the axis $A_4$.

The inferiorly extending portion 218 can define a tapered augment receiving surface 230. The tibial tray 216 can be formed from cobalt-chromium-molybdenum or any other suitable biocompatible material. A top 232 (FIG. 10) of the tibial tray 216 can be highly polished to provide a substantially smooth tibial bearing surface 234.

Figure 13:
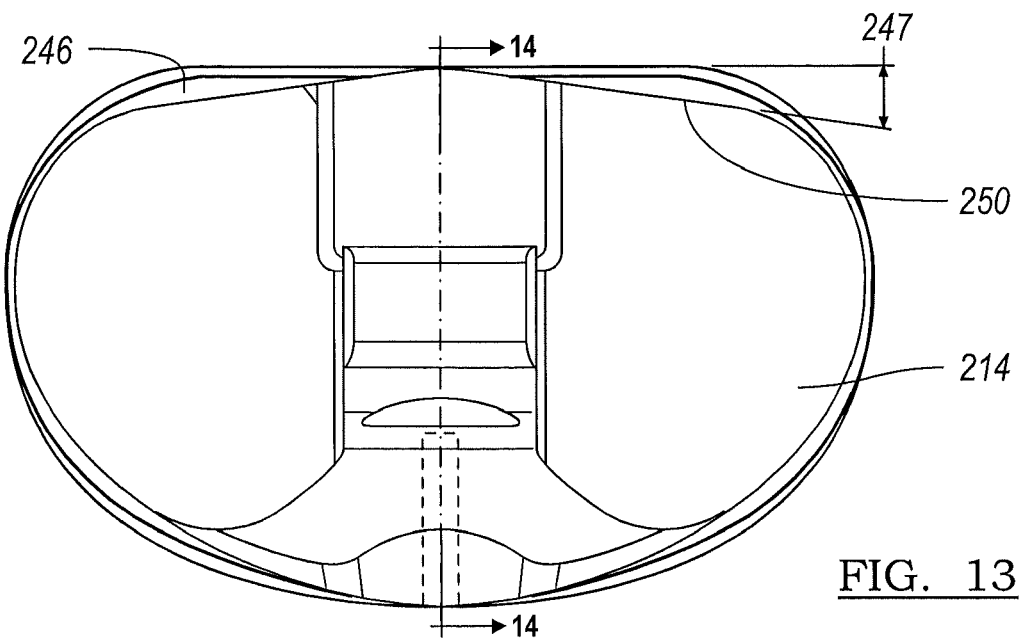
FIG. 13 is a top view of the tibial tray and bearing of FIG. 9.

The rotating bearing 214 can have a substantially planar inferior bearing surface 238 (FIG. 11) which can rotatably move relative to the highly polished tibial bearing surface 234. The rotating bearing 212 can further include a first superior articulating or bearing surface 240 and a second superior articulating or bearing surface 242. The bearing surfaces 240 and 242 can be formed anteriorly and laterally from a central superiorly extending portion 244. The first bearing surface 240 and the second bearing surface 242 can articulate with respective bearing surfaces of a first and second condyle of a constrained femoral component (not shown). The rotating bearing 212 can be formed from a surgical grade, low friction, low wearing plastic, such as UHMWPE or other suitable material. As shown in FIG. 13, a posterior edge 246 of the tibial tray 216 can define a surface that defines an angle 247 relative to a posterior edge 250 of the bearing 214. The angle 247 can be approximately 8 degrees. Other angles are contemplated.

Figure 14:
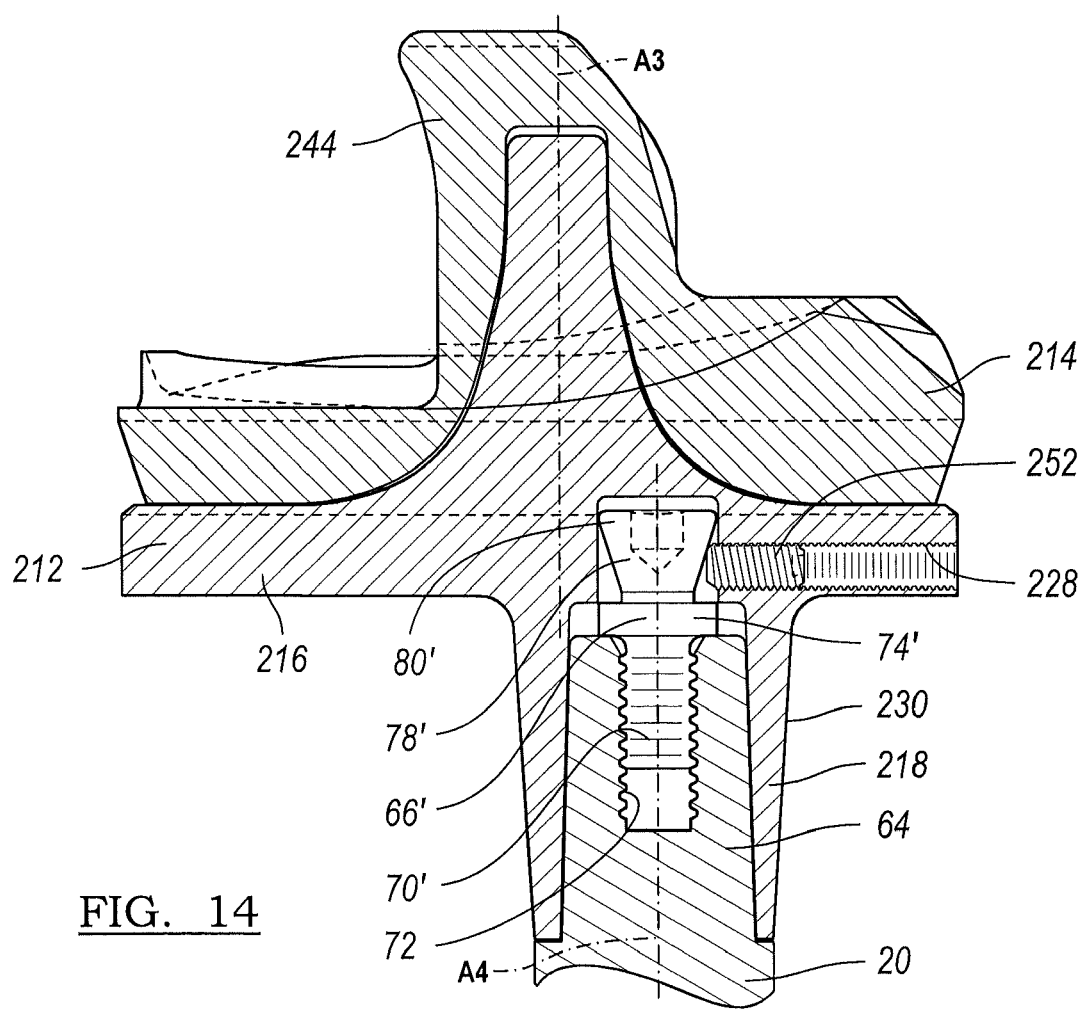
FIG. 14 is a cross-sectional view taken along the line 14-14 of FIG. 13.
Figure 15:
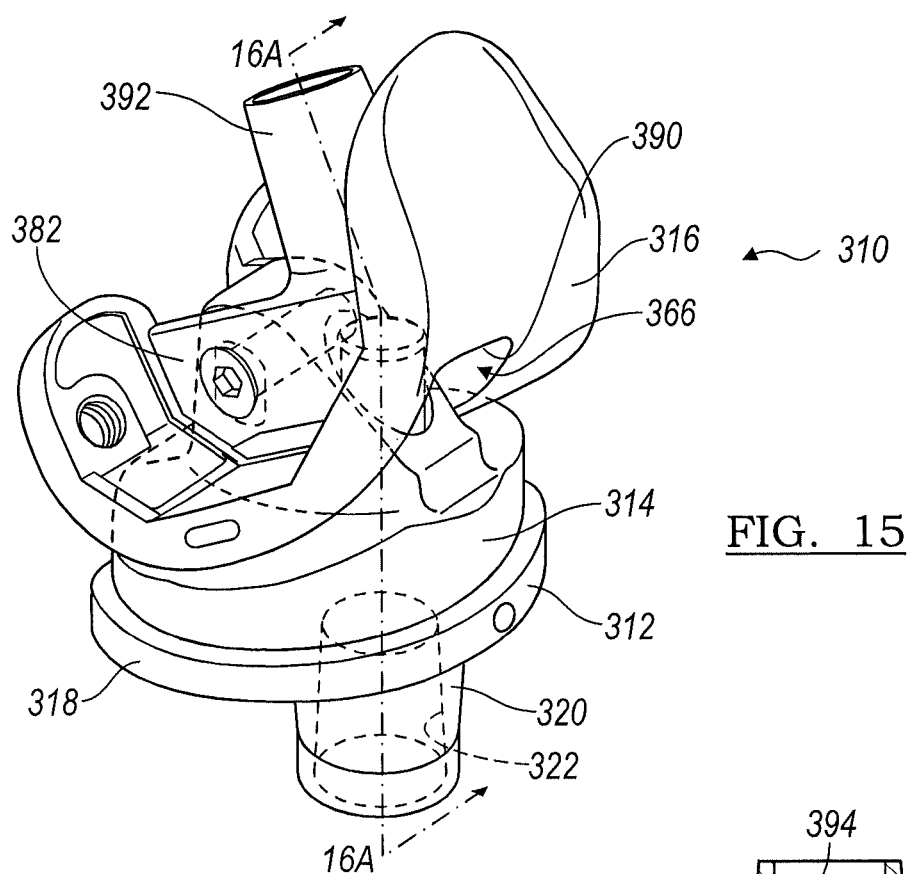
FIG. 15 is a perspective view of a hinged knee joint prosthesis according to additional features.

Turning now to FIG. 14, a stem 20 is shown received directly into the female tapered receiving portion 220 of the tray 216. Again, instead of inserting a stem 20 directly into the female tapered receiving portion 220 of the tray 216, an adapter body 44 or 44' may be used. The stem 20 can include a fastener insert 66'. The fastener insert 66' can include a distal portion 70' which is externally threaded for engaging an internally threaded aperture 72 of the male tapered insertion portion 64 of the stem 20. The fastener insert 66' can further include a central portion 74' having a hexagonal or other suitable cross-section which can be engaged by a tool (not shown) for rotating the fastener insert 66' into the stem 20. Further, the fastener insert 66' can include an upper end 78' including a conical engaging head 80'. A set screw 252 can be advanced through the threaded aperture 228 of the tibial tray 216 to engage the conical engaging head 80'. In this way, advancement of the set screw 252 can secure the fastener insert 66', and therefore, the stem 20 in a secure position. It is appreciated that when utilizing the adapter body 44, a fastener such as fastener insert 66' but having a longer shank, may alternately be used for threadably securing to the locking element 46.

Turning now to FIGS. 15-20, a hinged knee joint prosthesis constructed in accordance with the present teachings is illustrated and generally identified at reference number 310. The knee joint prosthesis 310 is generally shown to include a tibial component 312 that supports a bearing 314 which engages an articulation surface of a femoral component 316. The tibial component 312 can generally include a substantially planar platform-like tibial tray 318 and an inferiorly extending portion 320. The inferiorly extending portion 320 can define a tapered female receiving portion 322.

Figure 16A:
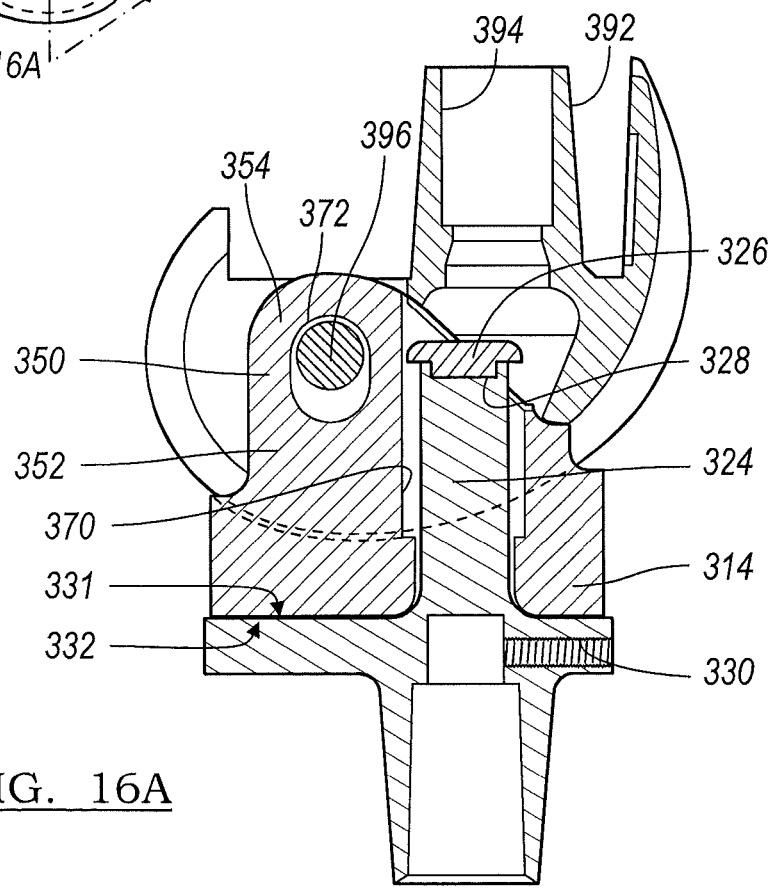
FIG. 16A is a cross-sectional view taken along the line 16-16 of FIG. 15 and shown with the femoral component rotated.

With additional reference to FIG. 16A, the tibial tray 318 can further include a superiorly extending post 324. As will be described, a cap 326 can be securably inserted into an elongate bore 328 defined at a terminal opening of the superiorly extending post 324. A threaded aperture 330 can be formed through the tibial tray 318. The threaded aperture 330 can extend generally perpendicular to an axis defined by the superiorly extending post 324. The tibial tray 318 can be formed from cobalt-chromium-molybdenum or any other suitable biocompatible material. A set screw (not shown) can be advanced through the threaded aperture 330 of the tibial tray 318 to engage a conical engaging head of a fastener insert (as described in detail above regarding FIG. 14). In this way, advancement of the set screw can secure the fastener insert, and therefore the adapter body 44 or the stem 20 in a secure position. The top of the tibial tray 318 can be highly polished to provide a substantially smooth tibial bearing surface 331.

Figure 17:
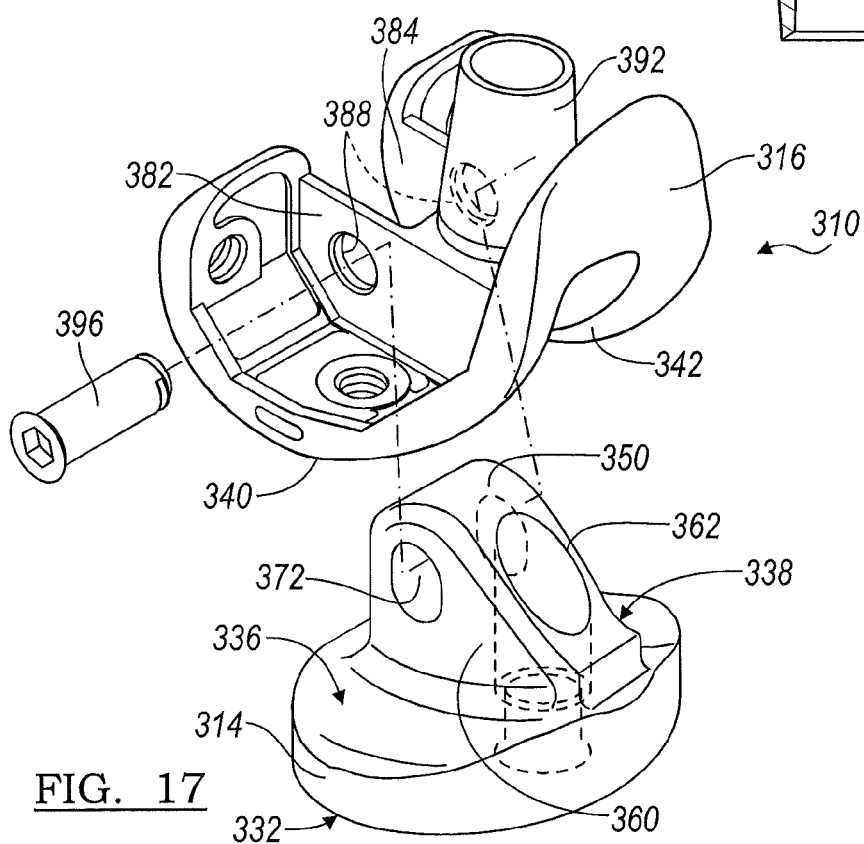
FIGS. 17-20 show an exemplary sequence of assembling the knee joint prosthesis of FIG. 15.
Figure 18:
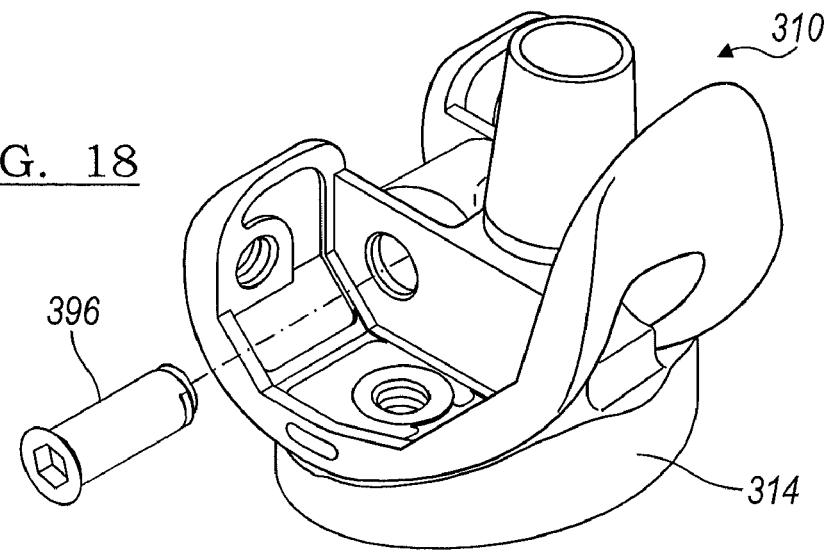

The rotating bearing 314 can have a substantially planar inferior bearing surface 332 which can rotatably move relative to the highly polished tibial bearing surface 331. The rotating bearing 314 can further include a first superior articulating or bearing surface 336 and a second superior articulating or bearing surface 338. The first bearing surface 336 and the second bearing surface 338 can articulate with respective bearing surfaces of a first and second condyle 340 and 342, respectively of the femoral component 316. Again, as described above, the bearing surfaces may be similar to those provided in the Vanguardo Complete Knee System. To accommodate guiding movement of the femoral component 316, the bearing 314 can include a stabilizing post 350 which can project superiorly from the bearing surface. The stabilizing post 350 can include a fin-like body 352 having a raised posterior portion 354 and a lower anterior portion 356. The body 350 can define a first and second laterally spaced-apart sides 360 and 362 (FIG. 17). The first and second sides 360 and 362 of the stabilizing post 350 can be positioned so as to extend into an intercondylar recess 366 (FIG. 15) of the femoral component 316. A stabilizing post aperture 370 can be formed in a superior/inferior direction through the body 350.

A passage 372 can be formed through the raised posterior portion 354 of the body 350. The passage 372 can extend generally through the first and second sides 360 and 362 of the stabilizing post 350 in a direction generally perpendicular to the stabilizing post aperture 370. The rotating bearing 314 can be formed from a surgical grade, low friction, low wearing plastic, such as UHMWPE or other suitable material.

Figure 16B:
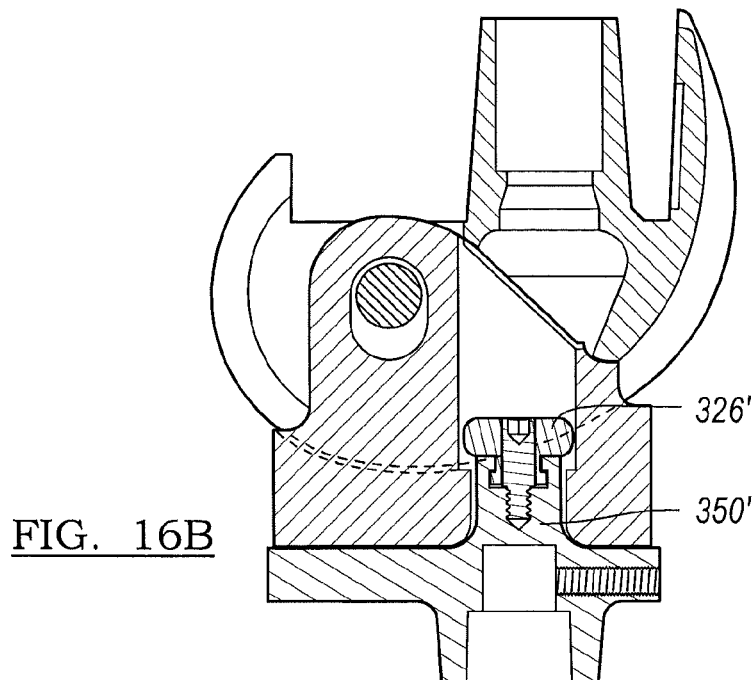
FIG. 16B is a cross-sectional view of a hinged knee prosthesis according to additional features.

An alternate stabilizing post 350' is shown in FIG. 16B that accepts a cap or fastener 326'.

The first and second condylar portions 340 and 342 of the femoral component 316 can be interconnected by an inner condylar portion 380 that defines the intercondylar recess 366. The intercondylar portion 380 can include a first lateral sidewall 382 and a second lateral sidewall 384 (FIG. 17) which can be planar and substantially parallel to each other. The first and second lateral sidewalls 382 and 384 can further define hinge passages 388 formed respectively therethrough.

Anterior portions of the first and second lateral sidewalls 382 and 384 can be connected by an anterior surface 390 (FIG. 15) of the intercondylar portion 380. In one example, the anterior surface 390 of the intercondylar portion 380 can angle anteriorly in an inferior direction at approximately 60 degrees with respect to a superior surface of the intercondylar portion 380. A superiorly extending portion 392 may be formed on the femoral component 316 and generally extend from a superior surface 394 (FIG. 16A). The superiorly extending portion 392 can include a generally cylindrical body and define a female tapered receiving portion 394.

A hinge post 396 can securably extend through the respective hinge passages 388 of the first and second lateral sidewalls 382 and 384 of the femoral component 316 and through the passage 372 in the bearing 314. Of note, the lateral sidewalls 382 and 384 of the femoral component 316 can be positioned proximate an inboard portion of the respective first and second condyles 340 and 342. In this way, host bone need not be sacrificed in areas outboard to the lateral sidewalls 382 and 384. As can be appreciated, during use, the femoral component 316 can rotate about the hinge pin 396.

Figure 19:
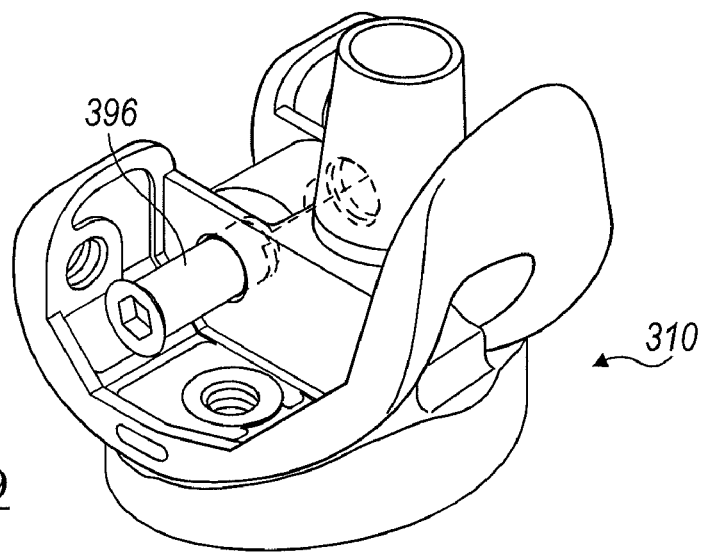
Figure 20:
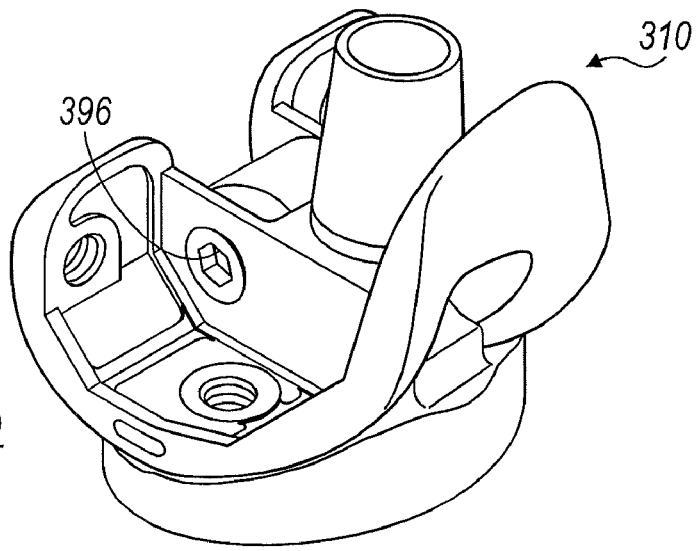
Figure 21:
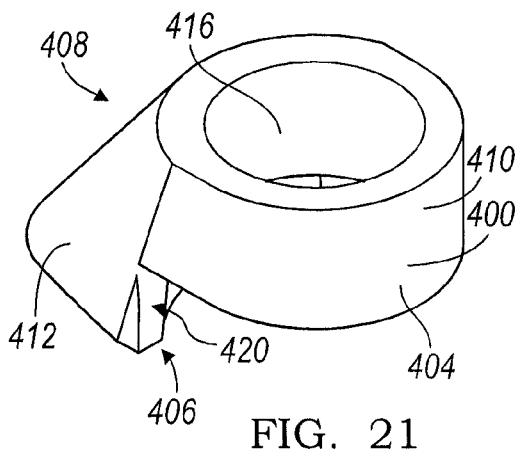
FIG. 21 is a perspective view of a first augment according to the present teachings.
Figure 22:
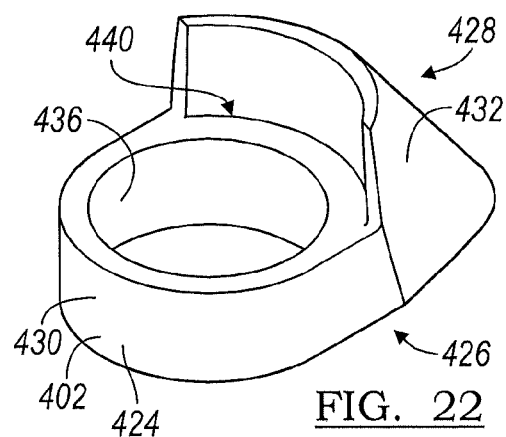
FIG. 22 is a perspective view of a second augment according to the present teachings.

With reference to FIGS. 17-20, an exemplary sequence of assembling the femoral component and bearing is shown. FIG. 17 illustrates an exploded view of the respective femoral component 310, hinge pin 396 and bearing 314. As viewed in FIG. 18, the femoral component 310 is placed onto the bearing 314 such that the respective passages 372 and 388 are aligned. FIGS. 19-20 show the hinge pin 296 inserted into the passages 372 and 388.

With reference now to FIGS. 21-25 a plurality of exemplary augments for use with any of the knee joint prostheses described above will be explained in detail. FIGS. 21-23B illustrate a first pair of augments 400 and 402. The first augment 400 can generally define a body 404 having first end 406 and a second end 408. The body 404 can further define a consistent radius portion 410 at the second end and 408 an outwardly tapered radially extending portion 412 near the first end 406. The consistent radius portion 410 can define a tapered receiving bore 416 formed therethrough. The receiving bore 416 can taper from the first end 406 to the second end 408. A first step 420 may be formed in the body 404 between the consistent radius and the radially extending portions 410 and 412, respectively. As can be appreciated, a collection of first augments may be provided having various dimensions and configurations suitable for a particular patient.

The second augment 402 can generally define a body 424 having first end 426 and a second end 428. The body 424 can further define a consistent radius portion 430 at the first end 426 and an outwardly tapered radially extending portion 432 near the second end 428. The consistent radius portion 430 can define a tapered receiving bore 436 formed therethrough. The receiving bore 436 can taper-from the first end 426 to the second end 428. A second step 440 may be formed at the second end 428 between the consistent radius and the radially extending portions 430 and 432, respectively. As can be appreciated, a collection of first augments may be provided having various dimensions and configurations suitable for a particular patient.

Figure 23A:
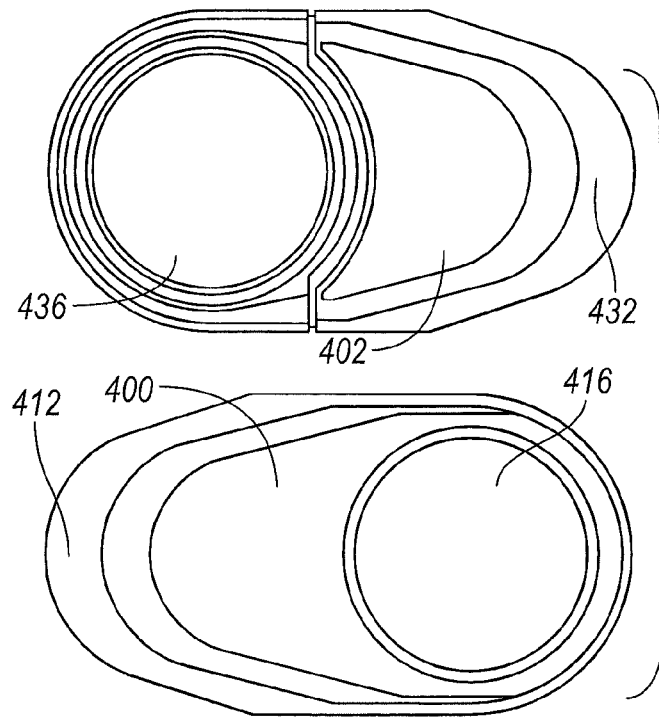
FIG. 23A is a plan view of the first and second augments of FIGS. 21 and 22.
Figure 23B:
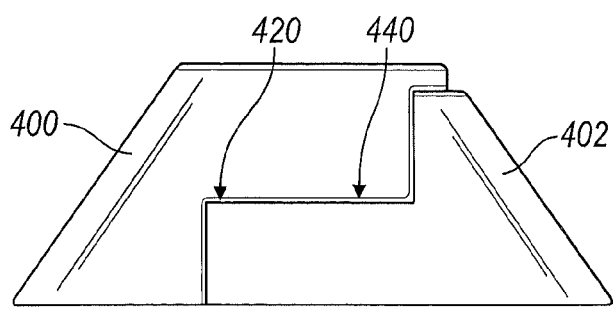
FIG. 23B is side view of the first and second augments in an mated or interlocked position.
Figure 28:
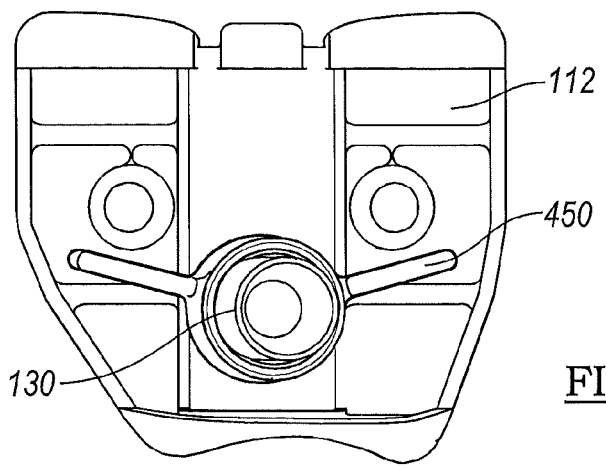
FIG. 28 is a superior view of the femoral component of FIG. 27 and shown with the augment of FIG. 24 secured to an inferiorly extending portion.

As will be described in detail later, the first and second augments 400 and 402 may be used singly or as a combination. As shown in FIG. 23B, the first and second augments 400 and 402 can interlock or mate at the first and second steps 420 and 440 when used concurrently with any of the tibial and femoral components described above.

With reference now to FIGS. 24 and 25, a third augment 450 is shown. The third augment 450 can generally define a body 452 having a first end 454 and a second end 456. The body 452 can further define a pair of wing portions 460 extending radially therefrom to provide rotational stability to either the femoral component or the tibial component. In one example, the wing portions 460 may be offset toward the first end 454. The body 452 can define a tapered receiving bore 464 formed therethrough. The receiving bore 464 can taper from the second end 456 to the first end 454.

According to the teachings of the present disclosure, the receiving bores 416, 436 and 464 of each of the augments 400, 402 and 450 can be slidably press-fit onto any of the inferior extensions of the tibial trays described above. More specifically, the receiving bores can define a tapered interlock with the tapered augment receiving surfaces of the inferior extensions of the tibial trays. Likewise, any of the same augments can also be slidably press-fit onto any of the superior extensions of the femoral components described above. More specifically, the receiving bores can define a tapered interlock with the tapered augment receiving surfaces of the superior extensions of the femoral components. As such, the respective tapered surfaces can cooperate to form a Morse taper.

To illustrate this compatibility, a second augment 402 is shown secured to the superior extension 130 of the femoral component 112 (FIG. 26). If a surgeon desires to account for additional bone loss, the first augment 400 may also be advanced onto the superior extension 130 of the femoral component 112 (FIGS. 27 and 29). As shown, the respective first and second steps 420 and 440 cooperate to mate or form an interlock.

Figure 30:
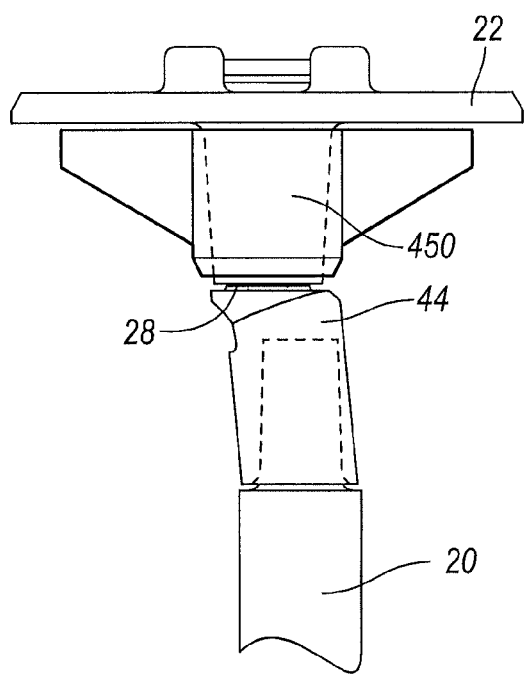
FIG. 30 is an anterior view of the tibial component of FIG. 1 shown with the third augment assembled on the inferiorly extending portion.

With reference to FIG. 29, a first and second augment 400 and 402 are shown secured to the inferior extension 28 of the tibial tray 22. Notably, the first and second augments 400 and 402 may be used with or without the adapter. It is appreciated, that any of the augments may be used with or without the adapter assemblies described above. FIG. 30 illustrates the third augment 450 secured to the inferior extension 28 of the tibial tray 22.

Figure 31:
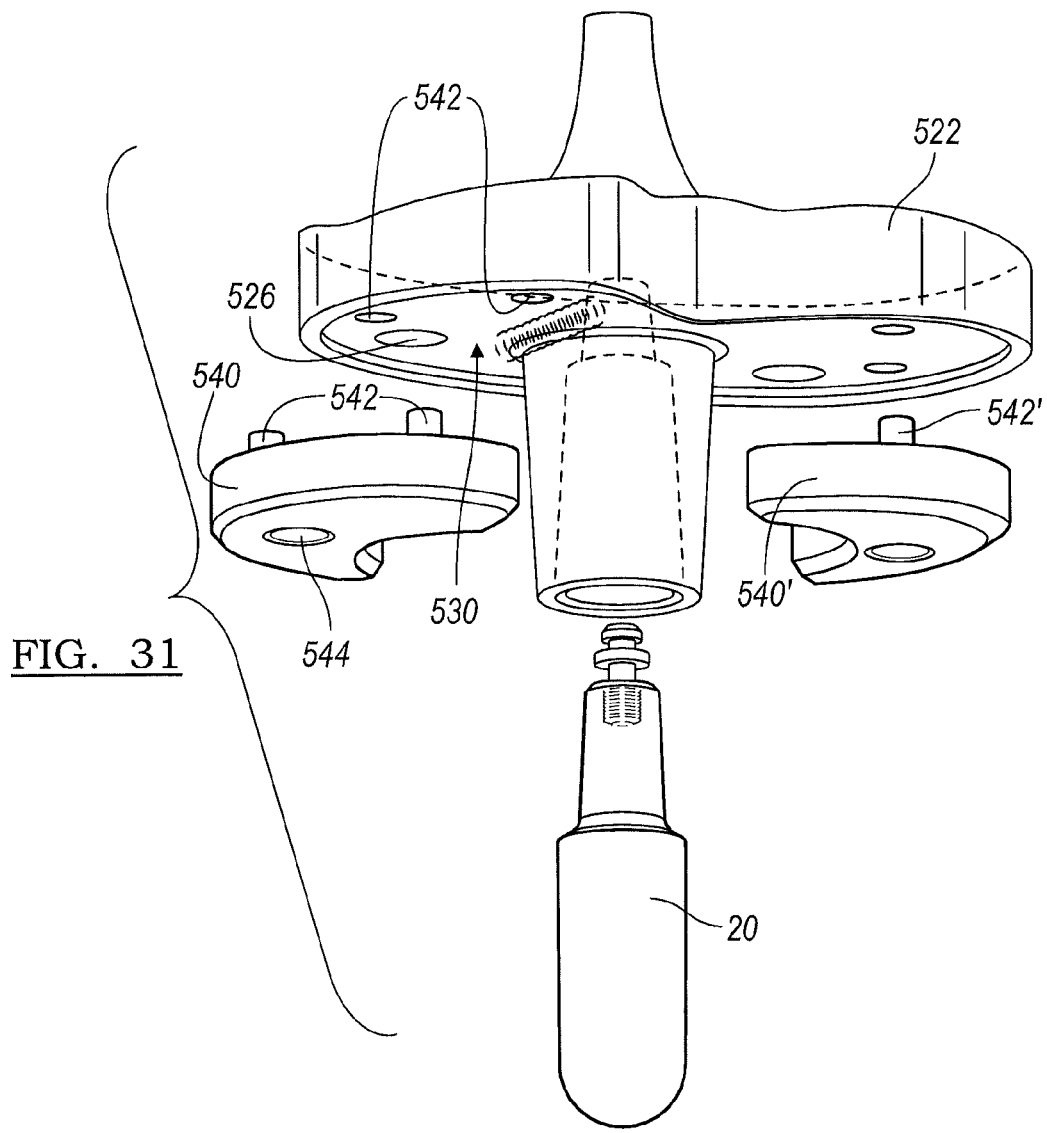
FIG. 31 is an exploded view of a modular tibial component according to additional features.
Figure 32:
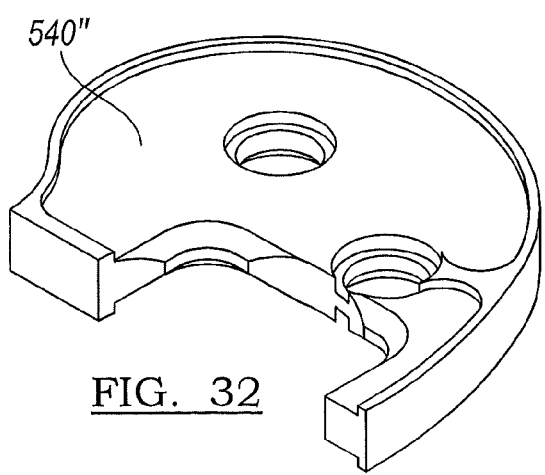
FIG. 32 is a perspective view of an augment according to additional features.

Turning now to FIGS. 31 and 32, another tibial component 522 is shown. The tibial component 522 can define one or more (such as a pair) of blind bores 524 and at least one opening 526 formed on an inferior surface. A recessed portion such as pocket 530 may also be optionally formed on an inferior surface of the tibial component 522. An augment 540 can define one or more (such as a pair) of complementary locating pegs 542 and at least one complementary opening 544. The augment 540 can be adapted to secure onto the inferior surface of the tibial component 522 to compensate for bone loss. As can be appreciated, an augment may be provided on one of a lateral or medial portion, or both, of the tibial component 522. During assembly, the locating peg 542 may nest within a blind bore 524. A fastener (not shown) may be inserted through the respective openings 526 and 544. Another augment 540' having at least one peg 542' can be provided for the opposite of the medial and lateral sides of the inferior surface of the tibial component 522. In another example (FIG. 32), an augment 540" suitable for connecting to either of the medial and lateral sides is provided. In such an example, pegs (such as pegs 542, FIG. 31) need not be provided. As can be appreciated, a plurality of augments 540 can be provided having various thicknesses such that a surgeon can assemble a particular augment suitable for a given patient. A stem 20 can be fixedly accepted into a female tapered extending portion 560 of the tray.

Figure 33:
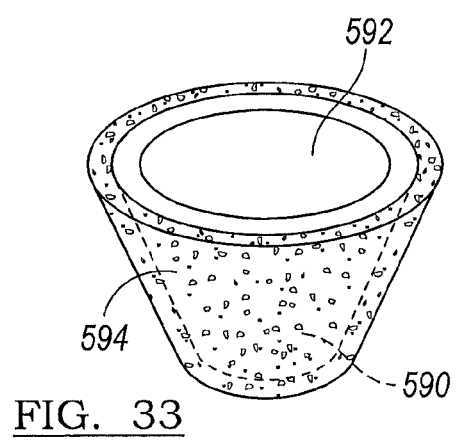
FIG. 33 is a perspective view of another augment according to the present teachings.
Figure 34:
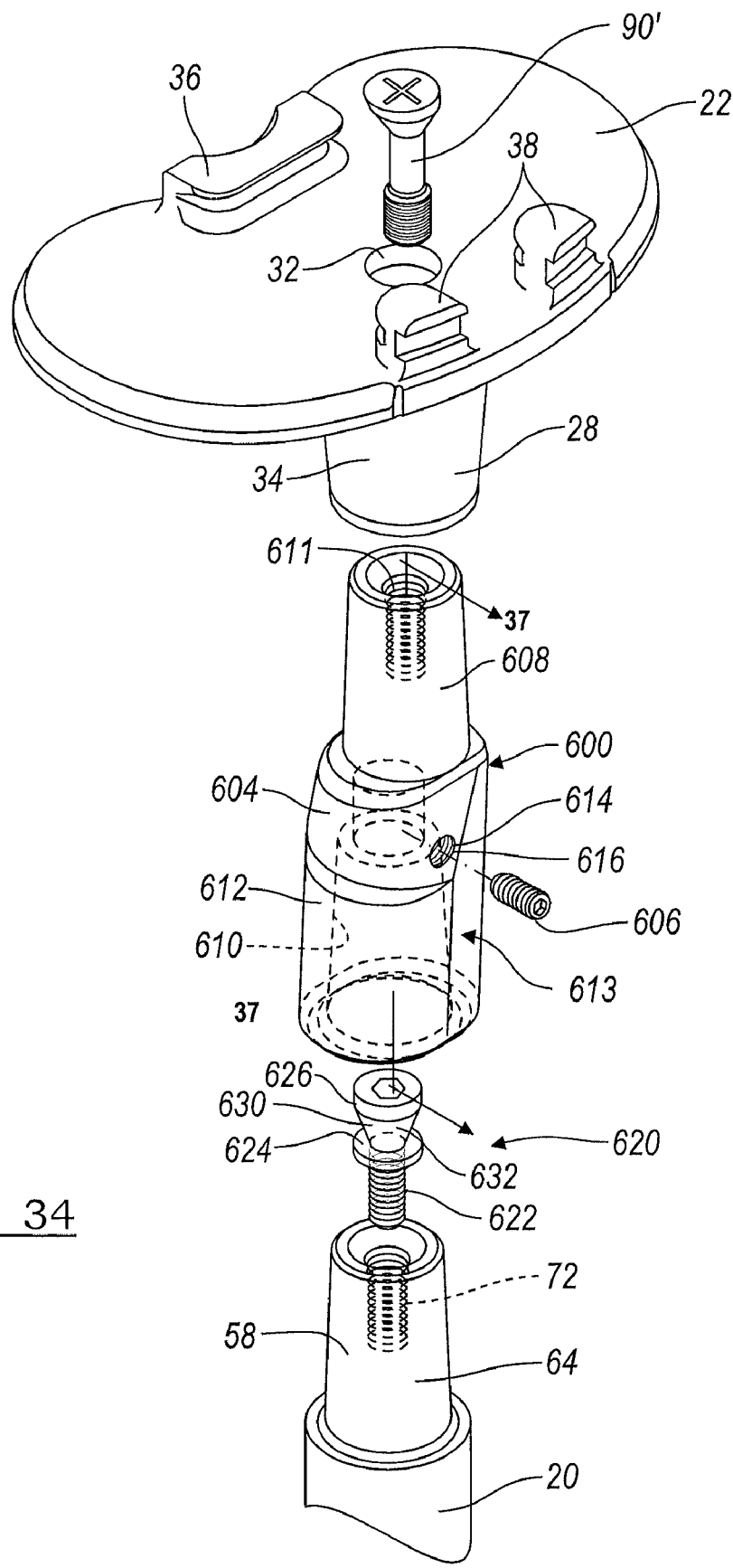
FIG. 34 is an exploded perspective view of an adapter assembly according to additional features and shown with an exemplary tibial component and stem.

FIG. 33 illustrates another augment 590 that defines a tapered receiving bore 592 formed therethrough. The tapered receiving bore 592 can be slidably press-fit onto any of the inferior extensions of the tibial trays and/or the superior extensions of the femoral components described above. A portion of the augment 590 can optionally be formed of porous metal 594. The porous metal 594 can comprise porous titanium alloy for example. The augment 590 can define an inner solid metal sleeve portion and an outer porous metal sleeve portion 594. Again, according to the present teachings, the respective femoral components, tibial components, bearings and/or augments may be part of a kit wherein a surgeon may intra-operatively select a desired component or components needed for a particular patient.

Turning now to FIGS. 34-36B, the modular tibial component 22 (as described above with respect to FIGS. 1-3A) is shown cooperating with an adapter assembly 600 according to additional features. The adapter assembly 600 can cooperate with the stem 20. In a manner which will be discussed more fully below, the adapter assembly 600 can connect the tray 22 and the stem 20 so as to provide an offset to the stem 20 in the transverse or coronal plane or in any other plane. Explaining further, when the stem 20 is attached to the tray 22 through the first adapter assembly 600, the central axis 25 of the stem 20 can be offset from the central axis 27 of the inferiorly extending portion 28 of the tray 22. In the embodiment illustrated, the adapter assembly 600 can provide a first offset of approximately 5 mm. It is appreciated that the offset can range from 0 mm to approximately 5 mm or more and can be in any rotational direction relative to the central axis 27. In other words, the offset axis 25 can be rotated 360 degrees relative to the central axis 27 to provide the surgeon with various intra-operative options to select depending on the patient's needs. Alternatively, the adapter assembly 600 or stem 20 can be rotational keyed to provide only a limited range of adjustment, such as providing only a single offset or two offset positions.

With continued reference to FIGS. 34-36D and additional reference to FIGS. 37-39B, the adapter assembly 600 can generally include an adapter body 604 and a locking member or element 606. The adapter body 604 of the adapter assembly 600 can define a male tapered insertion portion 608 and a female tapered receiving portion 610. The male tapered insertion portion 608 can define a threaded bore 611. The female tapered receiving portion 610 can be formed in an offset body portion 612 of the adapter body 604 for receiving a male tapered insertion portion 58 of the stem 20. The adapter body 604 can define flats 614 on an outer surface for gripping and facilitating alignment as will be described. A skirt (not shown), similar to the skirt 54 formed on the adapter body 44 illustrated in FIG. 2, can be defined at a transition between the male tapered insertion portion 608 and the offset body portion 612. A non-skirted transition can alternatively be formed as shown herein. A bore 614 can be defined from an outer surface of the adapter body 604 to the female tapered receiving portion 610. The bore 614 can define threads 616 that threadably receive the locking member 606.

Figure 37:
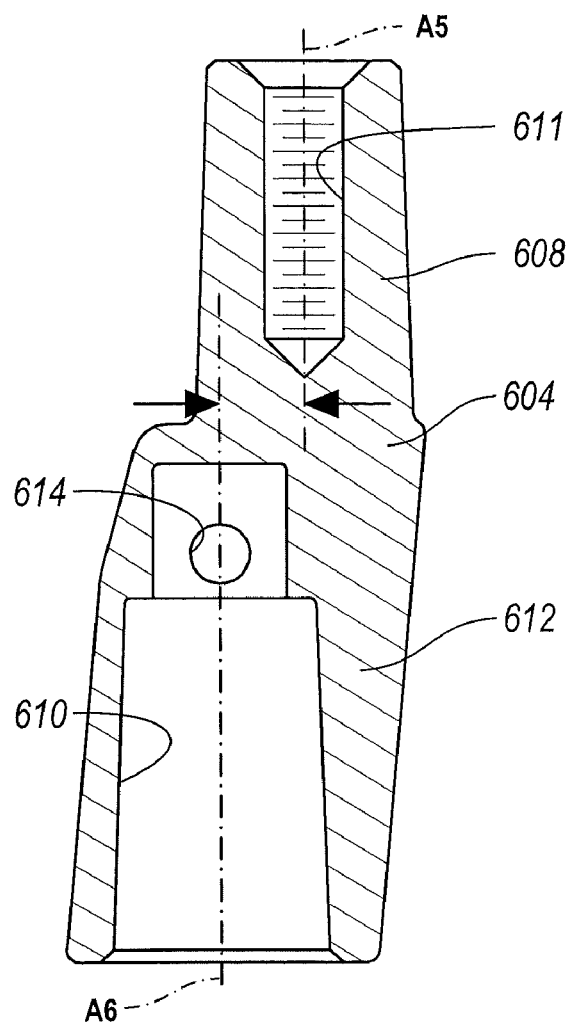
FIG. 37 is a sectional view of an exemplary adapter having a first offset.
Figure 38:
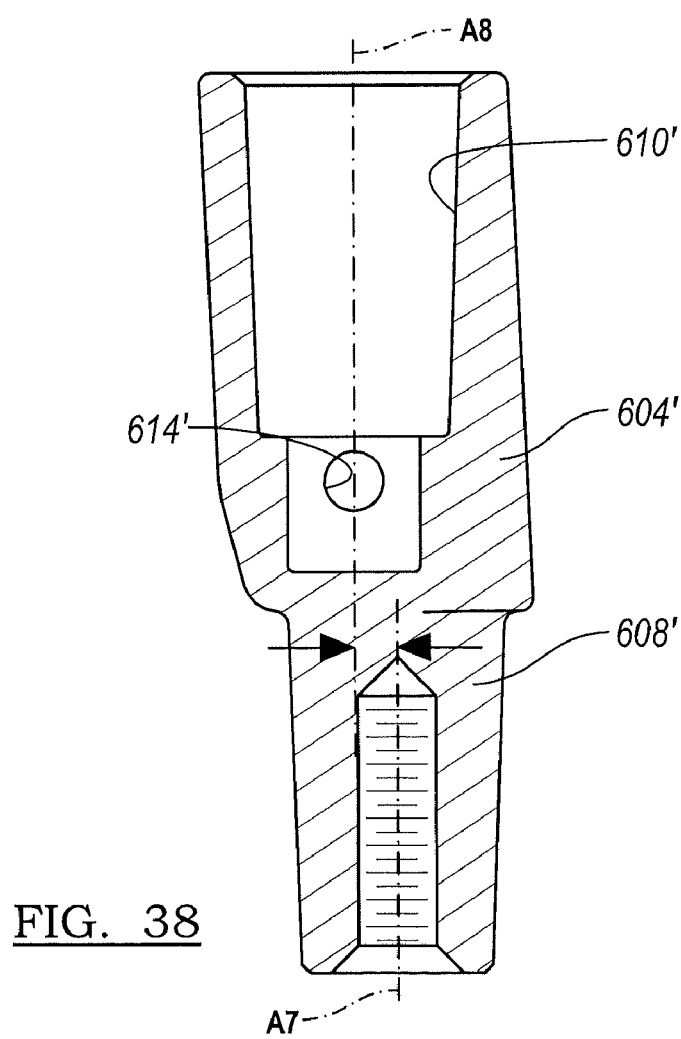
FIG. 38 is a sectional view of another exemplary adapter having a second offset.

With reference to FIG. 37, the male tapered insertion portion 608 of the adapter body 604 defines a first axis $A_5$ and the female tapered receiving portion 610 defines a second axis $A_6$. Further, in the embodiment illustrated, the first axis $A_5$ and the second axis $A_6$ are parallel to one another and spaced apart to provide the desired offset. In this regard, multiple adaptors each having a different offset can be provided to provide the surgeon with intra-operative selection depending on the patient's needs. Insofar as the adapter body 604 provides a 5 mm offset, the first and second central axes $A_5$ and $A_6$ are spaced apart 5 mm. Again, the adapter body 604 can define axes having an alternate offset. In one such alternate configuration, an adapter body 604' (FIG. 38) includes a male tapered insertion portion 608' that defines a first axis $A_7$ and the female tapered receiving portion 610' that defines a second axis $A_8$. The adapter body 604' can define an offset of 2.5 mm.

The male tapered insertion portion 608 can taper slightly as it extends away from the adapter body 604. The female tapered receiving portion 610 similarly tapers slightly as it extends into the adapter body 604 from an end of the adapter body 604. As will become appreciated from the following discussion, various male tapered insertion portions (such as portion 608) can be inserted in various female tapered receiving portions (such as portion 610) to form a locking taper or Morse taper. In a manner to be described further below, the locking member 606 can extend into the bore 614 where it ultimately engages a fastener insert 620.

The fastener insert 620 can include a distal portion 622 which can be externally threaded for engaging the internally threaded aperture 72 of the male tapered insertion portion 58 of the stem 20. The fastener insert 620 can further include a central portion 624 and a proximal portion 626. The proximal portion 626 can define a conical engaging head 630. A gripping detail 632 (such as, but not limited to, a hex-bore for receiving an Allen wrench), can be formed in an upper surface of the proximal portion 626. As will be described in more detail, the fastener insert 620, or more specifically the conical engaging head 630 can be formed of a first biocompatible material while the locking member 606 can be formed of a second biocompatible material. The second biocompatible material can be a higher durometer (harder) material than the first biocompatible material.

Figure 36A:
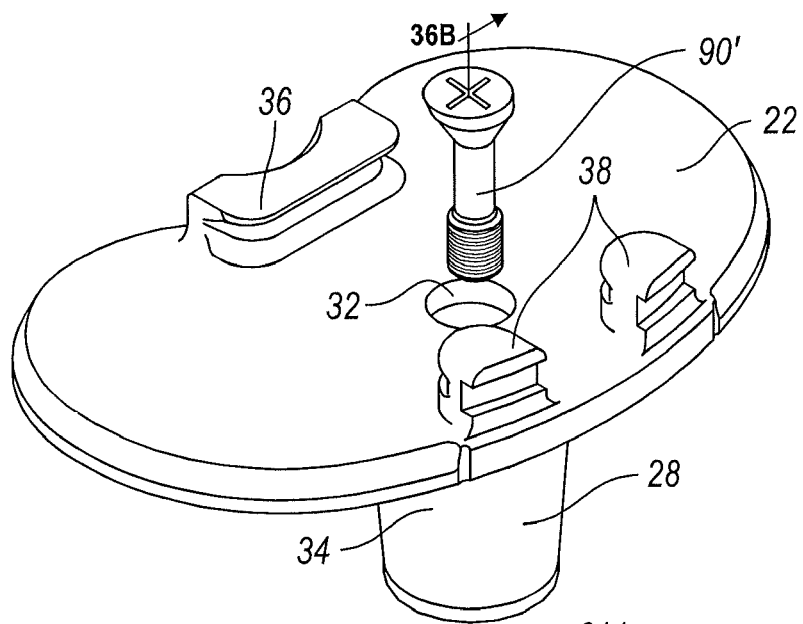
FIG. 36A is a detail exploded view of the tibial tray and adapter illustrated in FIG. 34.
Figure 36B:
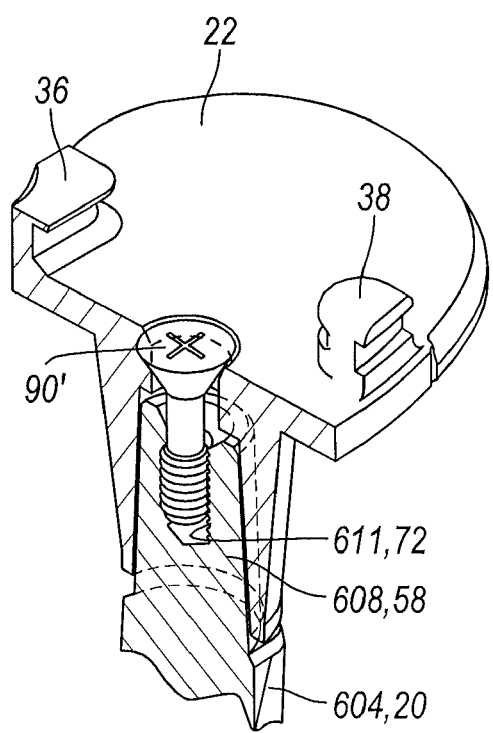
FIG. 36B is a partial sectional view taken along line 36B-36B of FIG. 36A.
Figure 36C:
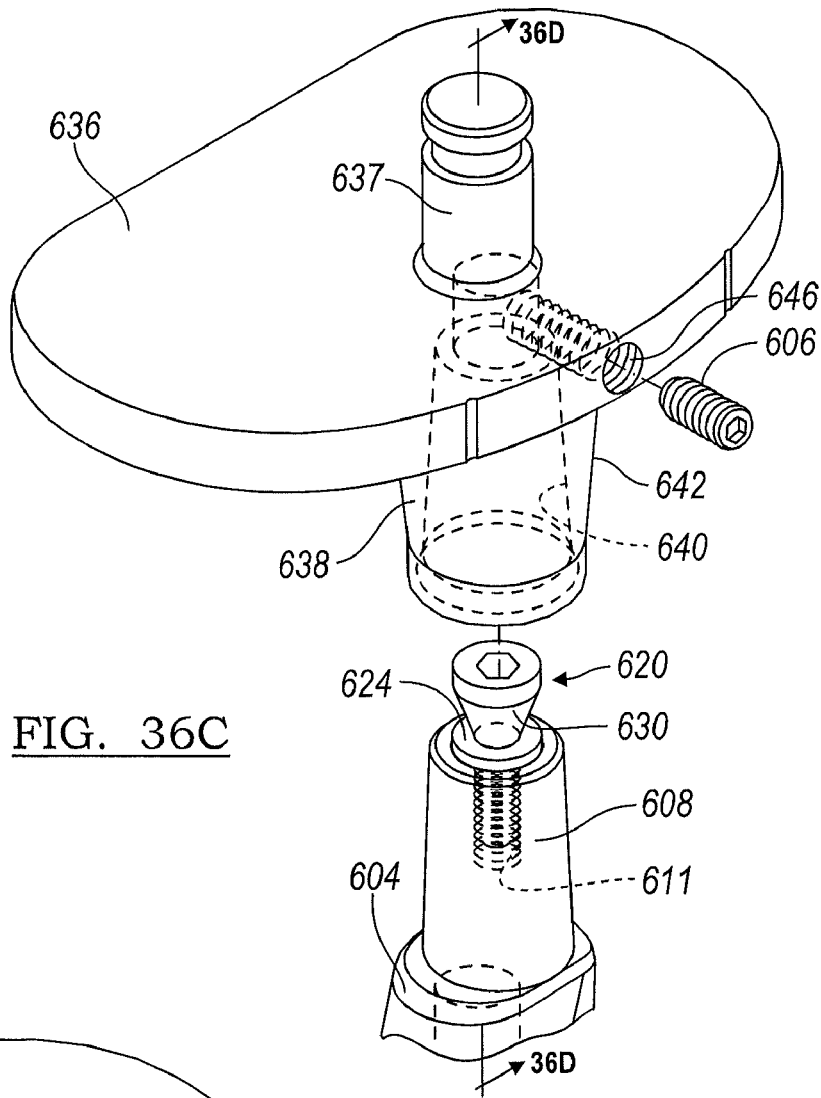
FIG. 36C is a detail exploded view of an adapter assembly cooperating with a tibial component according to additional features.
Figure 36D:
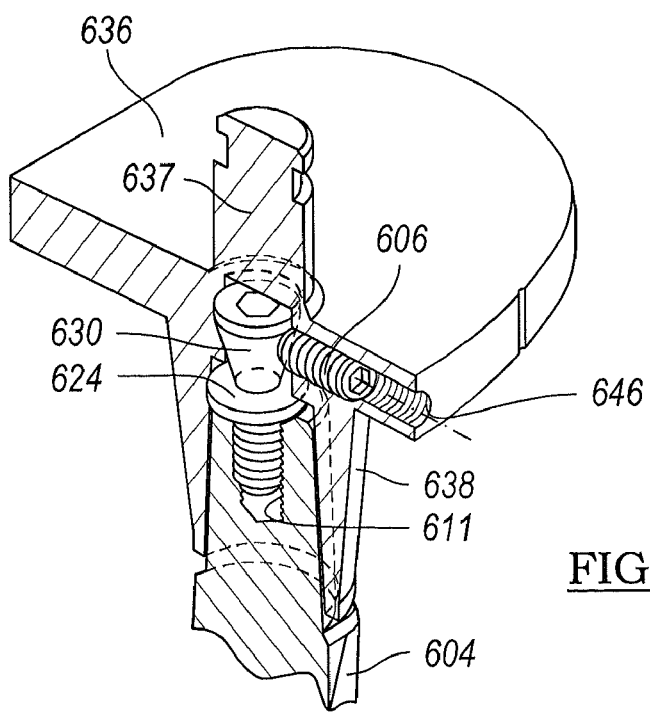
FIG. 36D is a partial sectional view taken along line 36D-36D of FIG. 36C.

Turning now to FIGS. 36C and 36D, a tibial tray 636 according to additional features is shown. As will be described more fully herein, the tibial tray 636 can be part of a bone-conserving hinge knee prosthesis (FIG. 48A). The tibial tray 636 can define a superiorly extending stub 637 and an inferiorly extending portion 638 that defines a female tapered receiving portion 640. The inferiorly extending portion 638 can define an exterior tapered augment receiving surface 642. The tibial tray 636 can define a threaded passage 646 formed through the tray portion of the tibial tray 636. The treaded passage 646 can be adapted to threadably accept the locking member 606. Unlike the cruciate retaining tibial tray 22 (FIG. 34) that provides the central aperture 32 for receiving the fastener 90' in the superior/inferior direction, the tibial tray 636 can provide the threaded passage 646 for receiving the locking member 606 in the anterior/posterior direction.

With reference now to FIGS. 39A-40B, an exemplary sequence of assembling the tibial tray 636, the adapter body 604, and the stem 20 will be described. At the outset, the fastener insert 620 can be threaded into the threaded bore 611. In one example, the fastener insert 620 can be threaded until the central portion 624 engages a terminal surface 650 of the male tapered insertion portion 608 of the adapter body 604. At this point, the stem 20 can be coupled to the adapter body or the adapter body 604 can be coupled to the tibial tray 636. While the order can be reversed, the adapter body 604 can be coupled to the tibial tray 636, by inserting the male tapered insertion portion 608 of the adapter body 604 into the female tapered receiving portion 640 of the tibial tray 636. The surgeon can then rotate the male tapered insertion portion 608 within the female tapered receiving portion 640 to attain the desired orientation. As will be described later, the instant disclosure provides various tools for verifying a correct orientation of the adapter body 604 prior to securing the adapter body 604 in a fixed position relative to the tibial tray 636. Once the desired orientation has been attained, the locking member 606 can be threaded from an unsecured position (FIG. 36C) into engagement with the conical engaging head 630 to a secured position (FIG. 36D).

Figure 39A:
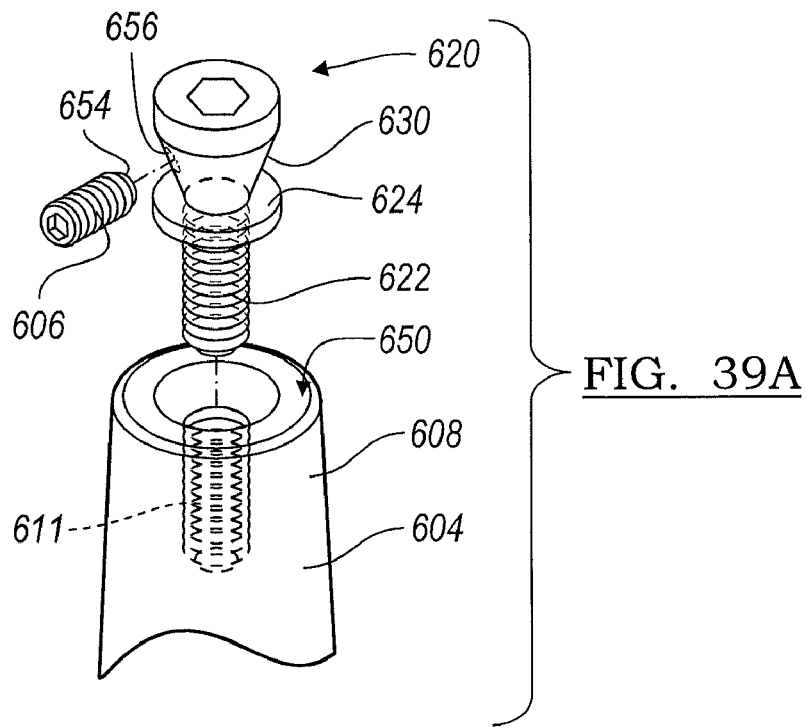
FIG. 39A is an exploded view of a fastener member and insert of the adapter assembly.
Figure 39B:
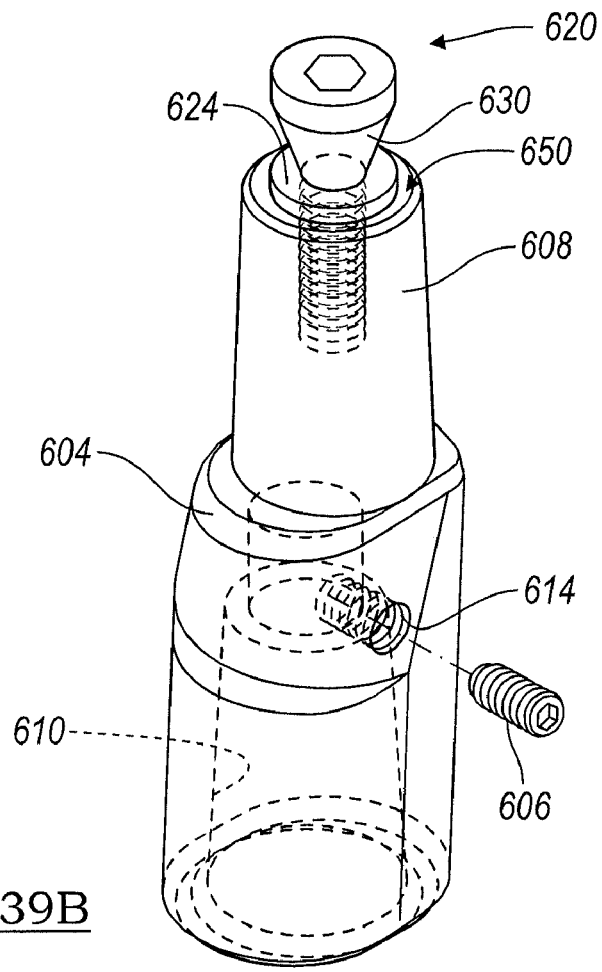
FIG. 39B is a partial exploded view of an adapter assembly.
Figure 40A:
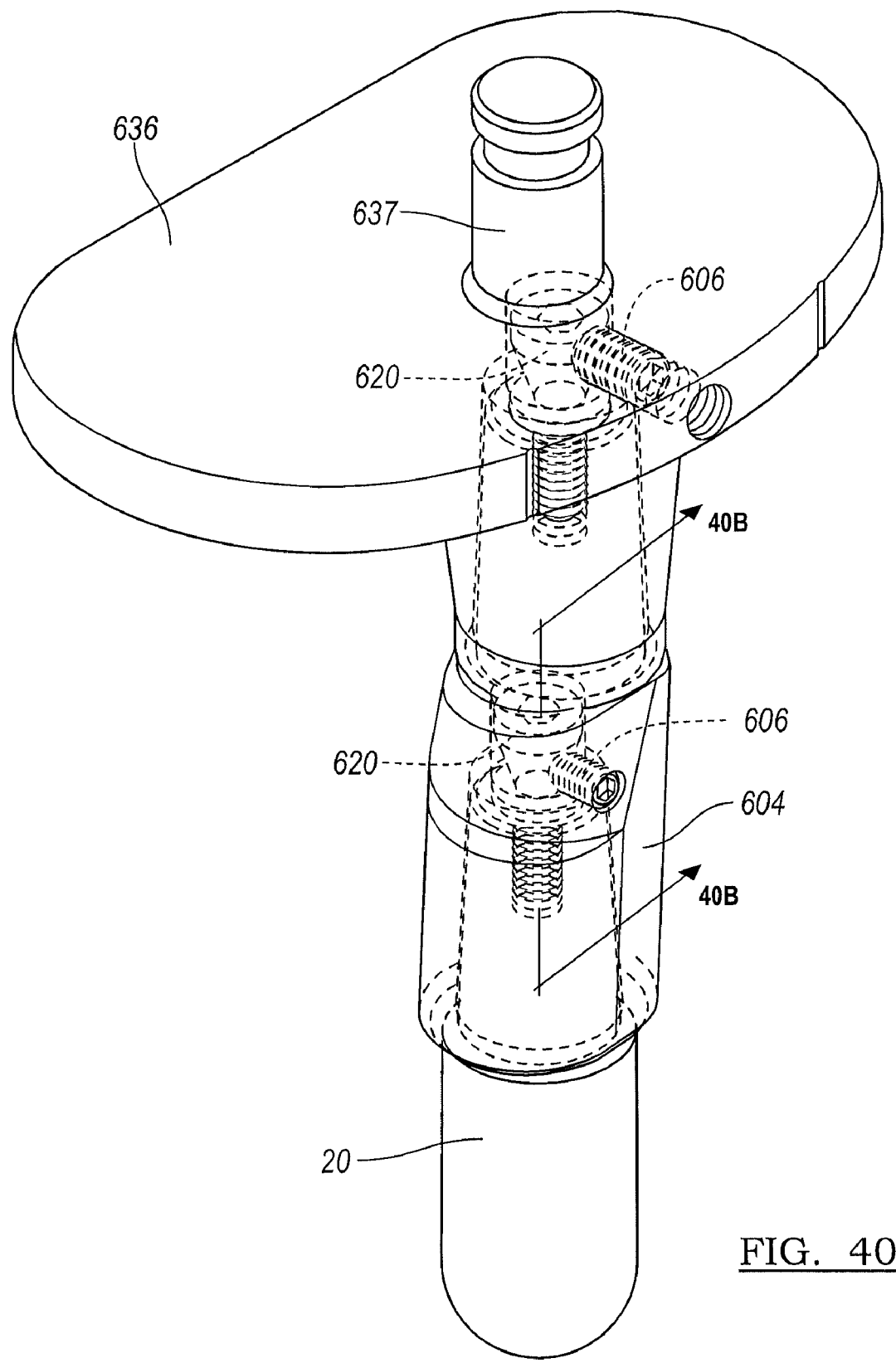
FIG. 40A is an assembled view of a tibial component, adapter assembly and stem according to one example of the present teachings.
Figure 40B:
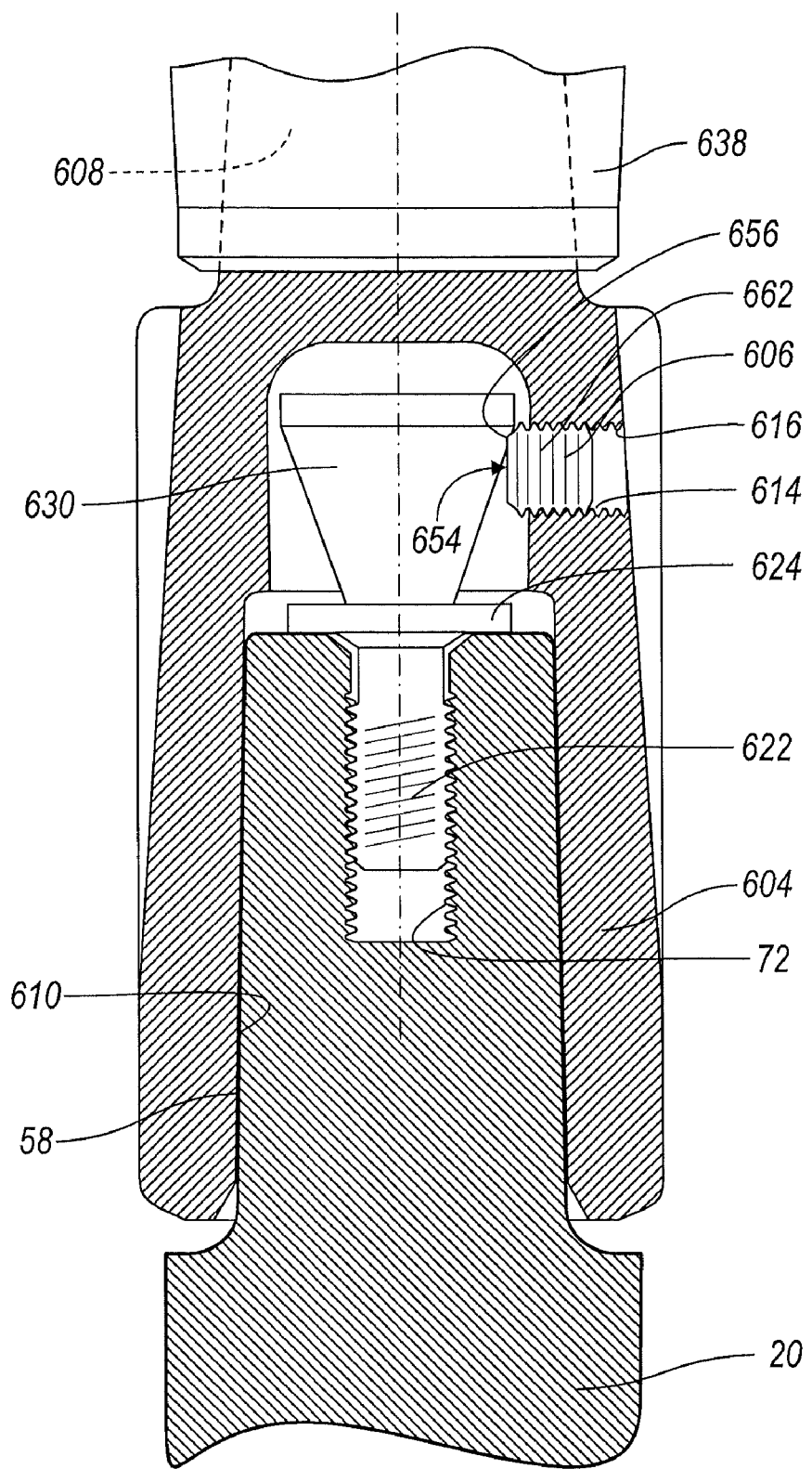
FIG. 40B is a sectional view taken along line 40B-40B of FIG. 40A.

As mentioned above, the locking member 606 can be formed of a biocompatible material that is harder than the fastener insert 620. As a result, a distal end 654 of the locking member 606 can deform (e.g. create a depression at) an interface area of the conical engaging head 630. The deformed area is identified at reference numeral 656 (FIGS. 39A and 40B). By deforming an area 656 of the fastener insert 620, the locking function of the locking member 606 can be improved by providing a greater resistance to separation. Explained further, the resultant depression can inhibit sliding, rotation, or other relative movement between the locking member 606 and the fastener insert 620.

Next, the stem 20 can be coupled to the adapter body 604 by driving the locking member 606 (i.e. another identical locking member 606) into the fastener insert 620 (i.e. another identical fastener insert 620).

According to another feature, the threads 616 defined by the bore 614 can define a thread profile that is slightly different (i.e. pitch) than threads 662 defined by the locking member 606. Alternatively, one of the threads 616 or 662 can be deformed initially. Such a relationship can allow the locking member 606 to be retained within the bore 614 upon initial handling by a surgeon. In other words, the locking member 606 can already by positioned within the bore such that the surgeon would not need to locate the distal tip 654 of the locking member 606 into the bore 616 (i.e. mate two separate components). It is appreciated that such thread configuration would not preclude rotation of the locking member 606 within the bore 616 during fastening.

Figure 41A:
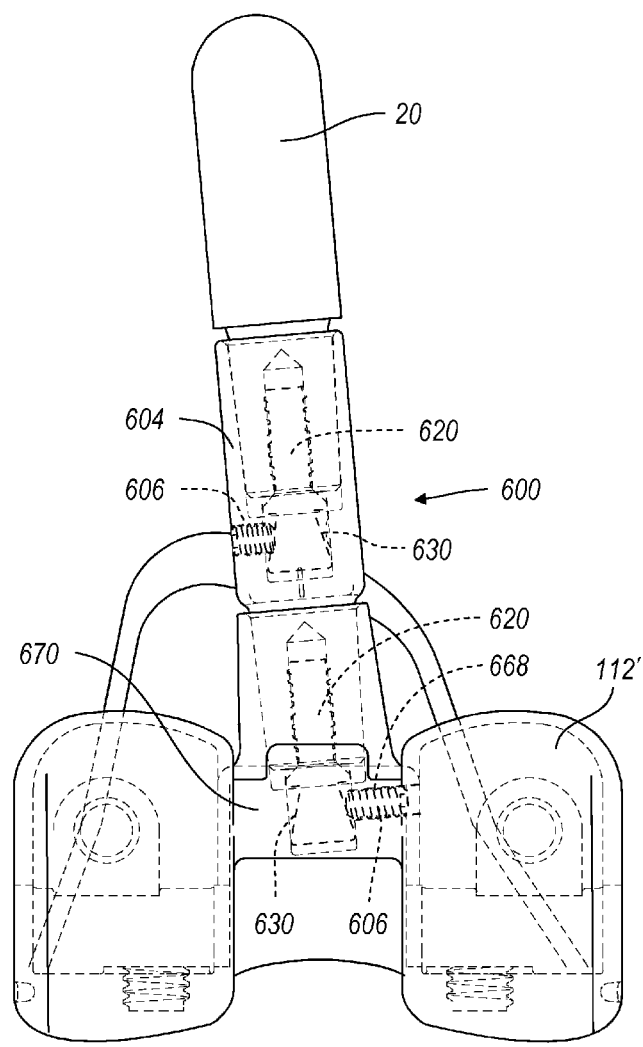
FIG. 41A is an assembled view of an exemplary femoral component, adapter assembly and stem according to one example of the present teachings.

Turning now to FIG. 41A, the adapter assembly 600 including the adapter body 604 and the locking member 606 are shown assembled with a femoral component 112'. The femoral component 112' is substantially similar to the femoral component 112 (FIG. 8), but can define a threaded bore 668 formed in a femoral box 670. As can be appreciated, the threaded bore 668 can provide a similar function to the threads 616 of the bore 614 of the adapter body 604. As a result, a locking member 606 can be driven to engage a conical engaging head 630 of fastener insert 620.

Figure 41B:
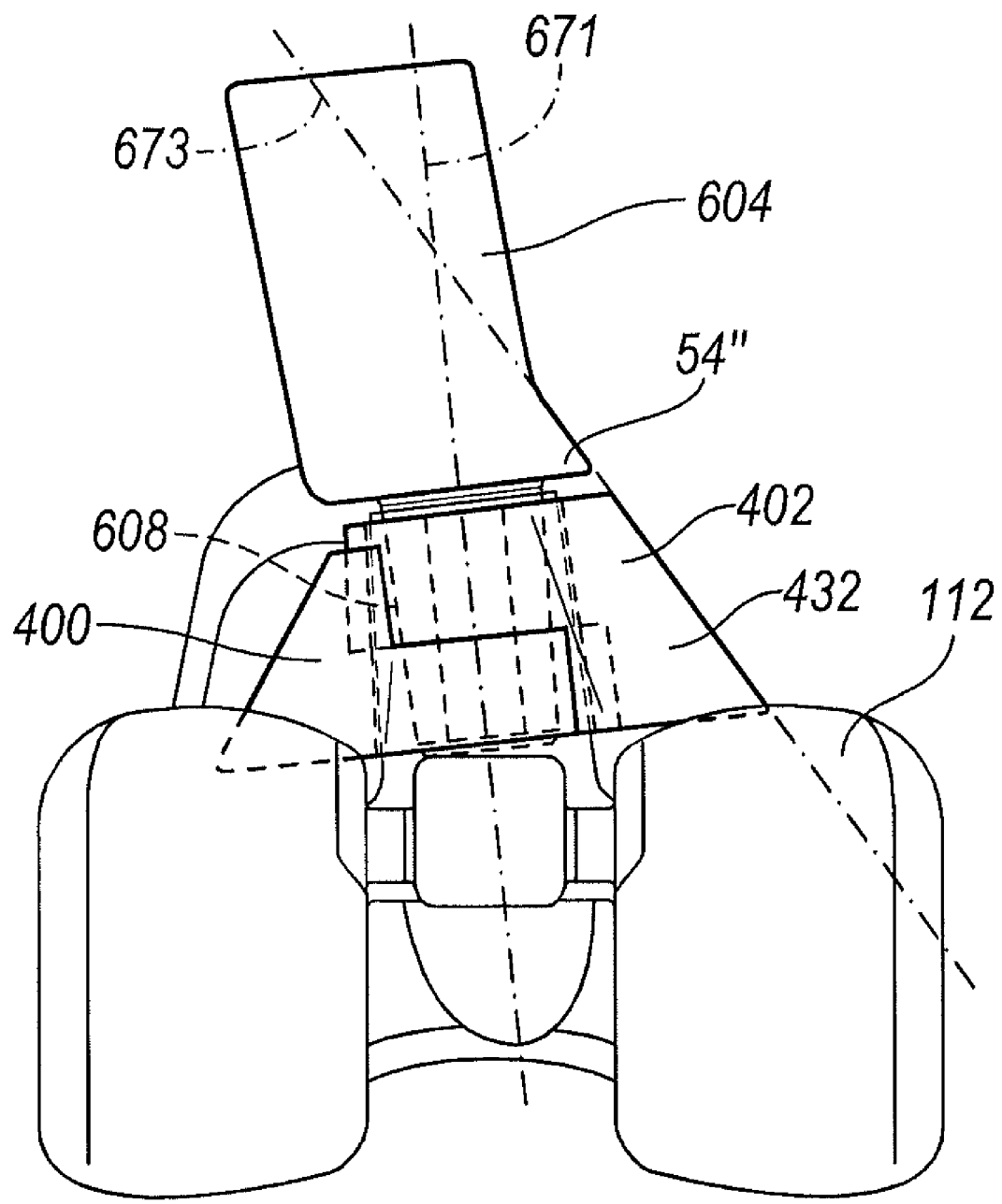
FIG. 41B is an assembled posterior perspective view of a pair of interlocking augments, adapter assembly and femoral component according to one example of the present teachings.
Figure 42:
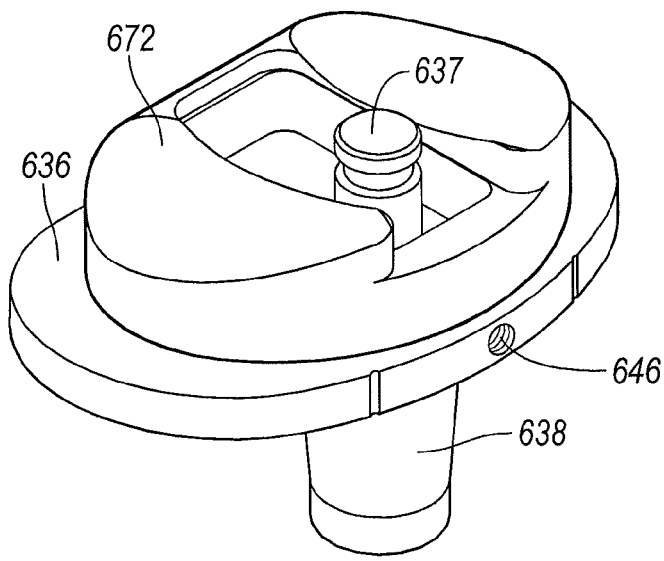
FIGS. 42-45 are perspective views of various tibial components and bearings used in cooperation with a bone conserving hinged knee.
Figure 43:
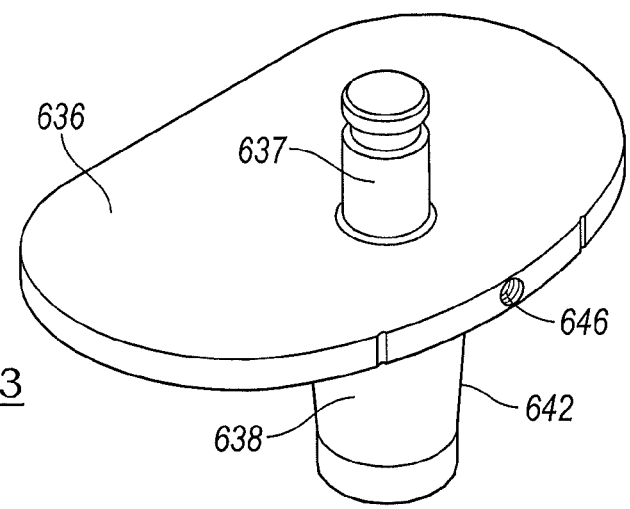
Figure 44:
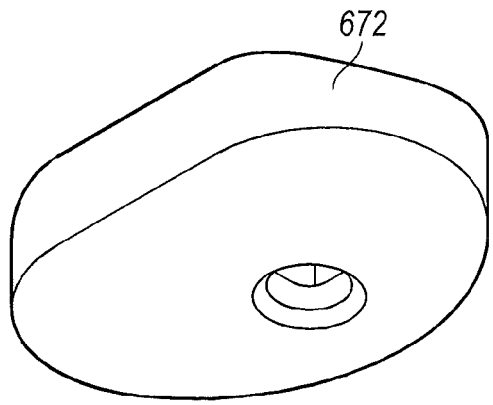
Figure 45:
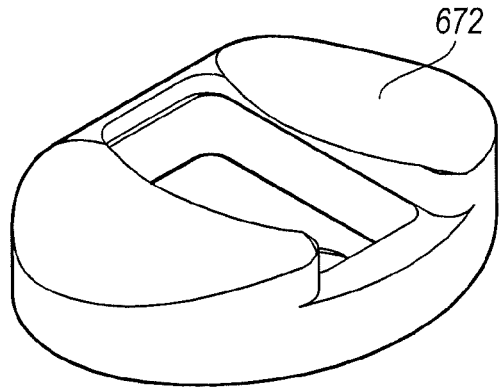
Figure 46:
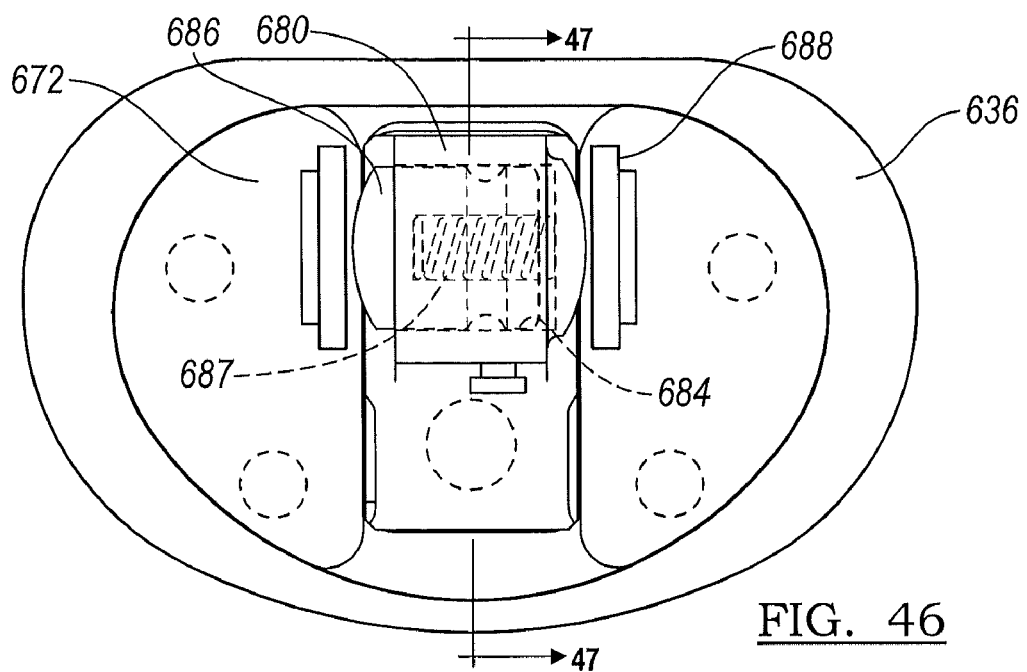
FIG. 46 is a superior view of an assembled hinged knee.
Figure 47:
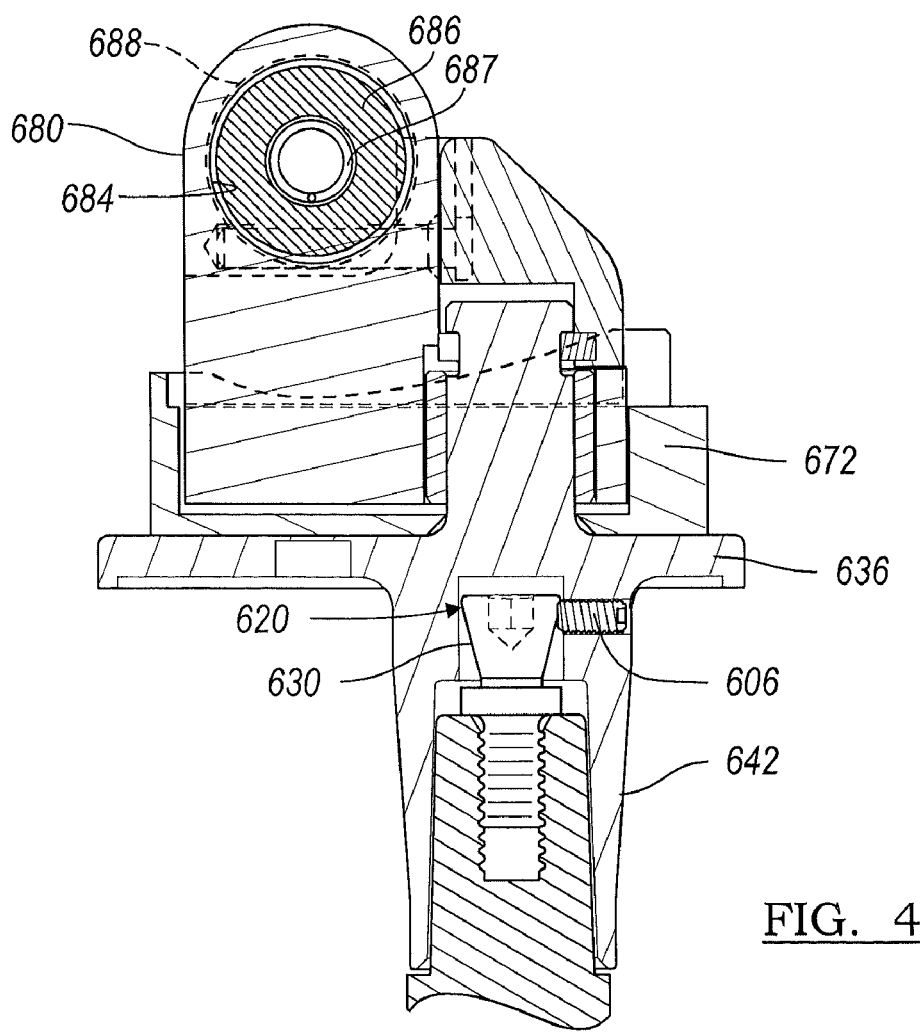
FIG. 47 is a sectional view taken along line 47-47 of FIG. 46.
Figure 49:
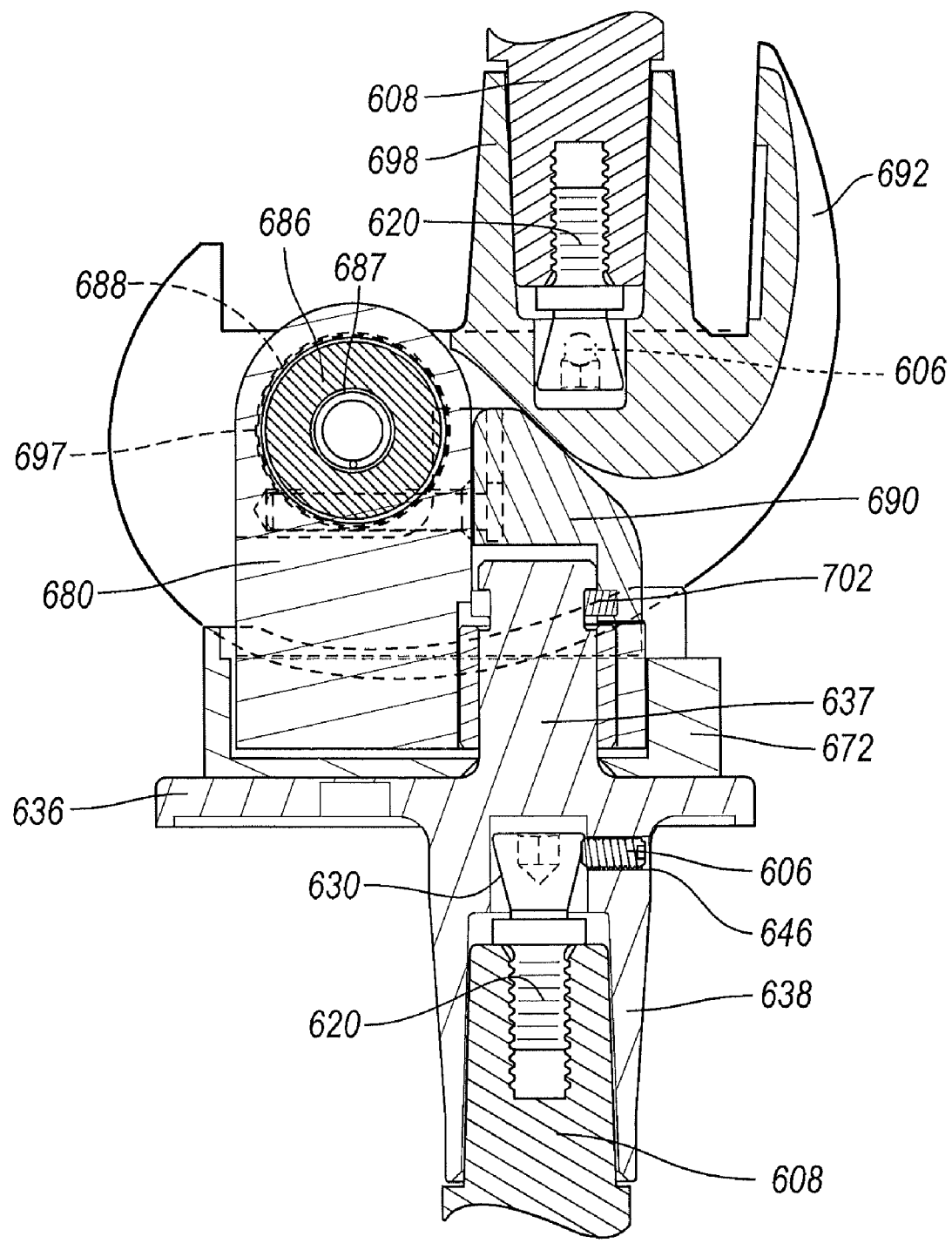
FIG. 49 is a sectional view of the hinged knee prosthesis of FIGS. 48A and 48B shown assembled.
Figure 50:
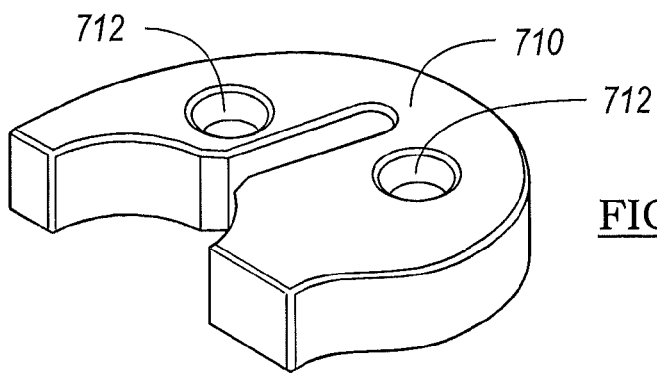
FIGS. 50-54 are perspective views of various augments according to the present teachings.
Figure 51:
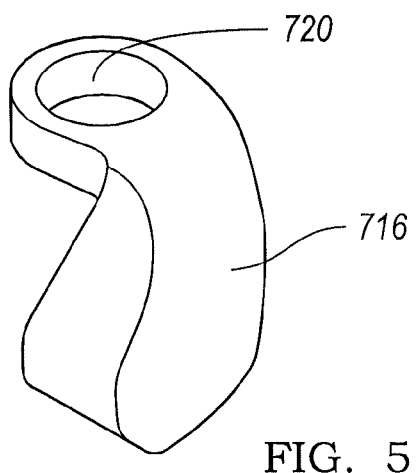
Figure 52:
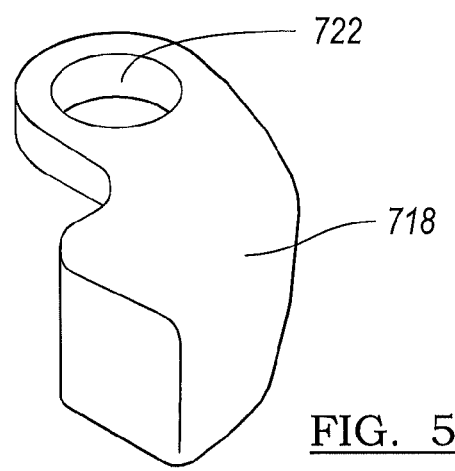
Figure 53:
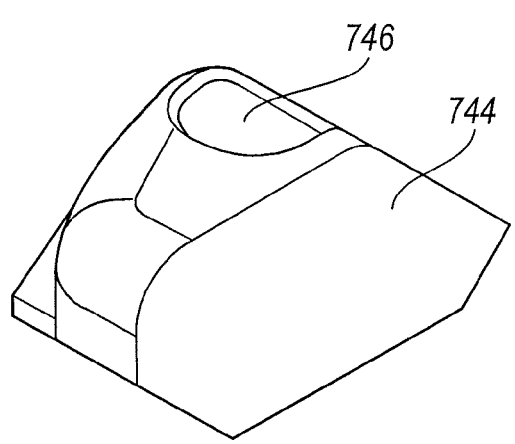

As shown in FIG. 41B, a skirt 54" is shown on the adapter body 604. The skirt 54" generally defines a flared contour portion that can provide a generally smooth geometrical transition onto the outwardly tapered radially extending portion 432 (see also FIG. 21) of the augment 402. The geometrical transition between the skirt 54" and the augment 402 can reduce otherwise sharp transitions between implanted components to provide a favorable nesting configuration with surrounding bone in an implanted position. Explained more specifically, the male tapered insertion portion 608 of the adapter 604 can define an attachment axis 671. The outwardly tapered radially extending portion 432 of the body 424 can define a plane 673. The flared contour portion of the skirt 54" can taper generally along the plane 673 in an implanted position. The skirt 54" can therefore cooperate with the augment 402 to effectively fill bone voids.

Figure 35:
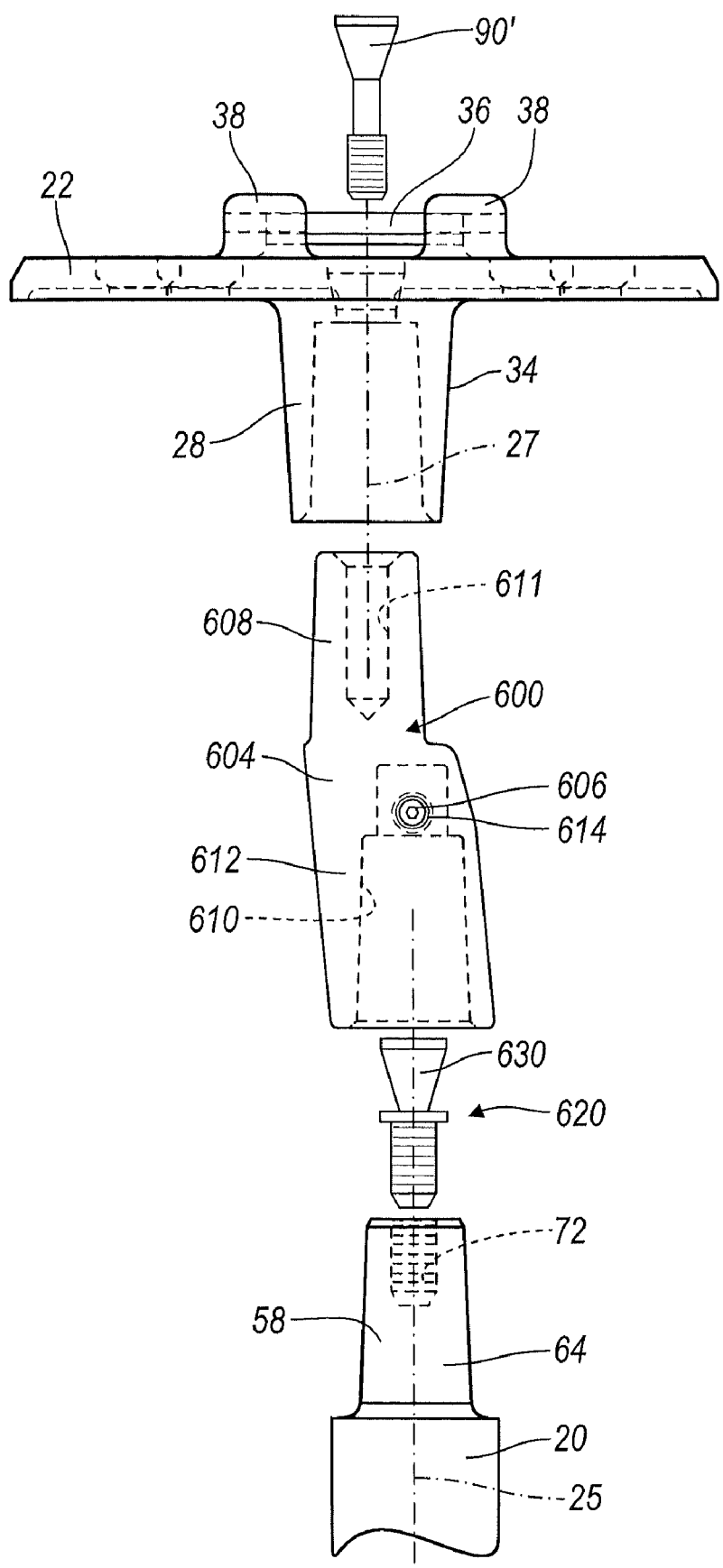
FIG. 35 is an anterior view of the prosthesis illustrated in FIG. 34.

As can now be appreciated, the instant disclosure provides a simplified set of interchangeable components wherein an adapter assembly 600 can be used on either side of the joint line (e.g. with a tibial component, such as described in relation to FIG. 35, and also a femoral component, such as described in relation to FIG. 41). Moreover, the locking member 606 and fastener insert 620 combination can be used in several distinct areas as described above. Additionally, the augments such as disclosed in FIGS. 21-25 can be used in cooperation with either a superiorly extending portion (such as portion 130, FIG. 8) of a femoral component or an inferiorly extending portion (such as portion 638, FIG. 36C) of a tibial component.

Turning now to FIGS. 42-49, additional components that may be used in cooperation with the tibial tray 636 will be described in greater detail. As explained, the tibial tray 636 can be used as part of a bone-conserving hinge knee prosthesis. The tibial tray 636 can cooperate with a bearing 672. A keel 680 can define a first bore 682 for receiving the superiorly extending stub 637, and a second bore 684 for receiving an axle 686. A pair of hubs 688 can engage opposite ends of the axle 686. In one example, a biasing member 687 can bias against an outer surface on the keel 680 to bias the axle 686 outward.

The keel 680 can be intraoperatively coupled to the femoral component 692 by depressing the axle 686 in a direction inwardly and locating the keel 680 generally into the femoral box 696 of the femoral component 692 until the axle 686 aligns with passages 695 and 697 formed in the femoral box. The hubs 688 can nest in the passages 695 and 697 on opposite ends of the axle 686. The axle 686 can bias outwardly encouraging the hubs 688 to seat into the passages 695 and 697. As can be appreciated, during use, the hubs 688 can provide a rotational surface for supporting the axle 686. The hubs 688 can be formed of any suitable bearing material such as PEEK, polyethylene, carbon reinforced PEEK. A pin 700 can then be inserted into the keel 680 to inhibit inward compression of the axle 686.

A shoe 690 can be disposed intermediate of the keel 680 and a femoral component 692. The femoral component 692 can define a threaded bore 694 through the box 696. A superiorly extending portion 698 can receive a male tapered insertion portion 608 of the adapter body 604. The locking member 606 can be used as described above to engage a fastener insert 620 (not specifically shown) extending proud from the male insertion portion 608. Alternatively, a fastener can extend superiorly though the femoral component 692 to securably mate with the adapter body 604 (such as shown in FIG. 8). A horseshoe clip 702 can securably nest in an annular pocket 704 defined on the stub 637.

Figure 58:
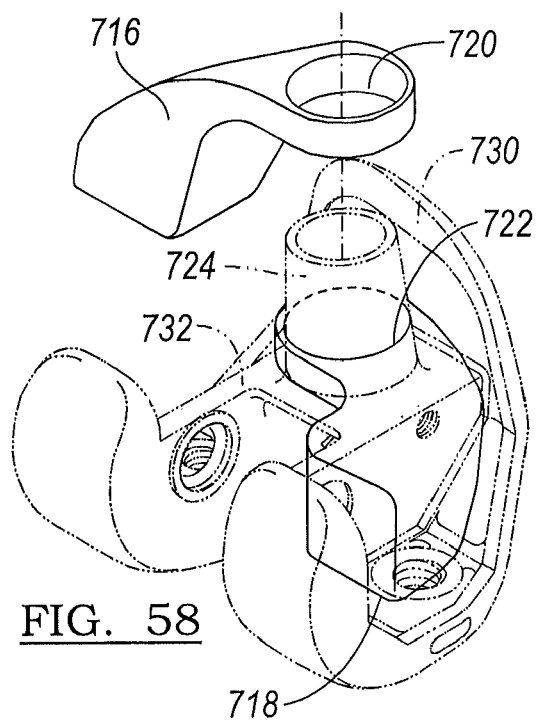
Figure 59:
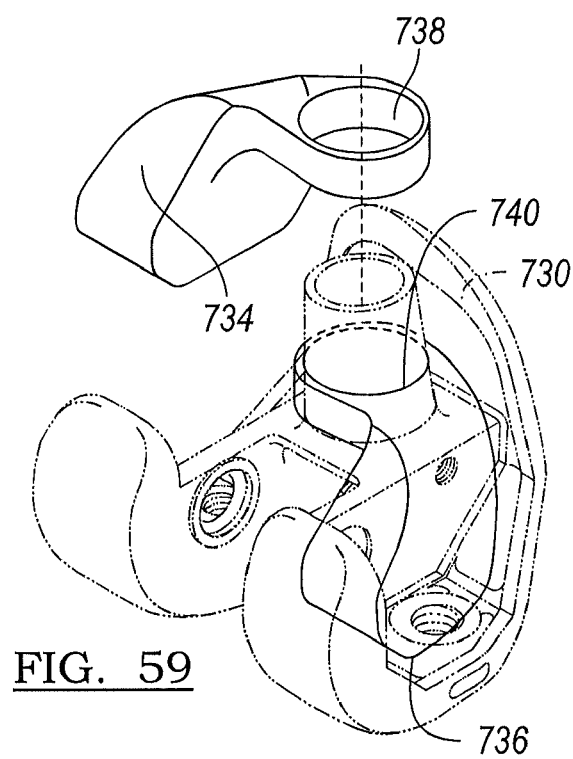

With reference now to FIGS. 50-54, additional augments are shown. An augment 710 can define a substantially symmetric profile for securing to either a medial or lateral inferior side of a tibial tray (i.e. such as a tibial tray 22D, FIG. 3D). Passages 712 can be formed through the augment 710 for receiving a fastener (not shown) in an assembled position. Augments 716 and 718 can define passages 720 and 722, respectively for receiving a superiorly extending portion 724 of a femoral component 730 (see FIG. 58). The augments 716 and 718 can define a profile unique for cooperating with a medial or lateral side of a femoral box 732. The augment 716 can be implanted to occupy an area of bone loss on a medial side of the femoral component 730. The augment 718 can be implanted to occupy an area of bone loss on a lateral side of the femoral component. Augments 734 and 736 can define passages 738 and 740 respectively (FIG. 59). The augments 734 and 736 can be used individually or in combination. The respective passages 720, 722, 738 and 740 and the superiorly extending portion 724 of the femoral component 730 can define conical engaging surfaces that are adapted to provide a friction fit formed by a Morse-type taper. The augments 734 and 736 can define a profile different than the augments 716 and 718.

Returning now to FIG. 53, another augment 744 is shown. The augment 744 can define a passage 746. In one example, the augment 744 can be symmetric for coupling to either a medial or lateral surface of the femoral component 730. Threaded blind bores 750 and 752 can be defined on the femoral component 730 for accepting a fastener (not shown) for securing an augment 744. Another augment 744' can be provided (that can have a mirror image profile relative to the augment 744) for compatibility with only the medial (or lateral) side of the femoral component.

Figure 54:
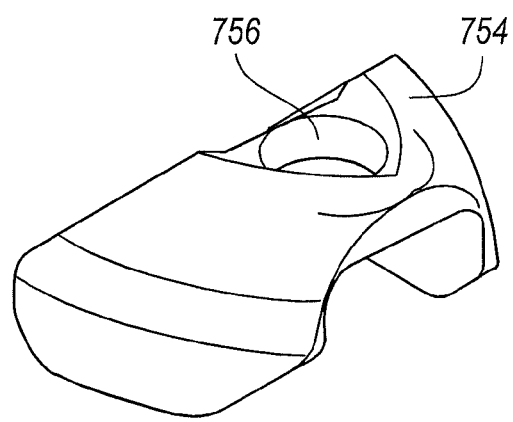
Figure 57:
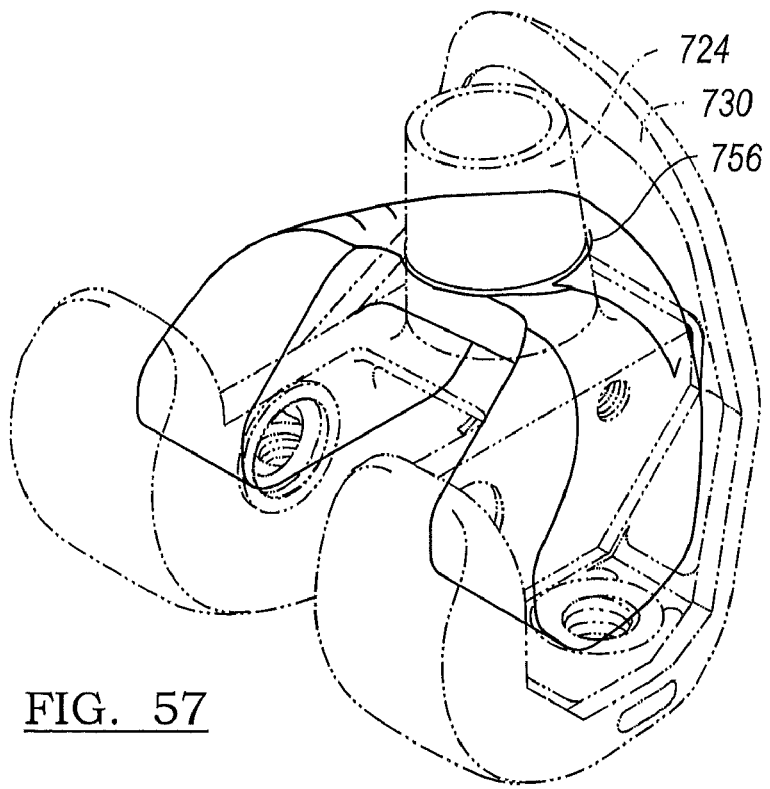
Figure 60:
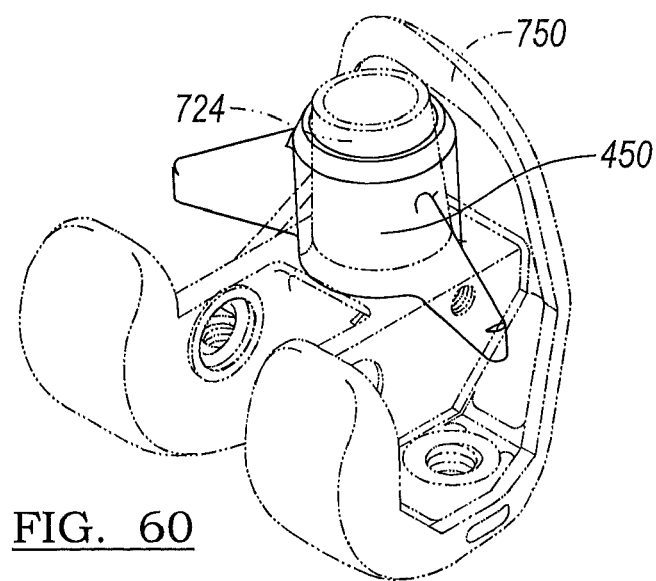

With reference to FIGS. 54 and 57, a saddlebag augment 754 having a central passage 756 is shown. The central passage 756 can receive the superiorly extending portion 724 of a femoral component 730. As with the other augments provided herein, the central passage 756 and the superiorly extending portion 724 can define conical engaging surfaces that are adapted to provide a friction fit formed by a Morse-type taper. FIG. 60 illustrates a femoral component 730 having the winged augment 450 (FIG. 24) secured to the superiorly extending portion 724.

Each of the augments disclosed herein can be formed of biocompatible material such as solid metal, porous metal or a combination of solid metal and porous metal. In one example, the solid metal or porous metal can comprise stainless steel, titanium, titanium alloys, cobalt-chromium alloys and other materials that are suited for use in a biocompatible environment. As is generally known in the art, porous metal can provide a suitable surface area for encouraging ingrowth of natural bone and/or soft tissue. Various compositions and methods of making such porous metal may be found in co-pending applications, U.S. Ser. No. 11/111,123, filed Apr. 21, 2005; U.S. Ser. No. 11/294,692, filed Dec. 5, 2005; U.S. Ser. No. 11/357,868, filed Feb. 17, 2006 each entitled "Method and Apparatus for Use of Porous Implants"; U.S. Ser. No. 11/546,500, filed Oct. 11, 2006, entitled "Method for Use of Porous Implants"; U.S. Ser. No. 11/709,549, filed Feb. 22, 2007, entitled "Porous Metal Cup with Cobalt Bearing Surface"; and U.S. Ser. No. 11/357,929, filed Feb. 17, 2006, entitled "Method and Apparatus for Forming Porous Metal Implants", all of which are also assigned to Biomet, Inc., of Warsaw Ind., which are incorporated herein by reference.

Figure 55A:
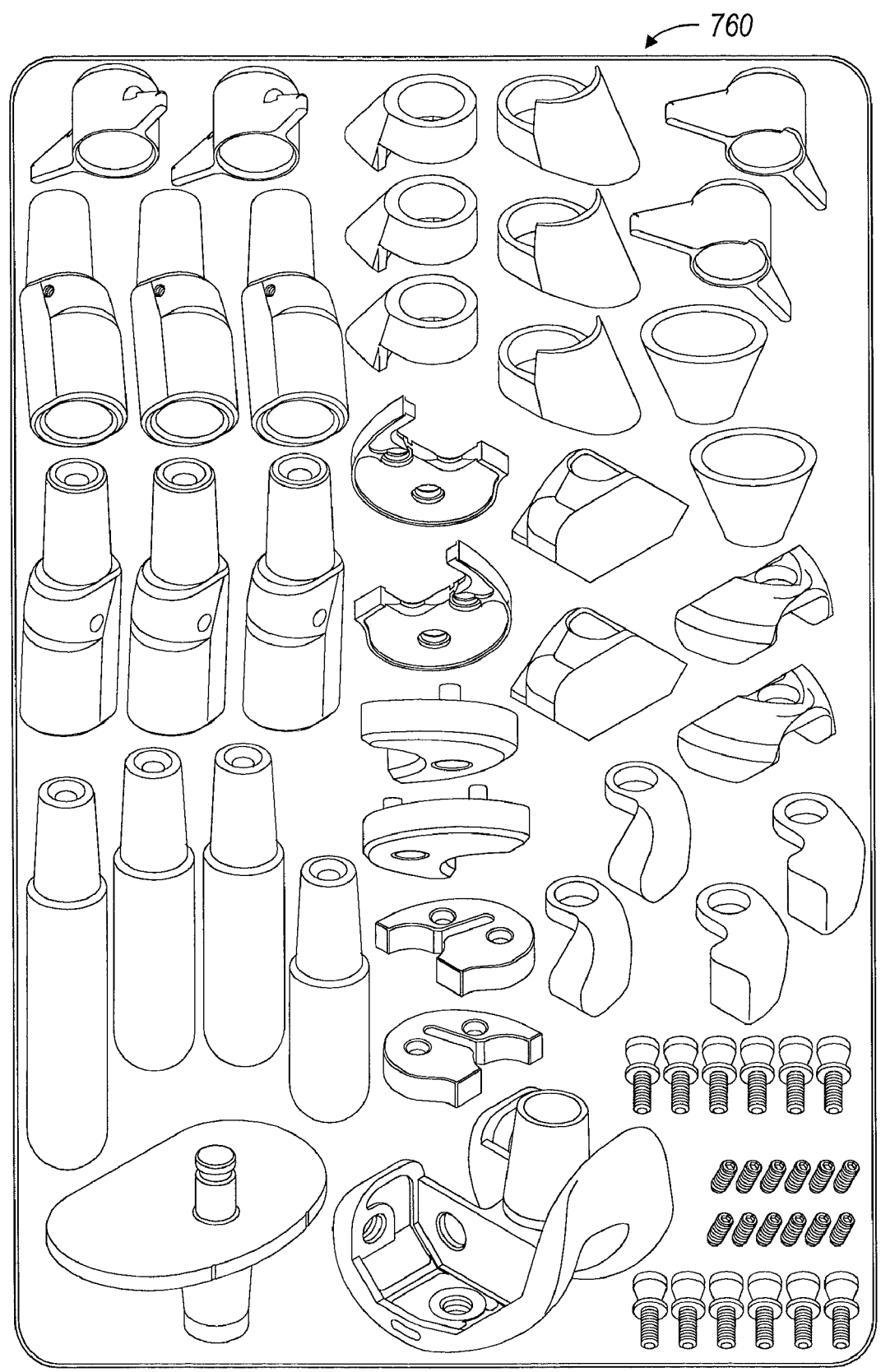
FIGS. 55A and 55B illustrates a kit of implants according to the present teachings.
Figure 55B:
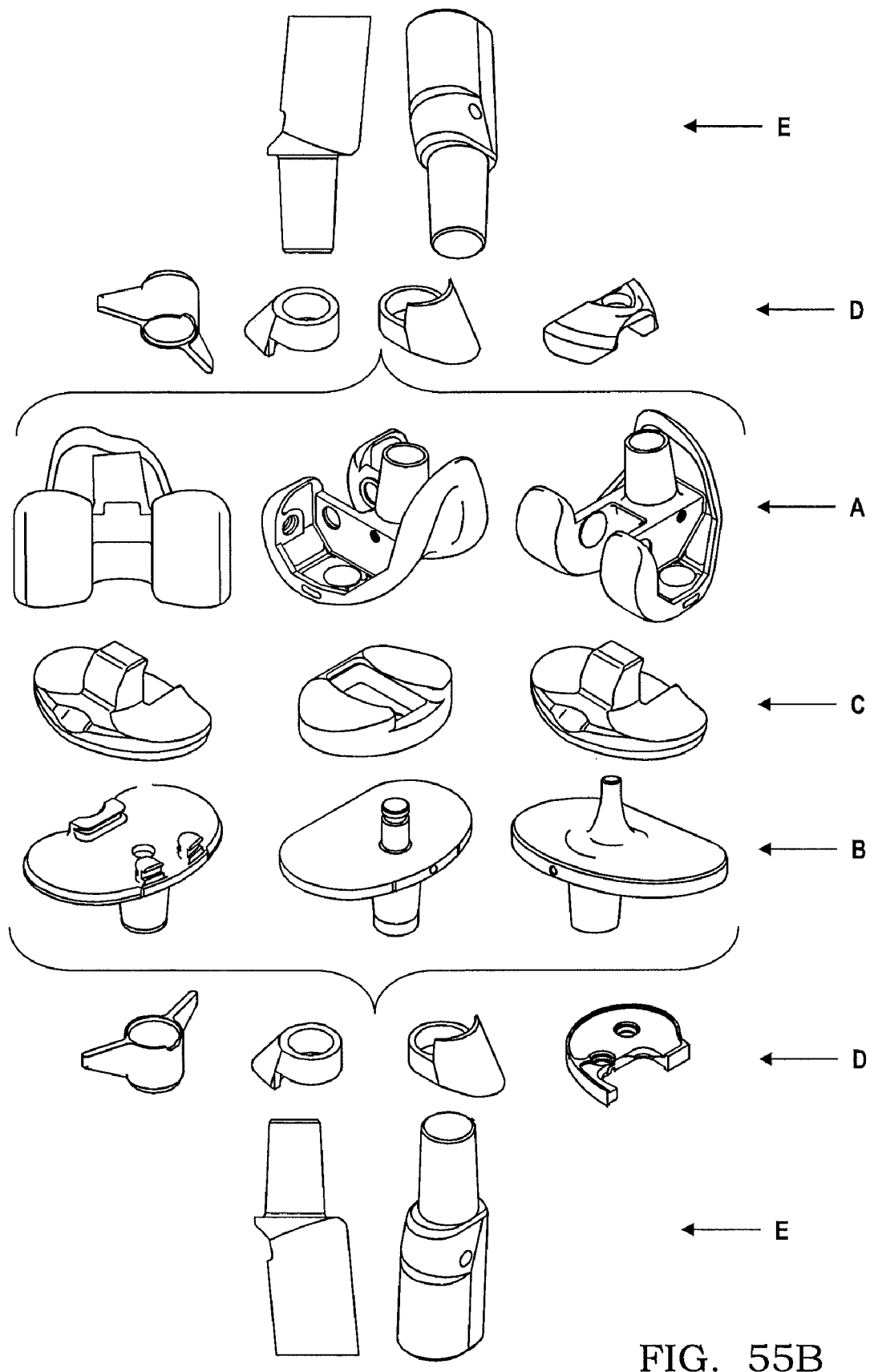
Figure 56:
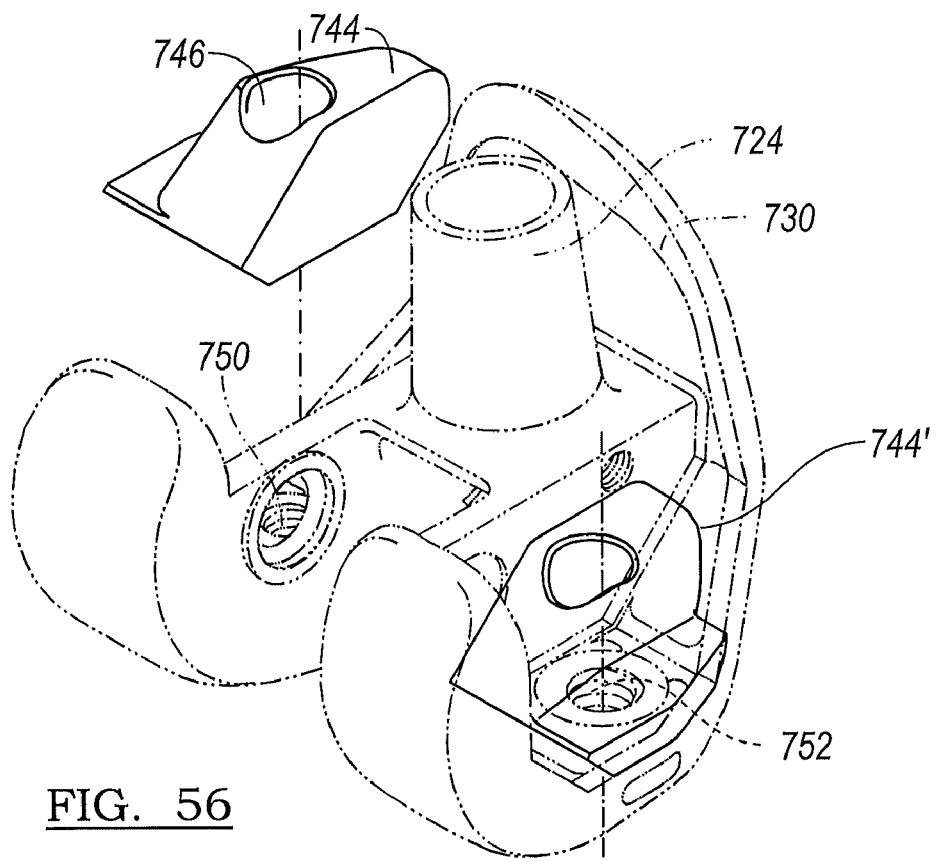
FIGS. 56-60 illustrate various augments shown during stages of assembly.

FIGS. 55A illustrates a kit of components 760. The kit of components can be used interchangeably as discussed herein. The stems can define various lengths and diameters. The adapters can define various offsets. FIG. 55B illustrates such interchangeability. For instance, a surgeon can intraoperatively select a desired femoral component A, a tibial component B, a bearing C, and augment D and an offset adapter E. While not shown, a suitable stem (such as stem 20) can also be coupled to the offset adapter E as described herein.

As described herein, the tapered female receiving portions have been described as receiving the tapered male insertion portions by way of press-fit. Explained further, the female receiving portions and male insertion portions all define conical engaging surfaces adapted to provide a friction fit formed by a Morse-type taper.

While the disclosure has been described in the specification and illustrated in the drawings with reference to a preferred embodiment, it will be understood by those skilled in the art that various changes may be made and equivalents may be substituted for elements thereof without departing from the scope of the disclosure as defined in the claims. In addition, many modifications may be made to adapt a particular situation or material to the teachings of the disclosure without departing from the essential scope thereof. Therefore, it is intended that the disclosure not be limited to the particular embodiment illustrated by the drawings and described in the specification as the best mode presently contemplated for carrying out this disclosure, but that the disclosure will include any embodiments falling within the description of the appended claims.

What is claimed is:

1. A knee joint prosthesis system comprising:
   a first knee prosthesis component including a femoral component having a first attachment portion formed thereon;
   a second knee prosthesis component including a tibial component having a second attachment portion formed thereon;
   at least a first stem defining a stem engagement portion; and
   a first adapter having a first adapter engagement portion defining a male insertion portion defining a first axis and a second adapter engagement portion having an offset body portion that is offset from the male insertion portion and includes a female receiving portion defining a second axis, the first and second axes being parallel and offset;
   wherein the stem engagement portion is operable to intraoperatively couple directly with each of the second adapter engagement portion, the first attachment portion or the second attachment portion;
   and wherein the first adapter engagement portion is operable to intraoperatively couple with the first or the second attachment portion.

2. The system of claim 1 wherein the first knee prosthesis component includes a plurality of femoral components and the second knee prosthesis component includes a plurality of tibial components.

3. The system of claim 2 wherein at least one of the femoral components and at least one of the tibial components cooperate to form each of a crutiate retaining (CR) knee prosthesis, a posterior stabilized (PS) knee prosthesis, a fully constrained knee prosthesis, and a hinged knee prosthesis.

4. The system of claim 3, further comprising a tibial bearing selected from the group consisting of a fixed bearing, a floating bearing, and a rotating bearing.

5. The system of claim 1, further comprising a plurality of stems each having a stem engagement portion and defining distinct lengths or diameters, wherein each of the stem engagement portions are operable to directly couple with each of the first attachment portion, the second attachment portion or the second adapter engagement portion.

6. The system of claim 1, further comprising a plurality of adapters each defining a first axis through a first adapter engagement portion and a second axis through a second adapter engagement portion, wherein an offset defined between a first and a second axis of the first adapter is distinct from an offset defined between a first and a second axis of another adapter of the plurality of adapters.

7. The system of claim 1 wherein the first attachment portion defines a female tapered receiving portion, and the stem engagement portion defines a male tapered insertion portion, wherein the female tapered receiving portion cooperatively engages the male tapered insertion portion by way of a Morse-type taper fit.

8. The system of claim 1, further comprising a first locking member that passes through an adapter bore defined in the first adapter, the first locking member operable to lock the first stem to the first adapter.

9. The system of claim 8 wherein the adapter bore is threaded and wherein the first locking member threadably advances along the adapter bore between an unsecured position and a secured position.

10. The system of claim 9, further comprising an insert secured to the stem wherein the first locking member engages the insert at an interface area in the secured position.

11. The system of claim 10 wherein the first locking member is formed of a harder material than the insert such that a depression is formed in the insert at an interface area upon advancement of the first locking member to the secured position.

12. The system of claim 11 wherein the insert defines a conical head, wherein the first locking member engages the conical head in the secured position.

13. The system of claim 9, further comprising a second locking member that passes through a prosthesis bore defined in the first prosthesis, the second locking member operable to lock the first prosthesis to the first adapter, wherein the first and second locking members are substantially equivalent.

14. The system of claim 13 wherein the prosthesis bore is defined through a femoral box in a femoral component.

15. The system of claim 13 wherein the prosthesis bore is defined through a tray portion of a tibial tray.

16. The system of claim 1 wherein the femoral component and the tibial component are cooperatively coupled by a hinge, wherein the hinge defines a keel having an axle that is biased outwardly along its length, the axle engaging hubs disposed on a femoral box of the femoral component in an implanted position.

17. A knee joint prosthesis system comprising:
    a first knee prosthesis component having a first attachment portion formed thereon;
    at least a first stem defining a stem engagement portion;
    a first insert secured to the stem;
    a first adapter having a first adapter engagement portion defining a first axis and a second adapter engagement portion defining a second axis, the first and second axes being parallel and offset, the first adapter defining an adapter bore;
    a first locking member formed of a harder material than the first insert and that is configured to pass through the adapter bore between an unsecured position wherein the first stem is unlocked from the second adapter engagement portion and a secured position wherein the first locking member engages the first insert creating a depression in the first insert and locks the first stem to the second adapter engagement portion; and wherein the first attachment portion is operable to intraoperatively couple directly with each of the stem engagement portion or the first adapter engagement portion.

18. The system of claim 17, further comprising a second knee prosthesis component distinct from the first knee prosthesis component and having a second attachment portion, wherein the second attachment portion is operable to couple with the stem engagement portion or the first engagement portion.

19. The system of claim 18 wherein the first knee prosthesis component is a femoral component and the second knee prosthesis component is a tibial component.

20. The system of claim 19 wherein the first knee prosthesis component includes a plurality of femoral components and the second knee prosthesis component includes a plurality of tibial components.

21. The system of claim 20 wherein at least one of the femoral components and at least one of the tibial components cooperate to form each of a crutiate retaining (CR) knee prosthesis, a posterior stabilized (PS) knee prosthesis, a fully constrained knee prosthesis, and a hinged knee prosthesis.

22. The system of claim 21, further comprising a tibial bearing selected from the group consisting of a fixed bearing, a floating bearing, and a rotating bearing.

23. The system of claim 17 wherein the stem engagement portion is operable to couple with the second adapter engagement portion.

24. The system of claim 17, further comprising a plurality of stems each having a stem engagement portion and defining distinct lengths or diameters, wherein each of the stem engagement portions are operable to directly couple with both of the first attachment portion of the knee prosthesis component or the second adapter engagement portion of the adapter.

25. The system of claim 17, further comprising a plurality of adapters each defining a first axis through a first adapter engagement portion and a second axis through a second adapter engagement portion, wherein an offset defined between a first and a second axis of the first adapter is distinct from an offset defined between a first and a second axis of another adapter of the plurality of adapters.

26. The system of claim 17 wherein the first attachment portion defines a female tapered receiving portion, and the stem engagement portion and the first adapter engagement portion each define a male tapered insertion portion, wherein the female tapered receiving portion cooperatively engages the male tapered insertion portion by way of a Morse-type taper fit.

27. The system of claim 17 wherein the adapter bore is threaded and wherein the first locking member threadably advances along the adapter bore between an unsecured position and a secured position.

28. The system of claim 17, further comprising a second locking member that passes through a prosthesis bore defined in the first prosthesis, the second locking member operable to engage a second insert on the first adapter and lock the first prosthesis to the first adapter, wherein the first and second locking members are substantially equivalent and the first and second inserts are substantially equivalent.

29. The system of claim 28 wherein the prosthesis bore is defined through a femoral box in a femoral component.

30. The system of claim 28 wherein the prosthesis bore is defined through a tray portion of a tibial tray.

31. A knee joint prosthesis system comprising:
a first knee prosthesis component having a first attachment portion formed thereon and a prosthesis bore defined therethrough;
at least a first stem defining a stem engagement portion;
a first adapter having a first adapter engagement portion including a male insertion portion defining a first axis and a second adapter engagement portion having an offset body portion that is offset from the male insertion portion and includes a female receiving portion defining a second axis, the first and second axes being parallel and offset, the first adapter defining an adapter bore;
wherein the stem engagement portion is operable to intraoperatively couple directly with both of the first attachment portion or the first adapter engagement portion;
a first insert extending from the first stem;
a second insert extending from the first adapter engagement portion;
a first locking member that is configured to pass through the prosthesis bore and engage the first insert or the second insert; and
a second locking member that is configured to pass through the adapter bore and engage the first insert, wherein the first and second inserts are substantially equivalent and the first and second locking members are substantially equivalent.

32. The system of claim 31, further comprising a second knee prosthesis component distinct from the first knee prosthesis component and having a second attachment portion, wherein the second attachment portion is operable to couple with the stem engagement portion or the first adapter engagement portion.

33. The system of claim 32 wherein the first knee prosthesis component is a femoral component and the second knee prosthesis component is a tibial component.

34. The system of claim 33 wherein the first knee prosthesis component includes a plurality of femoral components and the second knee prosthesis component includes a plurality of tibial components.

35. The system of claim 34 wherein at least one of the femoral components and at least one of the tibial components cooperate to form each of a crutiate retaining (CR) knee prosthesis, a posterior stabilized (PS) knee prosthesis, a fully constrained knee prosthesis, and a hinged knee prosthesis.

36. The system of claim 35, further comprising a tibial bearing selected from the group consisting of a fixed bearing, a floating bearing, and a rotating bearing.

37. The system of claim 31, further comprising a plurality of stems each having a stem engagement portion and defining distinct lengths or diameters, wherein each of the stem engagement portions are operable to directly couple with both of the first attachment portion of the knee prosthesis component or the second adapter engagement portion of the adapter.

38. The system of claim 31, further comprising a plurality of adapters each defining a first axis through a first adapter engagement portion and a second axis through a second adapter engagement portion, wherein an offset defined between a first and a second axis of the first adapter is distinct from an offset defined between a first and a second axis of another adapter of the plurality of adapters.

39. The system of claim 31 wherein the prosthesis bore and the adapter bore are both threaded and wherein the respective first and second locking members threadably advance along the prosthesis and adapter bores between an unsecured position and a secured position.

40. The system of claim 31 wherein the first and second locking members are formed of a harder material that the first and second inserts such that a depression is formed into the inserts at an interface area upon advancement of the respective first and second locking members to the secured position.

41. The system of claim 40 wherein first and second inserts define a conical head, wherein the respective first and second locking members engage the respective conical heads in the secured position.

42. The system of claim 31 wherein the prosthesis bore is defined through a femoral box in a femoral component.

43. The system of claim 31 wherein the prosthesis bore is defined through a tray portion of a tibial tray.

44. A knee joint prosthesis system comprising:
- a first knee prosthesis component including a femoral component having a first attachment portion formed thereon;
- a second knee prosthesis component including a tibial component having a second attachment portion formed thereon wherein the femoral component and the tibial component are cooperatively coupled by a hinge, wherein the hinge defines a keel having an axle that is biased outwardly along its length, the axle engaging hubs disposed on a femoral box of the femoral component in an implanted position;
- at least a first stem defining a stem engagement portion; and
- a first adapter having a first adapter engagement portion including a male insertion portion defining a first axis and a second adapter engagement portion having an offset body portion that is offset from the male insertion portion and includes a female receiving portion defining a second axis, the first and second axes being parallel and offset;
- wherein the stem engagement portion is operable to intraoperatively couple with the second adapter engagement portion, the first attachment portion or the second attachment portion;
- and wherein the first adapter engagement portion is operable to intraoperatively couple directly with each of the first or the second attachment portion.

45. The system of claim 44 wherein the first knee prosthesis component includes a plurality of femoral components and the second knee prosthesis component includes a plurality of tibial components.

46. The system of claim 44, further comprising a plurality of stems each having a stem engagement portion and defining distinct lengths or diameters, wherein each of the stem engagement portions are operable to couple with the first attachment portion, the second attachment portion or the second adapter engagement portion.

* * * * *

UNITED STATES PATENT AND TRADEMARK OFFICE
CERTIFICATE OF CORRECTION

| | | |
|---|---|---|
| PATENT NO. | : 8,157,869 B2 | |
| APPLICATION NO. | : 11/972359 | |
| DATED | : April 17, 2012 | |
| INVENTOR(S) | : Robert Metzger et al. | |

It is certified that error appears in the above-identified patent and that said Letters Patent is hereby corrected as shown below:

Column 1, line 35, "prosthesis" should be --prostheses--. Both occurrences

Column 1, line 41, "crutiate" should be --cruciate--.

Column 2, line 1, "crutiate" should be --cruciate--.

Column 3, line 31, after "is" insert --a--.

Column 3, line 31, "an" should be --a--.

Column 4, line 38, "illustrates" should be --illustrate--.

Column 4, line 49, "crutiate" should be --cruciate--.

Column 5, line 5, "crutiate" should be --cruciate--.

Column 7, line 47, after "extending" delete "the".

Column 10, line 2, "Vanguardo" should be --Vanguard®--.

Column 10, line 67, "second end and 408" should be --second end 408--.

Column 14, line 3, "treaded passage 646" should be --threaded passage 646--.

Column 14, line 55, "by" should be --be--.

Column 17, line 1, "FIGS. 55A" should be --FIG. 55A--.

Column 17, line 40, "defining a male" should be --including a male--.

Column 17, line 59, "crutiate" should be --cruciate--.

Column 18, line 43, "in a femoral" should be --in the femoral--.

Column 18, line 45, "of a tibial tray" should be --of the tibial tray--.

Column 19, line 10, after "first" insert --adapter--.

Column 19, line 22, "crutiate" should be --cruciate--.

Column 20, line 43, "crutiate" should be --cruciate--.

Column 21, line 2, "that" should be --than--.

Signed and Sealed this
Twenty-sixth Day of June, 2012

David J. Kappos
*Director of the United States Patent and Trademark Office*